(12) United States Patent
Gallo et al.

(10) Patent No.: US 9,340,769 B2
(45) Date of Patent: May 17, 2016

(54) **METHODS AND COMPOSITIONS FOR TREATING *P. ACNES***

(75) Inventors: Richard L. Gallo, San Diego, CA (US); Chun-Ming Huang, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 150 days.

(21) Appl. No.: 13/132,905

(22) PCT Filed: Dec. 3, 2009

(86) PCT No.: PCT/US2009/066577
§ 371 (c)(1),
(2), (4) Date: Jun. 3, 2011

(87) PCT Pub. No.: WO2010/065735
PCT Pub. Date: Jun. 10, 2010

(65) Prior Publication Data
US 2011/0243960 A1     Oct. 6, 2011

Related U.S. Application Data

(60) Provisional application No. 61/120,221, filed on Dec. 5, 2008.

(51) Int. Cl.
| | |
|---|---|
| *A01N 63/00* | (2006.01) |
| *A61K 45/00* | (2006.01) |
| *A61K 48/00* | (2006.01) |
| *A61K 39/02* | (2006.01) |
| *A61K 39/08* | (2006.01) |
| *A61K 39/09* | (2006.01) |
| *A61K 39/106* | (2006.01) |
| *A61K 39/108* | (2006.01) |
| *A61K 39/112* | (2006.01) |
| *C12N 1/36* | (2006.01) |
| *A61K 45/06* | (2006.01) |
| *A61K 39/00* | (2006.01) |

(52) U.S. Cl.
CPC . *C12N 1/36* (2013.01); *A61K 39/02* (2013.01); *A61K 45/06* (2013.01); *A61K 2039/523* (2013.01); *A61K 2039/5256* (2013.01)

(58) Field of Classification Search
None
See application file for complete search history.

(56) References Cited

U.S. PATENT DOCUMENTS 6,566,108 B1 * 5/2003 Wolf et al. .................... 435/189
2008/0255252 A1 * 10/2008 Cohen et al. ................. 514/789

FOREIGN PATENT DOCUMENTS

| EP | 0914778 A1 | 5/1999 | |
|---|---|---|---|
| EP | 000914778 A1 * | 12/1999 | ............... A61P 37/04 |
| WO | WO 01/81581 * | 1/2001 | ............ C07K 14/195 |
| WO | WO 01/81581 A2 * | 11/2001 | ............ C07K 14/195 |

OTHER PUBLICATIONS

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473, 2000.*
Bruggemann et al., "The complete genome sequence of Propioibacterium acnes, a commensal of human skin," Science, Jul. 30, 2004, pp. 671-673, vol. 305, No. 5684.
Falcone et al., "Activation of acid sphingomyelinase and its inhibition by the nitric oxide/cyclic guanosine 3', 5'-monophopshae pathway: key events in *Escherichi coli*-elicited apoptosis of dendritic cells," J. Immunol. Oct. 1, 2004, pp. 4452-4463, vol. 173, No. 7.
Nakatsuji et al., "Antibodies eleicited by inactivated propionibacterium acnes-based vaccines exert protective immunity and attenuate the IL_8 production in human sebocytes: relevance to therapy for acne vulgaris," J. Invest. Dermatol., Oct. 2008, Epub May 8, 2008, pp. 2451-2457, vol. 128, No. 10.
Nakatsuji et al., "Vaccination targeting a surface sialidase of P. acnes: implication for new treatment of acne vulgaris," PLoS One, Feb. 6, 2008, p. e1551.
Sorensen et al., "Mutagenesis of Propionibacterium acnes and analysis of two CAMP factor knock-out muants," J. of Microbiol. Methods, 2010, doi: 10.1016/j.mimet2010.09.008.
Valanne et al., "CAMP factor homologues in Propionibacterium acnes: a new protein family differentially expressed by types I and II," Microbiology, May 2005, pp. 1369-1379, vol. 151, Part 5.
Nakatsuji et al., "Propionibacterium acnes Camp Factor and Host Acid Sphingomyelinase Contribute to Bacterial Virulence: Potential Targets for Inflammatory Acne Treatment", PLOS One, vol. 6, No. 4, Apr. 12, 2011.
Jiang et al., "Cloning, Sequencing and Expression of the Camp Factor Gene of *Streptococcus uberis*", Microbial Pathogenesis, Academic Press Limited, New York, NY, US, vol. 20, No. 5, Jan. 1, 1996.
Wassem El-Huneidi et al., "*Streptococcus agalactiae* CAMP factor/protein B does not bind to human IgG", Medical Microbiology and Immunology, Springer, Berlin, DE, vol. 196, No. 2, Nov. 4, 2006.
Seranski, Peter, Extended European Search Report issued in European Patent Application No. 09831116.0, European Patent Office, Mar. 18, 2013.

* cited by examiner

*Primary Examiner* — Nora Rooney
(74) *Attorney, Agent, or Firm* — Joseph R. Baker, Jr.; Gavrilovich, Dodd & Lindsey LLP

(57) ABSTRACT

The disclosure provides an antigenic composition useful for immunization against *P. acnes, K. pneumoniae, S. aureus,* or *Streptococcus pyogenes*. The disclosure provides a method for producing a vaccine for preventing infection and screening agents useful for preventing infection.

15 Claims, 21 Drawing Sheets

SEQUENCE LISTING

```
<160> NUMBER OF SEQ ID NOS: 21

<210> SEQ ID NO 1
<211> LENGTH: 12
<212> TYPE: PRT
<213> ORGANISM: Artificial Sequence
<220> FEATURE:
```

<223> OTHER INFORMATION: Peptide fragment from P. Acnes

<400> SEQUENCE: 1

Ser Tyr Ser Glu Lys His Leu Gly Val Ala Phe Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide Fragment from P. Acnes CAMP factor

<400> SEQUENCE: 2

Asp Leu Leu Lys Ala Ala Phe Asp Leu Arg
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Peptide Fragment from P. Acnes CAMP Factor

<400> SEQUENCE: 3

Ala Val Leu Leu Thr Ala Asn Pro Ala Ser Thr Ala Lys
1               5                   10

<210> SEQ ID NO 4
<211> LENGTH: 40
<212> TYPE: DNA
<213> ORGANISM: Artificial Sequence
<220> FEATURE:
<223> OTHER INFORMATION: Oligonucleotide Primer

<400> SEQUENCE: 4
taaggcctct gtcgacgtcg agccgacgac gaccatctcg        40

<210> SEQ ID NO 5
<211> LENGTH: 41
<212> TYPE: DNA
<213> ORGANISM: Artificial Sequence
<220> FEATURE:
<223> OTHER INFORMATION: Oligonucleotide Primer

<400> SEQUENCE: 5
cagaattcgc aagcttggca gccttcttga catcggggga g       41

<210> SEQ ID NO 6
<211> LENGTH: 804
<212> TYPE: DNA
<213> ORGANISM: Propionibacterium acnes
<220> FEATURE:
<221> NAME/KEY: CDS
<222> LOCATION: (1)..(804)

<400> SEQUENCE: 6 atg aag aag acc cat ctt gta gct ccc ctc ctt gtc ggc gca atg ctc     48
Met Lys Lys Thr His Leu Val Ala Pro Leu Leu Val Gly Ala Met Leu
1               5                   10                  15 gta cca gcg gcg ctg tca gct ccc agt gct cat gct gtc gag ccg acg     96
Val Pro Ala Ala Leu Ser Ala Pro Ser Ala His Ala Val Glu Pro Thr
            20                  25                  30 acg acc atc tcg gcg acc agc acc cac gag ctc tcg gcc agt gac gct   144
Thr Thr Ile Ser Ala Thr Ser Thr His Glu Leu Ser Ala Ser Asp Ala
        35                  40                  45

```
cgc aat agc atc cag ctt ctg aac gca cat att gcg acc ctt cag tca       192
Arg Asn Ser Ile Gln Leu Leu Asn Ala His Ile Ala Thr Leu Gln Ser
    50                  55                  60 gta cag aaa tcc gtc ccc ggt tct gac tac tct gac cag atc cga gat       240
Val Gln Lys Ser Val Pro Gly Ser Asp Tyr Ser Asp Gln Ile Arg Asp
65                  70                  75                  80 ctt ctc aag gct gcc ttc gac ctg cgt ggc ctc atc gag acc ctt gcc       288
Leu Leu Lys Ala Ala Phe Asp Leu Arg Gly Leu Ile Glu Thr Leu Ala
                85                  90                  95 cat ggg ggc atc ccg ttc tac gac cct tcg acg atc atg ccg agg atc       336
His Gly Gly Ile Pro Phe Tyr Asp Pro Ser Thr Ile Met Pro Arg Ile
            100                 105                 110 aag ttg gtc gcc acc act att gac acc att cac act gct acc acc act       384
Lys Leu Val Ala Thr Thr Ile Asp Thr Ile His Thr Ala Thr Thr Thr
        115                 120                 125 ctc caa aac aag gtc agc ccc gcc cac gtc gaa ctc ggt ctc gaa gtc       432
Leu Gln Asn Lys Val Ser Pro Ala His Val Glu Leu Gly Leu Glu Val
130                 135                 140 acc aag gcc gtc ctg ctg acc gct aac cca gcg tcc acc gcc aag gaa       480
Thr Lys Ala Val Leu Leu Thr Ala Asn Pro Ala Ser Thr Ala Lys Glu
145                 150                 155                 160 ctc gac gcc gag ggc gcc gcc ctc aag gct cgc ctg gaa aag gtc tcg       528
Leu Asp Ala Glu Gly Ala Ala Leu Lys Ala Arg Leu Glu Lys Val Ser
                165                 170                 175 cag tac ccc gac ctc acc ccg aat gac gtt gcc act gtg tac gta cgc       576
Gln Tyr Pro Asp Leu Thr Pro Asn Asp Val Ala Thr Val Tyr Val Arg
            180                 185                 190 acc aac ttc agt aag acg atc tgg cag gtg cgc gcc aac cgt gac cgg       624
Thr Asn Phe Ser Lys Thr Ile Trp Gln Val Arg Ala Asn Arg Asp Arg
        195                 200                 205 tac atc ctt ggt cac aag agc gcc gca gtg tac aag acg ctc aat cac       672
Tyr Ile Leu Gly His Lys Ser Ala Ala Val Tyr Lys Thr Leu Asn His
210                 215                 220 gcg atc acc aag gcc gtc ggc gtt cga ctg aac cca aag acg acc gta       720
Ala Ile Thr Lys Ala Val Gly Val Arg Leu Asn Pro Lys Thr Thr Val
225                 230                 235                 240 ggg aat atc cag gct gca cgc acc gag ctc ctt gcg gcc tat cag acc       768
Gly Asn Ile Gln Ala Ala Arg Thr Glu Leu Leu Ala Ala Tyr Gln Thr
                245                 250                 255 gca ttc aac tcc ccc gat gtc aag aag gct gcc tga                       804
Ala Phe Asn Ser Pro Asp Val Lys Lys Ala Ala
            260                 265

<210> SEQ ID NO 7
<211> LENGTH: 267
<212> TYPE: PRT
<213> ORGANISM: Propionibacterium acnes

<400> SEQUENCE: 7

Met Lys Lys Thr His Leu Val Ala Pro Leu Leu Val Gly Ala Met Leu
1               5                   10                  15

Val Pro Ala Ala Leu Ser Ala Pro Ser Ala His Ala Val Glu Pro Thr
            20                  25                  30

Thr Thr Ile Ser Ala Thr Ser Thr His Glu Leu Ser Ala Ser Asp Ala
        35                  40                  45

Arg Asn Ser Ile Gln Leu Leu Asn Ala His Ile Ala Thr Leu Gln Ser
    50                  55                  60

Val Gln Lys Ser Val Pro Gly Ser Asp Tyr Ser Asp Gln Ile Arg Asp
65                  70                  75                  80
```

```
Leu Leu Lys Ala Ala Phe Asp Leu Arg Gly Leu Ile Glu Thr Leu Ala
                85                  90                  95

His Gly Gly Ile Pro Phe Tyr Asp Pro Ser Thr Ile Met Pro Arg Ile
            100                 105                 110

Lys Leu Val Ala Thr Thr Ile Asp Thr Ile His Thr Ala Thr Thr Thr
        115                 120                 125

Leu Gln Asn Lys Val Ser Pro Ala His Val Glu Leu Gly Leu Glu Val
    130                 135                 140

Thr Lys Ala Val Leu Leu Thr Ala Asn Pro Ala Ser Thr Ala Lys Glu
145                 150                 155                 160

Leu Asp Ala Glu Gly Ala Ala Leu Lys Ala Arg Leu Glu Lys Val Ser
                165                 170                 175

Gln Tyr Pro Asp Leu Thr Pro Asn Asp Val Ala Thr Val Tyr Val Arg
            180                 185                 190

Thr Asn Phe Ser Lys Thr Ile Trp Gln Val Arg Ala Asn Arg Asp Arg
        195                 200                 205

Tyr Ile Leu Gly His Lys Ser Ala Ala Val Tyr Lys Thr Leu Asn His
    210                 215                 220

Ala Ile Thr Lys Ala Val Gly Val Arg Leu Asn Pro Lys Thr Thr Val
225                 230                 235                 240

Gly Asn Ile Gln Ala Ala Arg Thr Glu Leu Leu Ala Ala Tyr Gln Thr
                245                 250                 255

Ala Phe Asn Ser Pro Asp Val Lys Lys Ala Ala
            260                 265
```

<210> SEQ ID NO 8
<211> LENGTH: 1197
<212> TYPE: DNA
<213> ORGANISM: Propionibacterium acnes
<220> FEATURE:
<221> NAME/KEY: CDS
<222> LOCATION: (79)..(1098)

<400> SEQUENCE: 8

```
ttttgtagg ctacccttt cgaattgaat caatatgatt cacgaaattc gccccgtagt      60
tccgctgagg agtcactg atg aag atc aac gca cga ttc gcc gtc atg gcc    111
                    Met Lys Ile Asn Ala Arg Phe Ala Val Met Ala
                     1               5                  10 gcg agt gtg gcc gtc ctg atg gct gcc gcg ccg att gcg cag gct gct    159
Ala Ser Val Ala Val Leu Met Ala Ala Ala Pro Ile Ala Gln Ala Ala
         15                  20                  25 act tcg ccg ggg gat atc cat ccc ctg gtc cag gca gcc cac agc ccc    207
Thr Ser Pro Gly Asp Ile His Pro Leu Val Gln Ala Ala His Ser Pro
     30                  35                  40 gac ggt att ccc ggt aac ggc gtc ggg ccg gaa ttc cat acg tcg tcg    255
Asp Gly Ile Pro Gly Asn Gly Val Gly Pro Glu Phe His Thr Ser Ser
 45                  50                  55 atg gcg cgt tcc tac agc gag aag cac ctg ggc gtg gcg ccg cgg ggt    303
Met Ala Arg Ser Tyr Ser Glu Lys His Leu Gly Val Ala Pro Arg Gly
 60                  65                  70                  75 gtg aac gac ttc tcc tgc aag gtc aag ccc ggc gac cga ccg gtc atc    351
Val Asn Asp Phe Ser Cys Lys Val Lys Pro Gly Asp Arg Pro Val Ile
                 80                  85                  90 ctg att ccc ggt act ggc ggc aat gcg ttc gcc aca tgg tcc ttc tac    399
Leu Ile Pro Gly Thr Gly Gly Asn Ala Phe Ala Thr Trp Ser Phe Tyr
         95                 100                 105 gga ccc cat ctg gcc cat gag ggg tac tgt gtc tac acc ttc acc acc    447
```

```
                Gly Pro His Leu Ala His Glu Gly Tyr Cys Val Tyr Thr Phe Thr Thr
                            110                 115                 120 aat gtc ccc gtg ggg atc ctc gac gag ggc tgg ggc ttc acc ggt gac        495
Asn Val Pro Val Gly Ile Leu Asp Glu Gly Trp Gly Phe Thr Gly Asp
125                 130                 135 gtg cgc gcc tcc gcg cag gcg ctg ggt gcc ttt gtg gat cgg gtc cgg        543
Val Arg Ala Ser Ala Gln Ala Leu Gly Ala Phe Val Asp Arg Val Arg
140                 145                 150                 155 aaa gcg acg ggc tct gag aag gtc gac ttc gtc gga cat tcg cag ggt        591
Lys Ala Thr Gly Ser Glu Lys Val Asp Phe Val Gly His Ser Gln Gly
                160                 165                 170 ggc ggc atc ctg ccg aac gcc tac atc aag atg tat ggc gga gcg tcc        639
Gly Gly Ile Leu Pro Asn Ala Tyr Ile Lys Met Tyr Gly Gly Ala Ser
            175                 180                 185 aag gtc gac aag ctg atc gga ctg gtg gcc gcc aac cac ggc acc acc        687
Lys Val Asp Lys Leu Ile Gly Leu Val Ala Ala Asn His Gly Thr Thr
        190                 195                 200 gcc gtc ggt ctc gac aag ctt gtc gac ggc ctg ccc gag gct gtg aag        735
Ala Val Gly Leu Asp Lys Leu Val Asp Gly Leu Pro Glu Ala Val Lys
205                 210                 215 gat ttc ctt agc acg tgg agc tac gac cac aac atg gag gcc tac ggc        783
Asp Phe Leu Ser Thr Trp Ser Tyr Asp His Asn Met Glu Ala Tyr Gly
220                 225                 230                 235 cag cag ctc aag gga tca gcg ttg atg caa cag gtt tac cgt gac ggc        831
Gln Gln Leu Lys Gly Ser Ala Leu Met Gln Gln Val Tyr Arg Asp Gly
                240                 245                 250 gac acc gtc ccg ggt atc gcc tac acc gtc atc tcc acc cgg ctc gac        879
Asp Thr Val Pro Gly Ile Ala Tyr Thr Val Ile Ser Thr Arg Leu Asp
            255                 260                 265 atg acg gtc acg ccc tac acg caa gcc ttc ctc aag ggc gcc aag aac        927
Met Thr Val Thr Pro Tyr Thr Gln Ala Phe Leu Lys Gly Ala Lys Asn
        270                 275                 280 atg acc gtg cag gac gcc tgc cct ctg gat gcc tat ggc cac ggc cgc        975
Met Thr Val Gln Asp Ala Cys Pro Leu Asp Ala Tyr Gly His Gly Arg
285                 290                 295 cta ccc tat gat ccc gtc gcc tac cag atg gtg ctc aac gcc ctc gat       1023
Leu Pro Tyr Asp Pro Val Ala Tyr Gln Met Val Leu Asn Ala Leu Asp
300                 305                 310                 315 ccg aac cac cca cga gag atc tcc tgc acg tgg cgg ccc cgg gtt ctg       1071
Pro Asn His Pro Arg Glu Ile Ser Cys Thr Trp Arg Pro Arg Val Leu
                320                 325                 330 ccc gta tcc acc acg gat gct gca tga actgtggcag gtcagggttc             1118
Pro Val Ser Thr Thr Asp Ala Ala
            335 tccagcgccg tgcggcgtgg ccaccaacca cgactgtggt gacaacgaac agtactcggt    1178 ccctgccttg tgccgggtg                                                  1197

<210> SEQ ID NO 9
<211> LENGTH: 339
<212> TYPE: PRT
<213> ORGANISM: Propionibacterium acnes

<400> SEQUENCE: 9

Met Lys Ile Asn Ala Arg Phe Ala Val Met Ala Ala Ser Val Ala Val
1               5                   10                  15

Leu Met Ala Ala Ala Pro Ile Ala Gln Ala Thr Ser Pro Gly Asp
            20                  25                  30

Ile His Pro Leu Val Gln Ala Ala His Ser Pro Asp Gly Ile Pro Gly
        35                  40                  45
```

-continued

Asn Gly Val Gly Pro Glu Phe His Thr Ser Ser Met Ala Arg Ser Tyr
            50                  55                  60
Ser Glu Lys His Leu Gly Val Ala Pro Arg Gly Val Asn Asp Phe Ser
 65                  70                  75                  80
Cys Lys Val Lys Pro Gly Asp Arg Pro Val Ile Leu Ile Pro Gly Thr
                 85                  90                  95
Gly Gly Asn Ala Phe Ala Thr Trp Ser Phe Tyr Gly Pro His Leu Ala
            100                 105                 110
His Glu Gly Tyr Cys Val Tyr Thr Phe Thr Thr Asn Val Pro Val Gly
        115                 120                 125
Ile Leu Asp Glu Gly Trp Gly Phe Thr Gly Asp Val Arg Ala Ser Ala
130                 135                 140
Gln Ala Leu Gly Ala Phe Val Asp Arg Val Arg Lys Ala Thr Gly Ser
145                 150                 155                 160
Glu Lys Val Asp Phe Val Gly His Ser Gln Gly Gly Ile Leu Pro
                165                 170                 175
Asn Ala Tyr Ile Lys Met Tyr Gly Gly Ala Ser Lys Val Asp Lys Leu
            180                 185                 190
Ile Gly Leu Val Ala Ala Asn His Gly Thr Thr Ala Val Gly Leu Asp
        195                 200                 205
Lys Leu Val Asp Gly Leu Pro Glu Ala Val Lys Asp Phe Leu Ser Thr
210                 215                 220
Trp Ser Tyr Asp His Asn Met Glu Ala Tyr Gly Gln Gln Leu Lys Gly
225                 230                 235                 240
Ser Ala Leu Met Gln Gln Val Tyr Arg Asp Gly Asp Thr Val Pro Gly
                245                 250                 255
Ile Ala Tyr Thr Val Ile Ser Thr Arg Leu Asp Met Thr Val Thr Pro
            260                 265                 270
Tyr Thr Gln Ala Phe Leu Lys Gly Ala Lys Asn Met Thr Val Gln Asp
        275                 280                 285
Ala Cys Pro Leu Asp Ala Tyr Gly His Gly Arg Leu Pro Tyr Asp Pro
290                 295                 300
Val Ala Tyr Gln Met Val Leu Asn Ala Leu Asp Pro Asn His Pro Arg
305                 310                 315                 320
Glu Ile Ser Cys Thr Trp Arg Pro Arg Val Leu Pro Val Ser Thr Thr
                325                 330                 335
Asp Ala Ala

<210> SEQ ID NO 10
<211> LENGTH: 1896
<212> TYPE: DNA
<213> ORGANISM: Homo sapiens
<220> FEATURE:
<221> NAME/KEY: CDS
<222> LOCATION: (1)..(1896)

<400> SEQUENCE: 10 atg ccc cgc tac gga gcg tca ctc cgc cag agc tgc ccc agg tcc ggc      48
Met Pro Arg Tyr Gly Ala Ser Leu Arg Gln Ser Cys Pro Arg Ser Gly
 1               5                   10                  15 cgg gag cag gga caa gac ggg acc gcc gga gcc ccc gga ctc ctt tgg      96
Arg Glu Gln Gly Gln Asp Gly Thr Ala Gly Ala Pro Gly Leu Leu Trp
                20                  25                  30 atg ggc ctg gtg ctg gcg ctg gcg ctg gcg ctg gcg ctg gct            144
Met Gly Leu Val Leu Ala Leu Ala Leu Ala Leu Ala Leu Ala
            35                  40                  45

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | tct | gac | tct | cgg | gtt | ctc | tgg | gct | ccg | gca | gag | gct | cac | cct | ctt | 192  |
| Leu | Ser | Asp | Ser | Arg | Val | Leu | Trp | Ala | Pro | Ala | Glu | Ala | His | Pro | Leu |      |
|     | 50  |     |     |     | 55  |     |     |     |     | 60  |     |     |     |     |     |      |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| tct | ccc | caa | ggc | cat | cct | gcc | agg | tta | cat | cgc | ata | gtg | ccc | cgg | ctc | 240 |
| Ser | Pro | Gln | Gly | His | Pro | Ala | Arg | Leu | His | Arg | Ile | Val | Pro | Arg | Leu |     |
| 65  |     |     |     |     | 70  |     |     |     |     | 75  |     |     |     |     | 80  |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cga | gat | gtc | ttt | ggg | tgg | ggg | aac | ctc | acc | tgc | cca | atc | tgc | aaa | ggt | 288 |
| Arg | Asp | Val | Phe | Gly | Trp | Gly | Asn | Leu | Thr | Cys | Pro | Ile | Cys | Lys | Gly |     |
|     |     |     |     | 85  |     |     |     |     | 90  |     |     |     |     | 95  |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cta | ttc | acc | gcc | atc | aac | ctc | ggg | ctg | aag | aag | gaa | ccc | aat | gtg | gct | 336 |
| Leu | Phe | Thr | Ala | Ile | Asn | Leu | Gly | Leu | Lys | Lys | Glu | Pro | Asn | Val | Ala |     |
|     |     |     |     | 100 |     |     |     |     | 105 |     |     |     |     | 110 |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cgc | gtg | ggc | tcc | gtg | gcc | atc | aag | ctg | tgc | aat | ctg | ctg | aag | ata | gca | 384 |
| Arg | Val | Gly | Ser | Val | Ala | Ile | Lys | Leu | Cys | Asn | Leu | Leu | Lys | Ile | Ala |     |
|     |     |     | 115 |     |     |     |     | 120 |     |     |     |     | 125 |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cca | cct | gcc | gtg | tgc | caa | tcc | att | gtc | cac | ctc | ttt | gag | gat | gac | atg | 432 |
| Pro | Pro | Ala | Val | Cys | Gln | Ser | Ile | Val | His | Leu | Phe | Glu | Asp | Asp | Met |     |
|     | 130 |     |     |     |     | 135 |     |     |     |     | 140 |     |     |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gtg | gag | gtg | tgg | aga | cgc | tca | gtg | ctg | agc | cca | tct | gag | gcc | tgt | ggc | 480 |
| Val | Glu | Val | Trp | Arg | Arg | Ser | Val | Leu | Ser | Pro | Ser | Glu | Ala | Cys | Gly |     |
| 145 |     |     |     |     | 150 |     |     |     |     | 155 |     |     |     |     | 160 |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| ctg | ctc | ctg | ggc | tcc | acc | tgt | ggg | cac | tgg | gac | att | ttc | tca | tct | tgg | 528 |
| Leu | Leu | Leu | Gly | Ser | Thr | Cys | Gly | His | Trp | Asp | Ile | Phe | Ser | Ser | Trp |     |
|     |     |     |     | 165 |     |     |     |     | 170 |     |     |     |     | 175 |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| aac | atc | tct | ttg | cct | act | gtg | ccg | aag | ccg | ccc | ccc | aaa | ccc | cct | agc | 576 |
| Asn | Ile | Ser | Leu | Pro | Thr | Val | Pro | Lys | Pro | Pro | Pro | Lys | Pro | Pro | Ser |     |
|     |     |     | 180 |     |     |     |     | 185 |     |     |     |     | 190 |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| ccc | cca | gcc | cca | ggt | gcc | cct | gtc | agc | cgc | atc | ctc | ttc | ctc | act | gac | 624 |
| Pro | Pro | Ala | Pro | Gly | Ala | Pro | Val | Ser | Arg | Ile | Leu | Phe | Leu | Thr | Asp |     |
|     |     | 195 |     |     |     |     | 200 |     |     |     |     | 205 |     |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| ctg | cac | tgg | gat | cat | gac | tac | ctg | gag | ggc | acg | gac | cct | gac | tgt | gca | 672 |
| Leu | His | Trp | Asp | His | Asp | Tyr | Leu | Glu | Gly | Thr | Asp | Pro | Asp | Cys | Ala |     |
|     | 210 |     |     |     |     | 215 |     |     |     |     | 220 |     |     |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gac | cca | ctg | tgc | tgc | cgc | cgg | ggt | tct | ggc | ctg | ccg | ccc | gca | tcc | cgg | 720 |
| Asp | Pro | Leu | Cys | Cys | Arg | Arg | Gly | Ser | Gly | Leu | Pro | Pro | Ala | Ser | Arg |     |
| 225 |     |     |     |     | 230 |     |     |     |     | 235 |     |     |     |     | 240 |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cca | ggt | gcc | gga | tac | tgg | ggc | gaa | tac | agc | aag | tgt | gac | ctg | ccc | ctg | 768 |
| Pro | Gly | Ala | Gly | Tyr | Trp | Gly | Glu | Tyr | Ser | Lys | Cys | Asp | Leu | Pro | Leu |     |
|     |     |     |     | 245 |     |     |     |     | 250 |     |     |     |     | 255 |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| agg | acc | ctg | gag | agc | ctg | ttg | agt | ggg | ctg | ggc | cca | gcc | ggc | cct | ttt | 816 |
| Arg | Thr | Leu | Glu | Ser | Leu | Leu | Ser | Gly | Leu | Gly | Pro | Ala | Gly | Pro | Phe |     |
|     |     |     | 260 |     |     |     |     | 265 |     |     |     |     | 270 |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gat | atg | gtg | tac | tgg | aca | gga | gac | atc | ccc | gca | cat | gat | gtc | tgg | cac | 864 |
| Asp | Met | Val | Tyr | Trp | Thr | Gly | Asp | Ile | Pro | Ala | His | Asp | Val | Trp | His |     |
|     |     | 275 |     |     |     |     | 280 |     |     |     |     | 285 |     |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| cag | act | cgt | cag | gac | caa | ctg | cgg | gcc | ctg | acc | acc | gtc | aca | gca | ctt | 912 |
| Gln | Thr | Arg | Gln | Asp | Gln | Leu | Arg | Ala | Leu | Thr | Thr | Val | Thr | Ala | Leu |     |
|     | 290 |     |     |     |     | 295 |     |     |     |     | 300 |     |     |     |     |     |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| gtg | agg | aag | ttc | ctg | ggg | cca | gtg | cca | gtg | tac | cct | gct | gtg | ggt | aac | 960 |
| Val | Arg | Lys | Phe | Leu | Gly | Pro | Val | Pro | Val | Tyr | Pro | Ala | Val | Gly | Asn |     |
| 305 |     |     |     |     | 310 |     |     |     |     | 315 |     |     |     |     | 320 |     |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cat | gaa | agc | aca | cct | gtc | aat | agc | ttc | cct | ccc | ccc | ttc | att | gag | ggc | 1008 |
| His | Glu | Ser | Thr | Pro | Val | Asn | Ser | Phe | Pro | Pro | Pro | Phe | Ile | Glu | Gly |      |
|     |     |     | 325 |     |     |     |     | 330 |     |     |     |     | 335 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aac | cac | tcc | tcc | cgc | tgg | ctc | tat | gaa | gcg | atg | gcc | aag | gct | tgg | gag | 1056 |
| Asn | His | Ser | Ser | Arg | Trp | Leu | Tyr | Glu | Ala | Met | Ala | Lys | Ala | Trp | Glu |      |
|     |     |     | 340 |     |     |     |     | 345 |     |     |     |     | 350 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ccc | tgg | ctg | cct | gcc | gaa | gcc | ctg | cgc | acc | ctc | aga | att | ggg | ggg | ttc | 1104 |
| Pro | Trp | Leu | Pro | Ala | Glu | Ala | Leu | Arg | Thr | Leu | Arg | Ile | Gly | Gly | Phe |      |

```
                 355                 360                 365
tat gct ctt tcc cca tac ccc ggt ctc cgc ctc atc tct ctc aat atg        1152
Tyr Ala Leu Ser Pro Tyr Pro Gly Leu Arg Leu Ile Ser Leu Asn Met
370                 375                 380 aat ttt tgt tcc cgt gag aac ttc tgg ctc ttg atc aac tcc acg gat        1200
Asn Phe Cys Ser Arg Glu Asn Phe Trp Leu Leu Ile Asn Ser Thr Asp
385                 390                 395                 400 ccc gca gga cag ctc cag tgg ctg gtg ggg gag ctt cag gct gct gag        1248
Pro Ala Gly Gln Leu Gln Trp Leu Val Gly Glu Leu Gln Ala Ala Glu
            405                 410                 415 gat cga gga gac aaa gtg cat ata att ggc cac att ccc cca ggg cac        1296
Asp Arg Gly Asp Lys Val His Ile Ile Gly His Ile Pro Pro Gly His
        420                 425                 430 tgt ctg aag agc tgg agc tgg aat tat tac cga att gta gcc agg tat        1344
Cys Leu Lys Ser Trp Ser Trp Asn Tyr Tyr Arg Ile Val Ala Arg Tyr
    435                 440                 445 gag aac acc ctg gct gct cag ttc ttt ggc cac act cat gtg gat gaa        1392
Glu Asn Thr Leu Ala Ala Gln Phe Phe Gly His Thr His Val Asp Glu
450                 455                 460 ttt gag gtc ttc tat gat gaa gag act ctg agc cgg ccg ctg gct gta        1440
Phe Glu Val Phe Tyr Asp Glu Glu Thr Leu Ser Arg Pro Leu Ala Val
465                 470                 475                 480 gcc ttc ctg gca ccc agt gca act acc tac atc ggc ctt aat cct ggt        1488
Ala Phe Leu Ala Pro Ser Ala Thr Thr Tyr Ile Gly Leu Asn Pro Gly
            485                 490                 495 tac cgt gtg tac caa ata gat gga aac tac tcc ggg agc tct cac gtg        1536
Tyr Arg Val Tyr Gln Ile Asp Gly Asn Tyr Ser Gly Ser Ser His Val
        500                 505                 510 gtc ctg gac cat gag acc tac atc ctg aat ctg acc cag gca aac ata        1584
Val Leu Asp His Glu Thr Tyr Ile Leu Asn Leu Thr Gln Ala Asn Ile
    515                 520                 525 ccg gga gcc ata ccg cac tgg cag ctt ctc tac agg gct cga gaa acc        1632
Pro Gly Ala Ile Pro His Trp Gln Leu Leu Tyr Arg Ala Arg Glu Thr
530                 535                 540 tat ggg ctg ccc aac aca ctg cct acc gcc tgg cac aac ctg gta tat        1680
Tyr Gly Leu Pro Asn Thr Leu Pro Thr Ala Trp His Asn Leu Val Tyr
545                 550                 555                 560 cgc atg cgg ggc gac atg caa ctt ttc cag acc ttc tgg ttt ctc tac        1728
Arg Met Arg Gly Asp Met Gln Leu Phe Gln Thr Phe Trp Phe Leu Tyr
            565                 570                 575 cat aag ggc cac cca ccc tcg gag ccc tgt ggc acg ccc tgc cgt ctg        1776
His Lys Gly His Pro Pro Ser Glu Pro Cys Gly Thr Pro Cys Arg Leu
        580                 585                 590 gct act ctt tgt gcc cag ctc tct gcc cgt gct gac agc cct gct ctg        1824
Ala Thr Leu Cys Ala Gln Leu Ser Ala Arg Ala Asp Ser Pro Ala Leu
    595                 600                 605 tgc cgc cac ctg atg cca gat ggg agc ctc cca gag gcc cag agc ctg        1872
Cys Arg His Leu Met Pro Asp Gly Ser Leu Pro Glu Ala Gln Ser Leu
610                 615                 620 tgg cca agg cca ctg ttt tgc tag                                        1896
Trp Pro Arg Pro Leu Phe Cys
625                 630

<210> SEQ ID NO 11
<211> LENGTH: 631
<212> TYPE: PRT
<213> ORGANISM: Homo sapiens

<400> SEQUENCE: 11

Met Pro Arg Tyr Gly Ala Ser Leu Arg Gln Ser Cys Pro Arg Ser Gly
```

```
1               5                   10                  15
Arg Glu Gln Gly Gln Asp Gly Thr Ala Gly Ala Pro Gly Leu Leu Trp
                20                  25                  30

Met Gly Leu Val Leu Ala Leu Ala Leu Ala Leu Ala Leu Ala
                35                  40                  45

Leu Ser Asp Ser Arg Val Leu Trp Ala Pro Ala Glu Ala His Pro Leu
50                      55                  60

Ser Pro Gln Gly His Pro Ala Arg Leu His Arg Ile Val Pro Arg Leu
65                  70                  75                  80

Arg Asp Val Phe Gly Trp Gly Asn Leu Thr Cys Pro Ile Cys Lys Gly
                85                  90                  95

Leu Phe Thr Ala Ile Asn Leu Gly Leu Lys Lys Glu Pro Asn Val Ala
                100                 105                 110

Arg Val Gly Ser Val Ala Ile Lys Leu Cys Asn Leu Leu Lys Ile Ala
                115                 120                 125

Pro Pro Ala Val Cys Gln Ser Ile Val His Leu Phe Glu Asp Asp Met
130                     135                 140

Val Glu Val Trp Arg Arg Ser Val Leu Ser Pro Ser Glu Ala Cys Gly
145                 150                 155                 160

Leu Leu Leu Gly Ser Thr Cys Gly His Trp Asp Ile Phe Ser Ser Trp
                165                 170                 175

Asn Ile Ser Leu Pro Thr Val Pro Lys Pro Pro Lys Pro Pro Ser
                180                 185                 190

Pro Pro Ala Pro Gly Ala Pro Val Ser Arg Ile Leu Phe Leu Thr Asp
                195                 200                 205

Leu His Trp Asp His Asp Tyr Leu Glu Gly Thr Asp Pro Asp Cys Ala
210                     215                 220

Asp Pro Leu Cys Cys Arg Arg Gly Ser Gly Leu Pro Pro Ala Ser Arg
225                 230                 235                 240

Pro Gly Ala Gly Tyr Trp Gly Glu Tyr Ser Lys Cys Asp Leu Pro Leu
                245                 250                 255

Arg Thr Leu Glu Ser Leu Leu Ser Gly Leu Gly Pro Ala Gly Pro Phe
                260                 265                 270

Asp Met Val Tyr Trp Thr Gly Asp Ile Pro Ala His Asp Val Trp His
                275                 280                 285

Gln Thr Arg Gln Asp Gln Leu Arg Ala Leu Thr Thr Val Thr Ala Leu
                290                 295                 300

Val Arg Lys Phe Leu Gly Pro Val Pro Val Tyr Pro Ala Val Gly Asn
305                 310                 315                 320

His Glu Ser Thr Pro Val Asn Ser Phe Pro Pro Phe Ile Glu Gly
                325                 330                 335

Asn His Ser Ser Arg Trp Leu Tyr Glu Ala Met Ala Lys Ala Trp Glu
                340                 345                 350

Pro Trp Leu Pro Ala Glu Ala Leu Arg Thr Leu Arg Ile Gly Gly Phe
                355                 360                 365

Tyr Ala Leu Ser Pro Tyr Pro Gly Leu Arg Leu Ile Ser Leu Asn Met
                370                 375                 380

Asn Phe Cys Ser Arg Glu Asn Phe Trp Leu Leu Ile Asn Ser Thr Asp
385                 390                 395                 400

Pro Ala Gly Gln Leu Gln Trp Leu Val Gly Glu Leu Gln Ala Ala Glu
                405                 410                 415

Asp Arg Gly Asp Lys Val His Ile Ile Gly His Ile Pro Pro Gly His
                420                 425                 430
```

```
Cys Leu Lys Ser Trp Ser Trp Asn Tyr Tyr Arg Ile Val Ala Arg Tyr
            435                 440                 445

Glu Asn Thr Leu Ala Ala Gln Phe Phe Gly His Thr His Val Asp Glu
    450                 455                 460

Phe Glu Val Phe Tyr Asp Glu Glu Thr Leu Ser Arg Pro Leu Ala Val
465                 470                 475                 480

Ala Phe Leu Ala Pro Ser Ala Thr Thr Tyr Ile Gly Leu Asn Pro Gly
                485                 490                 495

Tyr Arg Val Tyr Gln Ile Asp Gly Asn Tyr Ser Gly Ser Ser His Val
            500                 505                 510

Val Leu Asp His Glu Thr Tyr Ile Leu Asn Leu Thr Gln Ala Asn Ile
        515                 520                 525

Pro Gly Ala Ile Pro His Trp Gln Leu Leu Tyr Arg Ala Arg Glu Thr
    530                 535                 540

Tyr Gly Leu Pro Asn Thr Leu Pro Thr Ala Trp His Asn Leu Val Tyr
545                 550                 555                 560

Arg Met Arg Gly Asp Met Gln Leu Phe Gln Thr Phe Trp Phe Leu Tyr
                565                 570                 575

His Lys Gly His Pro Pro Ser Glu Pro Cys Gly Thr Pro Cys Arg Leu
            580                 585                 590

Ala Thr Leu Cys Ala Gln Leu Ser Ala Arg Ala Asp Ser Pro Ala Leu
        595                 600                 605

Cys Arg His Leu Met Pro Asp Gly Ser Leu Pro Glu Ala Gln Ser Leu
    610                 615                 620

Trp Pro Arg Pro Leu Phe Cys
625                 630

<210> SEQ ID NO 12
<211> LENGTH: 1509
<212> TYPE: DNA
<213> ORGANISM: Propionibacterium acnes

<400> SEQUENCE: 12
tcagtctcct gtgtgcggca aactagtggg acgcgacgag gcacctccgt gaagagaacc      60 ggaggggggtc gcagtaagcg ggagagatgt gccagaagtt ggctctccag aagtcggcct    120
cccggaagga gccaccgggc acacggaatt caaccacccc atcggaatgg tggagtaccg    180
aataccgtcg cgctcccaca gaacgcccaa cgccccgtca gactgcaccg ctgccgtggt    240
gtatccgact tccccgggca gtaggtctg atgactgacc catgtccgtc cgtcatcgca    300
ggagaccgag agggtaccgt ttacccgttc cgtggcattg cgggcattcg tgaataacag    360
gatcctggct ttcgccgacc cggcccgggc attggggtaa gcccgaatga tctgggcgtt    420
gttggtgggg tcgatgaggt cgtcgaccag cttcaccggc cccaggtca agccaccgtc     480 atgggaatag gccactttgc gccgaccgga acgggctgcg tccctggaat tgagcatgag    540
ggtaccgtcg acagttcca ccaccttgtt ctcgtccatc attcggccca ccgggttgcc    600
agcatgccag gtgatgccgt gatcatcgga atagatcgac tgggcctgtt ggccgacact    660
gttgcgcacc gtcatctggg caatgagacc tccagcgtgg gggccgtgga gcaacgctat    720
gccctgccct gatgccacga atcgtgtccg agtggtggga tccggggtga tctcgcgcgt    780
gatgtctcga taggtccaag tgtgtccatt gtcggtcgat gtagagacct cggcgtgcag    840
aacatgacga tcatccgggt ccgtgcccac ctccgatgtg gcgaatcctc tgtcgtagga    900
cttcacgtga aaattgagga tgtggcccgt ggctggatcg acgagatagg aaggatcgga    960
```

```
gtatcccacc ttcctgcgac ccagggtccc ggcatggatg acggtttgcg gaccccgcgt    1020
cctaccgttg tcgcgagagc ggcgctgcac gatggaattg ggttaggcg catcggcggc     1080 gctccccgga cgcagatcgt aggaggccag caaatcgccg ttcgaagcgg tcgcaagggc    1140
tgggattcgg taaaaaacac ctgccggatg ctcattgaca gccaaatcca cgacggggcc    1200
aaggagcatc cgtgtgctcg aatcagcacg aacatccggc agaggtgccg gcactgctgc    1260
gggccatgtc cggtcgactt tcataatggc tccttggcg ttccggacga tattcttacc     1320
gaagaagaga tgagtgcccg actgatcggt gctggtgata tcacccgtga cgagcttcgg    1380
ctgggtggtg gccgcatctg ggccggagc cctgcctgat gccatagctg actgcgtcac     1440
catgggagcc ccgatgacgg ccatgattcc ggcaatggcc aacgcgctca gtttcgtggt    1500
caaagtcat                                                            1509

<210> SEQ ID NO 13
<211> LENGTH: 502
<212> TYPE: PRT
<213> ORGANISM: Propionibacterium acnes

<400> SEQUENCE: 13

Met Thr Leu Thr Thr Lys Leu Ser Ala Leu Ala Ile Ala Gly Ile Met
1               5                   10                  15

Ala Val Ile Gly Ala Pro Met Val Thr Gln Ser Ala Met Ala Ser Gly
            20                  25                  30

Arg Ala Pro Ala Pro Asp Ala Ala Thr Thr Gln Pro Lys Leu Val Thr
        35                  40                  45

Gly Asp Ile Thr Ser Thr Asp Gln Ser Gly Thr His Leu Phe Phe Gly
    50                  55                  60

Lys Asn Ile Val Arg Asn Ala Lys Gly Ala Ile Met Lys Val Asp Arg
65                  70                  75                  80

Thr Trp Pro Ala Ala Val Pro Ala Pro Leu Pro Asp Val Arg Ala Asp
                85                  90                  95

Ser Ser Thr Arg Met Leu Leu Gly Pro Val Val Asp Leu Ala Val Asn
            100                 105                 110

Glu His Pro Ala Gly Val Phe Tyr Arg Ile Pro Ala Leu Ala Thr Ala
        115                 120                 125

Ser Asn Gly Asp Leu Leu Ala Ser Tyr Asp Leu Arg Pro Gly Ser Ala
    130                 135                 140

Ala Asp Ala Pro Asn Pro Asn Ser Ile Val Gln Arg Arg Ser Arg Asp
145                 150                 155                 160

Asn Gly Arg Thr Arg Gly Pro Gln Thr Val Ile His Ala Gly Thr Leu
                165                 170                 175

Gly Arg Arg Lys Val Gly Tyr Ser Asp Pro Ser Tyr Leu Val Asp Pro
            180                 185                 190

Ala Thr Gly His Ile Leu Asn Phe His Val Lys Ser Tyr Asp Arg Gly
        195                 200                 205

Phe Ala Thr Ser Glu Val Gly Thr Asp Pro Asp Arg His Val Leu
    210                 215                 220

His Ala Glu Val Ser Thr Ser Asp Asn Gly His Thr Trp Thr Tyr
225                 230                 235                 240

Arg Asp Ile Thr Arg Glu Ile Thr Pro Asp Pro Thr Thr Arg Thr Arg
                245                 250                 255

Phe Val Ala Ser Gly Gln Gly Ile Ala Leu Leu His Gly Pro His Ala
            260                 265                 270
```

```
Gly Gly Leu Ile Ala Gln Met Thr Val Arg Asn Ser Val Gly Gln Gln
            275                 280                 285

Ala Gln Ser Ile Tyr Ser Asp His Gly Ile Thr Trp His Ala Gly
        290                 295                 300

Asn Pro Val Gly Arg Met Met Asp Glu Asn Lys Val Val Glu Leu Ser
305                 310                 315                 320

Asp Gly Thr Leu Met Leu Asn Ser Arg Asp Ala Ala Arg Ser Gly Arg
                325                 330                 335

Arg Lys Val Ala Tyr Ser His Asp Gly Leu Thr Trp Gly Pro Val
            340                 345                 350

Lys Leu Val Asp Asp Leu Ile Asp Pro Thr Asn Ala Gln Ile Ile
            355                 360                 365

Arg Ala Tyr Pro Asn Ala Arg Ala Gly Ser Ala Lys Ala Arg Ile Leu
        370                 375                 380

Leu Phe Thr Asn Ala Arg Asn Ala Thr Glu Arg Val Asn Gly Thr Leu
385                 390                 395                 400

Ser Val Ser Cys Asp Asp Gly Arg Thr Trp Val Ser His Gln Thr Tyr
                405                 410                 415

Met Pro Gly Glu Val Gly Tyr Thr Thr Ala Ala Val Gln Ser Asp Gly
            420                 425                 430

Ala Leu Gly Val Leu Trp Glu Arg Asp Gly Ile Arg Tyr Ser Thr Ile
        435                 440                 445

Pro Met Gly Trp Leu Asn Ser Val Cys Pro Val Ala Pro Ser Gly Arg
    450                 455                 460

Pro Thr Ser Gly Glu Pro Thr Ser Gly Thr Ser Leu Pro Leu Thr Ala
465                 470                 475                 480

Thr Pro Ser Gly Ser Leu His Gly Gly Ala Ser Ser Arg Pro Thr Ser
                485                 490                 495

Leu Pro His Thr Gly Asp
            500

<210> SEQ ID NO 14
<211> LENGTH: 1692
<212> TYPE: DNA
<213> ORGANISM: Propionibacterium acnes

<400> SEQUENCE: 14
tcaggacgcc agttcctgca ggtacatacg ttggagcccg tccgcccacg agtccgtagg    60
tgacgattcg aagagcacga gaacacgtcc gtcagacaac tgggcgatcg aggaataggc   120
gaagagggtc tgtgggctcg tgatgtcggc gtgactcacc cattcaagtt cggagcgcgg   180
tccgaacgtt ctcgaggatc gatggacaac tgccacatgg caatgccat gtcgacgcct    240 gcggtcatct gctgagacga caatgagcgc agggagctgt tccccggtcg taggtgatgc   300
gatggtttgc ttcagcatga gcgcggagac ttggcatgcg acgccttggt cgtcgtcgcc   360
gaacgcggaa gtcagcgtac tccaggaatg gccgccatcc acgctctcgg cggtcagcac   420
cttcccaccg gaagaagcgg aatgtcggtt gaagctgcgc aatacgccgg gtagaacctc   480
tgtgatcgcg ctttcgtgga ggtcgatagt ggctggcatc ggggttcccc gctgccacgt   540
ttccccacca tcgtcggtgt atacagtggt gcacgaaatt cctgcaggta gcatcatgta   600
agtcggaacg acgatgcgtc cggcatgttc ccctgcgcgg atttgaatgg accgacctgg   660
tgcgacgagc gtgtatcgag aatctacggg tctgaactgc cgtgtcacca gttttcccat   720
gttccaagtt cggccatcgt catatgagta gatctccacg atgtgattgg tgttgaagac   780
```

```
ctgaaggatc gagtccttgt agaagacgcg catcggagtg atgcgagctg aaccgtgctg    840
gaacacgtac agaggaattc ctgcttcgaa gaggttgaaa ccgtcgtcca aggagtatct    900
tgatcgtcgt cctagagcga gatttgagtc atcgactccg gcggtggtgt acgggcgagg    960
tataccgatt aattcataaa tctgaatgcg accgtgcttg tcgcggggc cgtcgaggtc     1020 agctacgagg tcgaattggg aacggtcgat gttcagattg atatttcccc tcaatccgtc    1080
ggcgtcccct gtgacgttgt gcgtcgagag caggagcatg tcacgtccgg caacggtggc    1140
gaagccatct cccaggggga actttcgcgg gcgcccaccg ttgacggggc catctgggga    1200
gacgttgagg tgttcgaata ctccgccgtt ccaggcccag agatcaatga cgatcatcag    1260
tcgatgtcga actgaatcct cgatgatggc gccgtcgatg acggaggatg atgcggggc     1320 gtacccatac ttgttcgaat aatctcgcat ctccaatggt tttatcagtg acggggcttc    1380
ccaaccgtcg gagattgagt aacgggatgc attgggtttt ctgcgaatca gggcatcgat    1440
attgtcggcg gagtcgcctg ttgtcgcgcg atttgcatcg cagcctatga ccaatgtgtc    1500
attggccgta gacaccatga acggtatgcg gaaaaaatgt gatggcgaat ctctctgtt    1560 gaacacctcg agtacgtctg cctcttgtgt cgcaagtgca ggagagtgtt cagagaactg    1620
ccctgtcaca ctcaagaata aggctgcccc gccagagatt aatgcggatc ggcgtgaaat    1680
ccgttggtgc at                                                        1692

<210> SEQ ID NO 15
<211> LENGTH: 563
<212> TYPE: PRT
<213> ORGANISM: Propionibacterium acnes

<400> SEQUENCE: 15

Met His Gln Arg Ile Ser Arg Arg Ser Ala Leu Ile Ser Gly Gly Ala
1               5                   10                  15

Ala Leu Phe Leu Ser Val Thr Gly Gln Phe Ser Glu His Ser Pro Ala
                20                  25                  30

Leu Ala Thr Gln Glu Ala Asp Val Leu Glu Val Phe Asn Arg Glu Asn
            35                  40                  45

Ser Pro Ser His Phe Phe Arg Ile Pro Phe Met Val Ser Thr Ala Asn
        50                  55                  60

Asp Thr Leu Val Ile Gly Cys Asp Ala Asn Arg Ala Thr Thr Gly Asp
65                  70                  75                  80

Ser Ala Asp Asn Ile Asp Ala Leu Ile Arg Arg Lys Pro Asn Ala Ser
                85                  90                  95

Arg Tyr Ser Ile Ser Asp Gly Trp Glu Ala Pro Ser Leu Ile Lys Pro
            100                 105                 110

Leu Glu Met Arg Asp Tyr Ser Asn Lys Tyr Gly Tyr Ala Pro Ala Ser
        115                 120                 125

Ser Ser Val Ile Asp Gly Ala Ile Ile Glu Asp Ser Val Arg His Arg
    130                 135                 140

Leu Met Ile Val Ile Asp Leu Trp Ala Trp Asn Gly Val Phe Glu
145                 150                 155                 160

His Leu Asn Val Ser Pro Asp Gly Pro Val Asn Gly Arg Pro Arg
                165                 170                 175

Lys Phe Pro Leu Gly Asp Gly Phe Ala Thr Val Ala Gly Arg Asp Met
            180                 185                 190

Leu Leu Leu Ser Thr His Asn Val Thr Gly Asp Ala Asp Gly Leu Arg
        195                 200                 205
```

Gly Asn Ile Asn Leu Asn Ile Asp Arg Ser Gln Phe Asp Leu Val Ala
    210                 215                 220

Asp Leu Asp Gly Pro Arg Asp Lys His Gly Arg Ile Gln Ile Tyr Glu
225                 230                 235                 240

Leu Ile Gly Ile Pro Arg Pro Tyr Thr Thr Ala Gly Val Asp Asp Ser
            245                 250                 255

Asn Leu Ala Leu Gly Arg Arg Ser Arg Tyr Ser Leu Asp Asp Gly Phe
        260                 265                 270

Asn Leu Phe Glu Ala Gly Ile Pro Leu Tyr Val Phe Gln His Gly Ser
    275                 280                 285

Ala Arg Ile Thr Pro Met Arg Val Phe Tyr Lys Asp Ser Ile Leu Gln
290                 295                 300

Val Phe Asn Thr Asn His Ile Val Glu Ile Tyr Ser Tyr Asp Asp Gly
305                 310                 315                 320

Arg Thr Trp Asn Met Gly Lys Leu Val Thr Arg Gln Phe Arg Pro Val
            325                 330                 335

Asp Ser Arg Tyr Thr Leu Val Ala Pro Gly Arg Ser Ile Gln Ile Arg
        340                 345                 350

Ala Gly Glu His Ala Gly Arg Ile Val Val Pro Thr Tyr Met Met Leu
    355                 360                 365

Pro Ala Gly Ile Ser Cys Thr Thr Val Tyr Thr Asp Asp Gly Gly Glu
370                 375                 380

Thr Trp Gln Arg Gly Thr Pro Met Pro Ala Thr Ile Asp Leu His Glu
385                 390                 395                 400

Ser Ala Ile Thr Glu Val Leu Pro Gly Val Leu Arg Ser Phe Asn Arg
            405                 410                 415

His Ser Ala Ser Ser Gly Gly Lys Val Leu Thr Ala Glu Ser Val Asp
        420                 425                 430

Gly Gly His Ser Trp Ser Thr Leu Thr Ser Ala Phe Gly Asp Asp Asp
    435                 440                 445

Gln Gly Val Ala Cys Gln Val Ser Ala Leu Met Leu Lys Gln Thr Ile
450                 455                 460

Ala Ser Pro Thr Thr Gly Glu Gln Leu Pro Ala Leu Ile Val Val Ser
465                 470                 475                 480

Ala Asp Asp Arg Arg Arg His Gly Ile Ala His Val Ala Val Val
            485                 490                 495

His Arg Ser Ser Arg Thr Phe Gly Pro Arg Ser Glu Leu Glu Trp Val
        500                 505                 510

Ser His Ala Asp Ile Thr Ser Pro Gln Thr Leu Phe Ala Tyr Ser Ser
    515                 520                 525

Ile Ala Gln Leu Ser Asp Gly Arg Val Leu Val Leu Phe Glu Ser Ser
530                 535                 540

Pro Thr Asp Ser Trp Ala Asp Gly Leu Gln Arg Met Tyr Leu Gln Glu
545                 550                 555                 560

Leu Ala Ser

<210> SEQ ID NO 16
<211> LENGTH: 3966
<212> TYPE: DNA
<213> ORGANISM: Propionibacterium acnes
<220> FEATURE:
<221> NAME/KEY: CDS
<222> LOCATION: (1)..(3966)

<400> SEQUENCE: 16

```
atg tcg cga aca cca cgg ggc agg tcc atc ggt gcg ctc gcc gtg tca      48
Met Ser Arg Thr Pro Arg Gly Arg Ser Ile Gly Ala Leu Ala Val Ser
1               5                   10                  15 gct ggc acg atg ctg gca ctg atc gcg ccg acg gcc cct gca cat gcc      96
Ala Gly Thr Met Leu Ala Leu Ile Ala Pro Thr Ala Pro Ala His Ala
                20                  25                  30 gag acc cgg tac cgc cag att aac cag gca gca atc acc gcg gtt gcc     144
Glu Thr Arg Tyr Arg Gln Ile Asn Gln Ala Ala Ile Thr Ala Val Ala
            35                  40                  45 gct gat tca gcc acc gcc acc gat ccg atc tcc aac act ctg gac ggc     192
Ala Asp Ser Ala Thr Ala Thr Asp Pro Ile Ser Asn Thr Leu Asp Gly
        50                  55                  60 aat ccc gac acg atc tgg cac acc aca tgg cag aac gga aag gac ccg     240
Asn Pro Asp Thr Ile Trp His Thr Thr Trp Gln Asn Gly Lys Asp Pro
65                  70                  75                  80 cta cct cac tgg atc gta ttc aaa cta ggt gat gag gcc gtg aac ctg     288
Leu Pro His Trp Ile Val Phe Lys Leu Gly Asp Glu Ala Val Asn Leu
                85                  90                  95 ggc aag gtg gaa atc aca ccc aga tcc agc tcg aac ggc tcg ggt cgc     336
Gly Lys Val Glu Ile Thr Pro Arg Ser Ser Ser Asn Gly Ser Gly Arg
            100                 105                 110 atg cac gac tac gag cta tac acg gcc aac acc aag acc tgc aac aac     384
Met His Asp Tyr Glu Leu Tyr Thr Ala Asn Thr Lys Thr Cys Asn Asn
        115                 120                 125 gcc gca ttc tcc tca gcg aag ccg gtt gca acg ggt tct tac gga gcc     432
Ala Ala Phe Ser Ser Ala Lys Pro Val Ala Thr Gly Ser Tyr Gly Ala
    130                 135                 140 tcc gac acg tcg ata cgc aag atc acc ttc gcc gca acc aag gcc acc     480
Ser Asp Thr Ser Ile Arg Lys Ile Thr Phe Ala Ala Thr Lys Ala Thr
145                 150                 155                 160 tgc gtc aaa gtg aag gtg aac tcc tct tgg gga ggc gac gga tcg gac     528
Cys Val Lys Val Lys Val Asn Ser Ser Trp Gly Gly Asp Gly Ser Asp
                165                 170                 175 gag gaa gtc tcc tcg atg gcg gaa ttc aat gcc ttc acc gtc gac gga     576
Glu Glu Val Ser Ser Met Ala Glu Phe Asn Ala Phe Thr Val Asp Gly
            180                 185                 190 tcg gac cct tct ccg gat ccc aca cca tcg gaa ccg ccg acc cca gag     624
Ser Asp Pro Ser Pro Asp Pro Thr Pro Ser Glu Pro Pro Thr Pro Glu
        195                 200                 205 gtc ccg aaa gac gcc atc agc ctg tcc gac ggc act gtg acg gtc agg     672
Val Pro Lys Asp Ala Ile Ser Leu Ser Asp Gly Thr Val Thr Val Arg
    210                 215                 220 gcc cgt cgt gac ttc ccg caa gtg atc gac tac acc gtc ggc cac gca     720
Ala Arg Arg Asp Phe Pro Gln Val Ile Asp Tyr Thr Val Gly His Ala
225                 230                 235                 240 cac atg gca gga cgt atc ggc tcc ccg ttg acg aag gtc agg atc aac     768
His Met Ala Gly Arg Ile Gly Ser Pro Leu Thr Lys Val Arg Ile Asn
                245                 250                 255 ggc gcc gac cac gtc gcc act gtg tcc gcg ccc acg acg act ggc tcc     816
Gly Ala Asp His Val Ala Thr Val Ser Ala Pro Thr Thr Thr Gly Ser
            260                 265                 270 tcc gcg tcc tgg aag ctc acc ttc cgc gac ctg ccc ggc gtc gag ctc     864
Ser Ala Ser Trp Lys Leu Thr Phe Arg Asp Leu Pro Gly Val Glu Leu
        275                 280                 285 act gca gac atc aag gtc tcc gat ggt gtc atg aca tgg tcg atc cca     912
Thr Ala Asp Ile Lys Val Ser Asp Gly Val Met Thr Trp Ser Ile Pro
    290                 295                 300 cac atc gtc gac acc cct gac cac cgt gtc aac acc gtg tca gtg ccc     960
His Ile Val Asp Thr Pro Asp His Arg Val Asn Thr Val Ser Val Pro
```

```
                 305                 310                 315                 320
ggc ctc act ctc gcc tcg gtc acc tcg act gat ccg aaa gcc cag ctg      1008
Gly Leu Thr Leu Ala Ser Val Thr Ser Thr Asp Pro Lys Ala Gln Leu
            325                 330                 335 agc agc gca aac att gtc gtc gat cgc aac aag acc ggc gac ctc ttc      1056
Ser Ser Ala Asn Ile Val Val Asp Arg Asn Lys Thr Gly Asp Leu Phe
            340                 345                 350 cag ccc ctc gcc acc gct gac gtc tcg cag gac acc tcc tgg gtc gcc      1104
Gln Pro Leu Ala Thr Ala Asp Val Ser Gln Asp Thr Ser Trp Val Ala
            355                 360                 365 atg gcg aac gat tcc acg ctg gca gcc ggg ttc gag gac aac gca acc      1152
Met Ala Asn Asp Ser Thr Leu Ala Ala Gly Phe Glu Asp Asn Ala Thr
            370                 375                 380 cag gac ggc ctg gtc ggc tcc gcc gcc acg gtt gcc cgt ttc gtc cac      1200
Gln Asp Gly Leu Val Gly Ser Ala Ala Thr Val Ala Arg Phe Val His
385                 390                 395                 400 tcc atc tcc cag gtt ggg ggg act aag gtc gga gcc atc gaa ccg gca      1248
Ser Ile Ser Gln Val Gly Gly Thr Lys Val Gly Ala Ile Glu Pro Ala
            405                 410                 415 acc tgg gtc cat cgt ggc aag ggg tcc gcc acc ccc ttc ccc acc gac      1296
Thr Trp Val His Arg Gly Lys Gly Ser Ala Thr Pro Phe Pro Thr Asp
            420                 425                 430 tca ctc ggc aac aag gcc gta tgc cag ctg ccc ggt ggt gcc act gtc      1344
Ser Leu Gly Asn Lys Ala Val Cys Gln Leu Pro Gly Gly Ala Thr Val
            435                 440                 445 aag gac ggc atc ggc cca gac ccc gac acc ccg tac gtc cgg gtg aag      1392
Lys Asp Gly Ile Gly Pro Asp Pro Asp Thr Pro Tyr Val Arg Val Lys
            450                 455                 460 atc gtc gct gac gcc aat gcc gac ggc aag gtc gac tgg cag gac gca      1440
Ile Val Ala Asp Ala Asn Ala Asp Gly Lys Val Asp Trp Gln Asp Ala
465                 470                 475                 480 gcc gtc gcc acc cgg gac gtc acc atg aag ccg acc ggc tcg ggg gac      1488
Ala Val Ala Thr Arg Asp Val Thr Met Lys Pro Thr Gly Ser Gly Asp
                485                 490                 495 gtg gcg aac aag gtc atc acc cat att ccg ttt aac atc gtc tcc cag      1536
Val Ala Asn Lys Val Ile Thr His Ile Pro Phe Asn Ile Val Ser Gln
            500                 505                 510 gcg act cat ccg ttc ctt cgt acc ttg gac gat gtc aag cgc atc tct      1584
Ala Thr His Pro Phe Leu Arg Thr Leu Asp Asp Val Lys Arg Ile Ser
            515                 520                 525 ttg gcg acc gac ggg ctc ggc cag cag gcc ctg ctc aag ggc tac cag      1632
Leu Ala Thr Asp Gly Leu Gly Gln Gln Ala Leu Leu Lys Gly Tyr Gln
            530                 535                 540 gcc gag ggc cac gac tcc gca cac ccc gac tac ggc ggc aac gtc tcc      1680
Ala Glu Gly His Asp Ser Ala His Pro Asp Tyr Gly Gly Asn Val Ser
545                 550                 555                 560 cac cgt gcc ggc ggg atg aag gat ctc gag aag ctc acc gag tcg ggc      1728
His Arg Ala Gly Gly Met Lys Asp Leu Glu Lys Leu Thr Glu Ser Gly
                565                 570                 575 agg cag tgg aac acc gat ttc ggc att cac gtc aac ctg gtg gag tct      1776
Arg Gln Trp Asn Thr Asp Phe Gly Ile His Val Asn Leu Val Glu Ser
            580                 585                 590 tac cct gag gcg aat cac ttc ggc gac aac atc ctc gtt aag ccg tac      1824
Tyr Pro Glu Ala Asn His Phe Gly Asp Asn Ile Leu Val Lys Pro Tyr
            595                 600                 605 cag aag gcg tgg gac tgg atg gag cag tcc tac cgg atg gac tac gcc      1872
Gln Lys Ala Trp Asp Trp Met Glu Gln Ser Tyr Arg Met Asp Tyr Ala
            610                 615                 620 aag gac ctt ggg tct ggt cag ctc ttc gct cga ctc aac cag ctg agg      1920
```

```
                                           -continued
Lys Asp Leu Gly Ser Gly Gln Leu Phe Ala Arg Leu Asn Gln Leu Arg
625                 630                 635                 640 aag gag ttg gga gcc aag tcc aac ctc gac tgg ttg tac ttc gac acc        1968
Lys Glu Leu Gly Ala Lys Ser Asn Leu Asp Trp Leu Tyr Phe Asp Thr
                645                 650                 655 aac tac cct gct ggt tgg cag aac gac cgg atc gcc aac gct ctg aac        2016
Asn Tyr Pro Ala Gly Trp Gln Asn Asp Arg Ile Ala Asn Ala Leu Asn
        660                 665                 670 gcc gaa ggc tgg agg atc ggt tcc gaa tgg tcg tca acc tat ccg cgc        2064
Ala Glu Gly Trp Arg Ile Gly Ser Glu Trp Ser Ser Thr Tyr Pro Arg
    675                 680                 685 tat aac cag tgg tcg cac tgg gcc aat gac gag aac tac gga acc gga        2112
Tyr Asn Gln Trp Ser His Trp Ala Asn Asp Glu Asn Tyr Gly Thr Gly
690                 695                 700 aac aag gga tac agt tcc cgg atc att cgg ttc atc gac aac tcc cgc        2160
Asn Lys Gly Tyr Ser Ser Arg Ile Ile Arg Phe Ile Asp Asn Ser Arg
705                 710                 715                 720 cgc gac act tgg aat cct gat ccg atc ctc ggc aac tcc aat gtc gtc        2208
Arg Asp Thr Trp Asn Pro Asp Pro Ile Leu Gly Asn Ser Asn Val Val
                725                 730                 735 gag tat gag ggt tgg acg agc cac aac gac tac aac gcg ttc atc gcg        2256
Glu Tyr Glu Gly Trp Thr Ser His Asn Asp Tyr Asn Ala Phe Ile Ala
            740                 745                 750 aat gtg tgg cag cgc aac ctg cct acc aag ttc tta cag cgt tcg gac        2304
Asn Val Trp Gln Arg Asn Leu Pro Thr Lys Phe Leu Gln Arg Ser Asp
        755                 760                 765 atc atg tct tgg caa gac ggc cgt atc gct ttc gct aac gga gcc gtg        2352
Ile Met Ser Trp Gln Asp Gly Arg Ile Ala Phe Ala Asn Gly Ala Val
    770                 775                 780 gca act tcg tcg aag aag tcc atc tcg ggt cat gag att ccc acc gca        2400
Ala Thr Ser Ser Lys Lys Ser Ile Ser Gly His Glu Ile Pro Thr Ala
785                 790                 795                 800 aga acc atc acc ttt gac ggt gcc acg gtc ttc aag gaa ggc ggg tcc        2448
Arg Thr Ile Thr Phe Asp Gly Ala Thr Val Phe Lys Glu Gly Gly Ser
                805                 810                 815 tac ctg ctc cca tgg tct aac ggt ggc agc gat cgc ctg tac tac tgg        2496
Tyr Leu Leu Pro Trp Ser Asn Gly Gly Ser Asp Arg Leu Tyr Tyr Trp
            820                 825                 830 aat ccg ggc aat ggc tca gca act tgg aaa ctc acg aat tcc tgg gcg        2544
Asn Pro Gly Asn Gly Ser Ala Thr Trp Lys Leu Thr Asn Ser Trp Ala
        835                 840                 845 gca cag aaa tcg gta tct ctg ttc atg ctc acc gac acc ggc cgt gtc        2592
Ala Gln Lys Ser Val Ser Leu Phe Met Leu Thr Asp Thr Gly Arg Val
    850                 855                 860 aag gtt gcc gaa atc ccc gtc acc aac agg tcc atc agg att ccc gca        2640
Lys Val Ala Glu Ile Pro Val Thr Asn Arg Ser Ile Arg Ile Pro Ala
865                 870                 875                 880 acc aag gcc aag act gcc tac gtc ctc tac ccg acg tct aag gtg cct        2688
Thr Lys Ala Lys Thr Ala Tyr Val Leu Tyr Pro Thr Ser Lys Val Pro
                885                 890                 895 gct gca aaa acc ccg aac tgg gga gag gga agt cac ttc gcc aat ccg        2736
Ala Ala Lys Thr Pro Asn Trp Gly Glu Gly Ser His Phe Ala Asn Pro
            900                 905                 910 ggc ttc tac tcc ggt gac acc gct ggt tgg aat gcc cgg gga aac gtc        2784
Gly Phe Tyr Ser Gly Asp Thr Ala Gly Trp Asn Ala Arg Gly Asn Val
        915                 920                 925 tcg gtc aag cac aac gac cgt ggc aac ttc cac ctc gag ttc ggc aag        2832
Ser Val Lys His Asn Asp Arg Gly Asn Phe His Leu Glu Phe Gly Lys
    930                 935                 940
```

```
                                  -continued gca cag tcg cag atc tcc caa gtc ctc aat ctg cct gct ggt gac cac      2880
Ala Gln Ser Gln Ile Ser Gln Val Leu Asn Leu Pro Ala Gly Asp His
945                 950                 955                 960 tcc ctg tgg gcg tgg gtc cag ata gat ccg act aag acc cgt cca gtg      2928
Ser Leu Trp Ala Trp Val Gln Ile Asp Pro Thr Lys Thr Arg Pro Val
            965                 970                 975 gga ctt gcc gtc gac ggc acc ggg gtc act ccc atc gac cat cag aag      2976
Gly Leu Ala Val Asp Gly Thr Gly Val Thr Pro Ile Asp His Gln Lys
        980                 985                 990 gga tgc ggg ggc cac gcg gaa tcc gtc atc acg tcc acg aca gcc atc      3024
Gly Cys Gly Gly His Ala Glu Ser Val Ile Thr Ser Thr Thr Ala Ile
    995                 1000                1005 aac gcc acc gct tcc gac gag tat ttc ggc acc tac cac cag cgg          3069
Asn Ala Thr Ala Ser Asp Glu Tyr Phe Gly Thr Tyr His Gln Arg
1010                1015                1020 ctg cga gtt gct ttc cac tct gac ggc aga cca gtc acc gtt acc          3114
Leu Arg Val Ala Phe His Ser Asp Gly Arg Pro Val Thr Val Thr
1025                1030                1035 ttg aag gcg ctc gcc ggg aat gct atc gtc agc gcc gat gac ttc          3159
Leu Lys Ala Leu Ala Gly Asn Ala Ile Val Ser Ala Asp Asp Phe
1040                1045                1050 cga gtc gtt gac gct gct gtg ccc agc gac cct cac gtc acg cct          3204
Arg Val Val Asp Ala Ala Val Pro Ser Asp Pro His Val Thr Pro
1055                1060                1065 gcg acc gtt ctt ttc cag aac ttc gag gac gtc gac acc ggt tac          3249
Ala Thr Val Leu Phe Gln Asn Phe Glu Asp Val Asp Thr Gly Tyr
1070                1075                1080 tgg ccc ttc gtc acg gga agc gca ggc atg gag gga gat gcc cgg          3294
Trp Pro Phe Val Thr Gly Ser Ala Gly Met Glu Gly Asp Ala Arg
1085                1090                1095 acc cag tta tcc cgt cgc cat gag cct tac acc cag aaa ggt tgg          3339
Thr Gln Leu Ser Arg Arg His Glu Pro Tyr Thr Gln Lys Gly Trp
1100                1105                1110 aac ggt cgg gcc atg gac tcg gtt ctc agc ggt gac tgg tcc ttg          3384
Asn Gly Arg Ala Met Asp Ser Val Leu Ser Gly Asp Trp Ser Leu
1115                1120                1125 aag atg cac gaa gaa cgc aac ggg atc gtg ctg cgc acg acc acc          3429
Lys Met His Glu Glu Arg Asn Gly Ile Val Leu Arg Thr Thr Thr
1130                1135                1140 gcg tcc gcc cct ctg acc ggg ggc gga acc cgg tac cgc atc tcc          3474
Ala Ser Ala Pro Leu Thr Gly Gly Gly Thr Arg Tyr Arg Ile Ser
1145                1150                1155 ttc gac tac cag gct gac aaa ccc ggg tac tcg ttc gtc aca ggt          3519
Phe Asp Tyr Gln Ala Asp Lys Pro Gly Tyr Ser Phe Val Thr Gly
1160                1165                1170 cac gac aag gtc agc gga aag tcc gtc aag gaa gtc atc acc gag          3564
His Asp Lys Val Ser Gly Lys Ser Val Lys Glu Val Ile Thr Glu
1175                1180                1185 tcc cat gcc atg gga gtc gcc acc tcg acg act cat ttc tcc acc          3609
Ser His Ala Met Gly Val Ala Thr Ser Thr Thr His Phe Ser Thr
1190                1195                1200 gac atc gtt gtg aag gac caa cct gcc tgg atc gga ttc acc cac          3654
Asp Ile Val Val Lys Asp Gln Pro Ala Trp Ile Gly Phe Thr His
1205                1210                1215 cag ggt gaa ggg gat atg tcc atc gac aac ctg cgc atc gaa aag          3699
Gln Gly Glu Gly Asp Met Ser Ile Asp Asn Leu Arg Ile Glu Lys
1220                1225                1230 ctc gat cca cga ccg atc tcc gtc acc tcc acg cag gca gcg gtg          3744
Leu Asp Pro Arg Pro Ile Ser Val Thr Ser Thr Gln Ala Ala Val
1235                1240                1245
```

```
ttc ccg gat gcc tgc aag ccg acc ccc gaa ccg atc caa ccg gcg      3789
Phe Pro Asp Ala Cys Lys Pro Thr Pro Glu Pro Ile Gln Pro Ala
    1250                1255                1260 caa ccc tcg gct tcc gct ccg acg aca tcc ggc tcc ccc caa gcc      3834
Gln Pro Ser Ala Ser Ala Pro Thr Thr Ser Gly Ser Pro Gln Ala
1265                1270                1275 cct gga acc ggt aac cgc ccc aac cgt tat gcc ttg cct cgt acc      3879
Pro Gly Thr Gly Asn Arg Pro Asn Arg Tyr Ala Leu Pro Arg Thr
        1280                1285                1290 gga gca gac ggc gcc ggg ctc ggc ttc agc agt tcc gag gcg gca      3924
Gly Ala Asp Gly Ala Gly Leu Gly Phe Ser Ser Ser Glu Ala Ala
    1295                1300                1305 tcg gca aca gct gct gtg ggt gtc tcc cgt caa ggc cga tga           3966
Ser Ala Thr Ala Ala Val Gly Val Ser Arg Gln Gly Arg
1310                1315                1320
```

<210> SEQ ID NO 17
<211> LENGTH: 1321
<212> TYPE: PRT
<213> ORGANISM: Propionibacterium acnes

<400> SEQUENCE: 17

```
Met Ser Arg Thr Pro Arg Gly Arg Ser Ile Gly Ala Leu Ala Val Ser
1               5                   10                  15

Ala Gly Thr Met Leu Ala Leu Ile Ala Pro Thr Ala Pro Ala His Ala
            20                  25                  30

Glu Thr Arg Tyr Arg Gln Ile Asn Gln Ala Ala Ile Thr Ala Val Ala
        35                  40                  45

Ala Asp Ser Ala Thr Ala Thr Asp Pro Ile Ser Asn Thr Leu Asp Gly
    50                  55                  60

Asn Pro Asp Thr Ile Trp His Thr Thr Trp Gln Asn Gly Lys Asp Pro
65                  70                  75                  80

Leu Pro His Trp Ile Val Phe Lys Leu Gly Asp Glu Ala Val Asn Leu
                85                  90                  95

Gly Lys Val Glu Ile Thr Pro Arg Ser Ser Asn Gly Ser Gly Arg
            100                 105                 110

Met His Asp Tyr Glu Leu Tyr Thr Ala Asn Thr Lys Thr Cys Asn Asn
        115                 120                 125

Ala Ala Phe Ser Ser Ala Lys Pro Val Ala Thr Gly Ser Tyr Gly Ala
    130                 135                 140

Ser Asp Thr Ser Ile Arg Lys Ile Thr Phe Ala Ala Thr Lys Ala Thr
145                 150                 155                 160

Cys Val Lys Val Lys Val Asn Ser Ser Trp Gly Gly Asp Gly Ser Asp
                165                 170                 175

Glu Glu Val Ser Ser Met Ala Glu Phe Asn Ala Phe Thr Val Asp Gly
            180                 185                 190

Ser Asp Pro Ser Pro Asp Pro Thr Pro Ser Glu Pro Pro Thr Pro Glu
        195                 200                 205

Val Pro Lys Asp Ala Ile Ser Leu Ser Asp Gly Thr Val Thr Val Arg
    210                 215                 220

Ala Arg Arg Asp Phe Pro Gln Val Ile Asp Tyr Thr Val Gly His Ala
225                 230                 235                 240

His Met Ala Gly Arg Ile Gly Ser Pro Leu Thr Lys Val Arg Ile Asn
                245                 250                 255

Gly Ala Asp His Val Ala Thr Val Ser Ala Pro Thr Thr Gly Ser
            260                 265                 270
```

```
Ser Ala Ser Trp Lys Leu Thr Phe Arg Asp Leu Pro Gly Val Glu Leu
        275                 280                 285

Thr Ala Asp Ile Lys Val Ser Asp Gly Val Met Thr Trp Ser Ile Pro
    290                 295                 300

His Ile Val Asp Thr Pro Asp His Arg Val Asn Thr Val Ser Val Pro
305                 310                 315                 320

Gly Leu Thr Leu Ala Ser Val Thr Ser Thr Asp Pro Lys Ala Gln Leu
                325                 330                 335

Ser Ser Ala Asn Ile Val Val Asp Arg Asn Lys Thr Gly Asp Leu Phe
            340                 345                 350

Gln Pro Leu Ala Thr Ala Asp Val Ser Gln Asp Thr Ser Trp Val Ala
        355                 360                 365

Met Ala Asn Asp Ser Thr Leu Ala Ala Gly Phe Glu Asp Asn Ala Thr
    370                 375                 380

Gln Asp Gly Leu Val Gly Ser Ala Ala Thr Val Ala Arg Phe Val His
385                 390                 395                 400

Ser Ile Ser Gln Val Gly Gly Thr Lys Val Gly Ala Ile Glu Pro Ala
                405                 410                 415

Thr Trp Val His Arg Gly Lys Gly Ser Ala Thr Pro Phe Pro Thr Asp
            420                 425                 430

Ser Leu Gly Asn Lys Ala Val Cys Gln Leu Pro Gly Gly Ala Thr Val
        435                 440                 445

Lys Asp Gly Ile Gly Pro Asp Pro Asp Thr Pro Tyr Val Arg Val Lys
    450                 455                 460

Ile Val Ala Asp Ala Asn Ala Asp Gly Lys Val Asp Trp Gln Asp Ala
465                 470                 475                 480

Ala Val Ala Thr Arg Asp Val Thr Met Lys Pro Thr Gly Ser Gly Asp
                485                 490                 495

Val Ala Asn Lys Val Ile Thr His Ile Pro Phe Asn Ile Val Ser Gln
            500                 505                 510

Ala Thr His Pro Phe Leu Arg Thr Leu Asp Asp Val Lys Arg Ile Ser
        515                 520                 525

Leu Ala Thr Asp Gly Leu Gly Gln Gln Ala Leu Leu Lys Gly Tyr Gln
    530                 535                 540

Ala Glu Gly His Asp Ser Ala His Pro Asp Tyr Gly Gly Asn Val Ser
545                 550                 555                 560

His Arg Ala Gly Gly Met Lys Asp Leu Glu Lys Leu Thr Glu Ser Gly
                565                 570                 575

Arg Gln Trp Asn Thr Asp Phe Gly Ile His Val Asn Leu Val Glu Ser
            580                 585                 590

Tyr Pro Glu Ala Asn His Phe Gly Asp Asn Ile Leu Val Lys Pro Tyr
        595                 600                 605

Gln Lys Ala Trp Asp Trp Met Glu Gln Ser Tyr Arg Met Asp Tyr Ala
    610                 615                 620

Lys Asp Leu Gly Ser Gly Gln Leu Phe Ala Leu Asn Gln Leu Arg
625                 630                 635                 640

Lys Glu Leu Gly Ala Lys Ser Asn Leu Asp Trp Leu Tyr Phe Asp Thr
                645                 650                 655

Asn Tyr Pro Ala Gly Trp Gln Asn Asp Arg Ile Ala Asn Ala Leu Asn
            660                 665                 670

Ala Glu Gly Trp Arg Ile Gly Ser Glu Trp Ser Ser Thr Tyr Pro Arg
        675                 680                 685
```

```
Tyr Asn Gln Trp Ser His Trp Ala Asn Asp Glu Asn Tyr Gly Thr Gly
    690             695             700
Asn Lys Gly Tyr Ser Ser Arg Ile Ile Arg Phe Ile Asp Asn Ser Arg
705             710             715             720
Arg Asp Thr Trp Asn Pro Asp Pro Ile Leu Gly Asn Ser Asn Val Val
                725             730             735
Glu Tyr Glu Gly Trp Thr Ser His Asn Asp Tyr Asn Ala Phe Ile Ala
            740             745             750
Asn Val Trp Gln Arg Asn Leu Pro Thr Lys Phe Leu Gln Arg Ser Asp
        755             760             765
Ile Met Ser Trp Gln Asp Gly Arg Ile Ala Phe Ala Asn Gly Ala Val
770             775             780
Ala Thr Ser Ser Lys Lys Ser Ile Ser Gly His Glu Ile Pro Thr Ala
785             790             795             800
Arg Thr Ile Thr Phe Asp Gly Ala Thr Val Phe Lys Glu Gly Ser
                805             810             815
Tyr Leu Leu Pro Trp Ser Asn Gly Gly Ser Asp Arg Leu Tyr Tyr Trp
            820             825             830
Asn Pro Gly Asn Gly Ser Ala Thr Trp Lys Leu Thr Asn Ser Trp Ala
        835             840             845
Ala Gln Lys Ser Val Ser Leu Phe Met Leu Thr Asp Thr Gly Arg Val
850             855             860
Lys Val Ala Glu Ile Pro Val Thr Asn Arg Ser Ile Arg Ile Pro Ala
865             870             875             880
Thr Lys Ala Lys Thr Ala Tyr Val Leu Tyr Pro Thr Ser Lys Val Pro
                885             890             895
Ala Ala Lys Thr Pro Asn Trp Gly Glu Gly Ser His Phe Ala Asn Pro
            900             905             910
Gly Phe Tyr Ser Gly Asp Thr Ala Gly Trp Asn Ala Arg Gly Asn Val
        915             920             925
Ser Val Lys His Asn Asp Arg Gly Asn Phe His Leu Glu Phe Gly Lys
930             935             940
Ala Gln Ser Gln Ile Ser Gln Val Leu Asn Leu Pro Ala Gly Asp His
945             950             955             960
Ser Leu Trp Ala Trp Val Gln Ile Asp Pro Thr Lys Thr Arg Pro Val
                965             970             975
Gly Leu Ala Val Asp Gly Thr Gly Val Thr Pro Ile Asp His Gln Lys
            980             985             990
Gly Cys Gly Gly His Ala Glu Ser Val Ile Thr Ser Thr Ala Ile
        995             1000            1005
Asn Ala Thr Ala Ser Asp Glu Tyr Phe Gly Thr Tyr His Gln Arg
    1010            1015            1020
Leu Arg Val Ala Phe His Ser Asp Gly Arg Pro Val Thr Val Thr
    1025            1030            1035
Leu Lys Ala Leu Ala Gly Asn Ala Ile Val Ser Ala Asp Asp Phe
    1040            1045            1050
Arg Val Val Asp Ala Ala Val Pro Ser Asp Pro His Val Thr Pro
    1055            1060            1065
Ala Thr Val Leu Phe Gln Asn Phe Glu Asp Val Asp Thr Gly Tyr
    1070            1075            1080
Trp Pro Phe Val Thr Gly Ser Ala Gly Met Glu Gly Asp Ala Arg
    1085            1090            1095
Thr Gln Leu Ser Arg Arg His Glu Pro Tyr Thr Gln Lys Gly Trp
```

```
              1100                1105                1110

Asn Gly Arg Ala Met Asp Ser Val Leu Ser Gly Asp Trp Ser Leu
      1115                1120                1125

Lys Met His Glu Glu Arg Asn Gly Ile Val Leu Arg Thr Thr Thr
      1130                1135                1140

Ala Ser Ala Pro Leu Thr Gly Gly Thr Arg Tyr Arg Ile Ser
      1145                1150                1155

Phe Asp Tyr Gln Ala Asp Lys Pro Gly Tyr Ser Phe Val Thr Gly
      1160                1165                1170

His Asp Lys Val Ser Gly Lys Ser Val Lys Glu Val Ile Thr Glu
      1175                1180                1185

Ser His Ala Met Gly Val Ala Thr Ser Thr Thr His Phe Ser Thr
      1190                1195                1200

Asp Ile Val Val Lys Asp Gln Pro Ala Trp Ile Gly Phe Thr His
      1205                1210                1215

Gln Gly Glu Gly Asp Met Ser Ile Asp Asn Leu Arg Ile Glu Lys
      1220                1225                1230

Leu Asp Pro Arg Pro Ile Ser Val Thr Ser Thr Gln Ala Ala Val
      1235                1240                1245

Phe Pro Asp Ala Cys Lys Pro Thr Pro Glu Pro Ile Gln Pro Ala
      1250                1255                1260

Gln Pro Ser Ala Ser Ala Pro Thr Thr Ser Gly Ser Pro Gln Ala
      1265                1270                1275

Pro Gly Thr Gly Asn Arg Pro Asn Arg Tyr Ala Leu Pro Arg Thr
      1280                1285                1290

Gly Ala Asp Gly Ala Gly Leu Gly Phe Ser Ser Ser Glu Ala Ala
      1295                1300                1305

Ser Ala Thr Ala Ala Val Gly Val Ser Arg Gln Gly Arg
      1310                1315                1320

<210> SEQ ID NO 18
<211> LENGTH: 35
<212> TYPE: DNA
<213> ORGANISM: Artificial Sequence
<220> FEATURE:
<223> OTHER INFORMATION: Oligonucleotide Primer

<400> SEQUENCE: 18
ccttctagag gagatatacc atgggtcata atcat                35

<210> SEQ ID NO 19
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 19
tcccccgggt taattaatta agcggccgcc              30

<210> SEQ ID NO 20
<211> LENGTH: 34
<212> TYPE: DNA
<213> ORGANISM: Artificial Sequence
<220> FEATURE:
<223> OTHER INFORMATION: Oligonucleotide Primer

<400> SEQUENCE: 20
agatctagaa tgtctggttc tcatcatcat catc              34
```

```
<210> SEQ ID NO 21
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 21 gccccgggt tagccttcga tcccgaggtt                                30
```

METHODS AND COMPOSITIONS FOR TREATING *P. ACNES*

CROSS REFERENCE TO RELATED APPLICATIONS

This application is a U.S. National Stage Application filed under 35 U.S.C. §371 and claims priority to International Application No. PCT/US09/66577, filed Dec. 3, 2009, which application claims priority from U.S. Provisional Application Ser. No. 61/120,221, filed Dec. 5, 2008, which is are incorporated herein by reference.

TECHNICAL FIELD

The disclosure relates generally to an antigenic composition useful for immunization against *P. acnes*. The disclosure is a method for producing a vaccine for preventing *P. acnes* associated diseases and disorders including rosceacea in humans and animals, a vaccine against *P. acnes* in humans and animals, and an approach to producing vaccines against *P. acnes*.

BACKGROUND

As a member of the resident human microflora, the Gram-positive anaerobic coryneform bacterium *Propionibacterium acnes* (*P. acnes*) is found predominantly in the sebaceous gland of the skin. It can, however, also be isolated from the conjunctiva, the external ear canal, the mouth, the upper respiratory tract and, in some individuals, the intestine. *P. acnes* has an estimated skin density of $10^2$ to $10^{5-6}$ cm$^{-2}$. *P. acnes* is a well-recognized opportunistic pathogen, especially in relation to medical implants such as central nervous system shunts, silicone implants and prosthetic hip joints. It is also responsible for ocular and periocular infections and endophthalmitis and has been implicated in periodontal and dental infections. Dental probing and treatment has lead to the dissemination of *P. acnes* in the bloodstream, which is a recognized cause of endocarditis in relation to damaged or prosthetic heart valves. *P. acnes* also plays a role in inflammatory acne, since antimicrobial therapy directed against *P. acnes* results in improvement, while the development of antibiotic resistance in *P. acnes* is associated with relapse. The common form of acne, known as acne vulgaris, affects up to 80% of the population at some time in their lives, making it the most common skin infection. There is also a strong association between severe forms of acne and joint pain, inflammation of the bone (osteitis) and arthritis. In patients suffering from this condition, known as SAPHO (synovitis, acne, pustulosis, hyperostosis and osteitis) syndrome, isolates of *P. acnes* have been recovered from bone biopsy samples, as well as synovial fluid and tissue.

Two distinct phenotypes of *P. acnes*, types I and II, have been identified based on serological agglutination tests and cell-wall sugar analysis. Recently, recA-based sequence analysis has revealed that *P. acnes* types I and II represent phylogenetically distinct groups (McDowell et al., 2005).

*P. acnes* produces a co-haemolytic reaction with both sheep and human erythrocytes (Choudhury, 1978) similar to the Christie-Atkins-Munch-Petersen (CAMP) reaction first demonstrated in 1944 (Christie et al., 1944). The CAMP reaction describes the synergistic haemolysis of sheep erythrocytes by the CAMP factor from *Streptococcus agalactiae* and the toxin (sphingomyelinase C) from *Staphylococcus aureus*, with the CAMP factor demonstrating non-enzymic affinity for ceramide (Bernheimer et al., 1979). Examination of sphingomyelinase-treated sheep erythrocytes has revealed the formation of discrete membrane pores by recombinant *Streptococcus agalactiae* CAMP factor (Lang & Palmer, 2003). In addition to the extensive study of the CAMP factor of *Streptococcus agalactiae* (Bernheimer et al., 1979; Brown et al., 1974; Jurgens et al., 1985, 1987; Ruhlmann et al., 1988; Skalka et al., 1980), a number of other Gram-positive and Gram-negative bacteria are known to produce a positive CAMP reaction, including *Pasteurella haemolytica* (Fraser, 1962), *Aeromonas* species (Figura & Guglielmetti, 1987), some *Vibrio* species (Kohler, 1988) and group G streptococci (Soedermanto & Lammler, 1996). Some of these species can also use phospholipase C (α-toxin) from *Clostridium perfringens* or phospholipase D from *Corynebacterium pseudotuberculosis* as a co-factor for haemolysis in addition to the *Staphylococcus aureus* toxin (Frey et al., 1989). The CAMP factor genes of *Actinobacillus pleuropneumoniae* and *Streptococcus uberis* have been identified, cloned and expressed in *Escherichia coli* (Frey et al., 1989; Jiang et al., 1996).

The precise role of the CAMP molecule in bacterial virulence remains unclear. It is likely that the co-haemolytic reaction represents a laboratory phenotype, or epiphenomenon, that is convenient for CAMP factor detection, but which may not be directly related to the role of the molecule in colonization and pathogenesis. The CAMP factor from *Streptococcus agalactiae* binds to the Fc region of IgG and IgM molecules, similar to the binding of IgG by *Staphylococcus aureus* protein A (Jurgens et al., 1987), and partial amino acid sequence similarity between the CAMP factor protein of *Streptococcus agalactiae* and *Staphylococcus aureus* protein A has been demonstrated (Ruhlmann et al., 1988).

SUMMARY

The disclosure provides compositions and methods useful for treating or preventing *P. acnes* infection. In one embodiment, the methods and compositions comprise an ASMase inhibitor including, for example, small molecule inhibitors or anti-ASMase antibodies. In another embodiment, the composition and methods comprise a vaccine comprising a *P. acnes* CAMP factor. In yet another embodiment, the methods and compositions comprise an anti-*P. acnes* CAMP factor antibody. In yet a further embodiment, the methods and compositions comprise a combination of a vaccine, or antibody against CAMP Factor and an ASMase inhibitor or antibody.

The disclosure also provides an immunogenic composition comprising a substantially purified polypeptide comprising a sequence referred to in Table 1, an immunogenic fragment thereof, and any combination of the foregoing. In one embodiment, a CAMP Factor, lipase, or sialidase polypeptide or fragment thereof is use in the immunogenic composition. In yet another embodiment, a polypeptide comprising SEQ ID NO: 2, 3, 7, 9 or 11 or an immunogenic fragment thereof is used in the preparation of the immunogenic composition. In yet another embodiment, a vector comprising a polynucleotide encoding a polypeptide of SEQ ID NO: 2, 3, 7, 9 or 11 or an antigenic fragment thereof is expressed in a vector that is administered to a subject. In one embodiment, the vector comprises an attenuated bacterial vector or an attenuated viral vector. In yet another embodiment, the antigen is expressed by a plant or plant cell.

The disclosure also provides a composition comprising at least one recombinant attenuated bacterial or viral vector comprising at least one polynucleotide encoding one or more *P. acnes* polypeptides selected from the group consisting of a CAMP Factor, a lipase, or a sialidase such that the polypeptide is expressed in the at least one recombinant attenuated vector and an inhibitor of ASMase activity.

The disclosure also provides a method of inducing protective immunity in a subject comprising administering a composition as described above to the subject and contacting the subject with an ASMase inhibitor.

The disclosure also provides an immunoprotective composition comprising at least one attenuated vector or plant preparation expressing an antigen useful for inducing an immunoprotective response against *Propionibacterium acnes* (*P. acnes*), said antigen comprising an extracellular or immunogenic protein of *P. acnes* or immunogenic fragment thereof linked to transcriptional promoter and termination signals. In one embodiment, the *P. acnes* protein or fragment thereof is selected from the group consisting of CAMP factor, a lipase, a sialidase, and any combination thereof.

The disclosure provides a composition useful for treating a *P. acnes* infection comprising an ASMase inhibitor. In yet a further embodiment, a CAMP antigen or vaccine may be used in combination with the ASMase inhibitor. In yet another embodiment, an antigenic composition comprising a disrupted non-infective *P. acnes* cell and further comprising an ASMase inhibitor is used.

The disclosure provides a method for treating *P. acnes* comprising administering to a subject a vaccine comprising a CAMP factor and a composition comprising an ASMase inhibitor.

DETAILED DESCRIPTION

Figure 1:
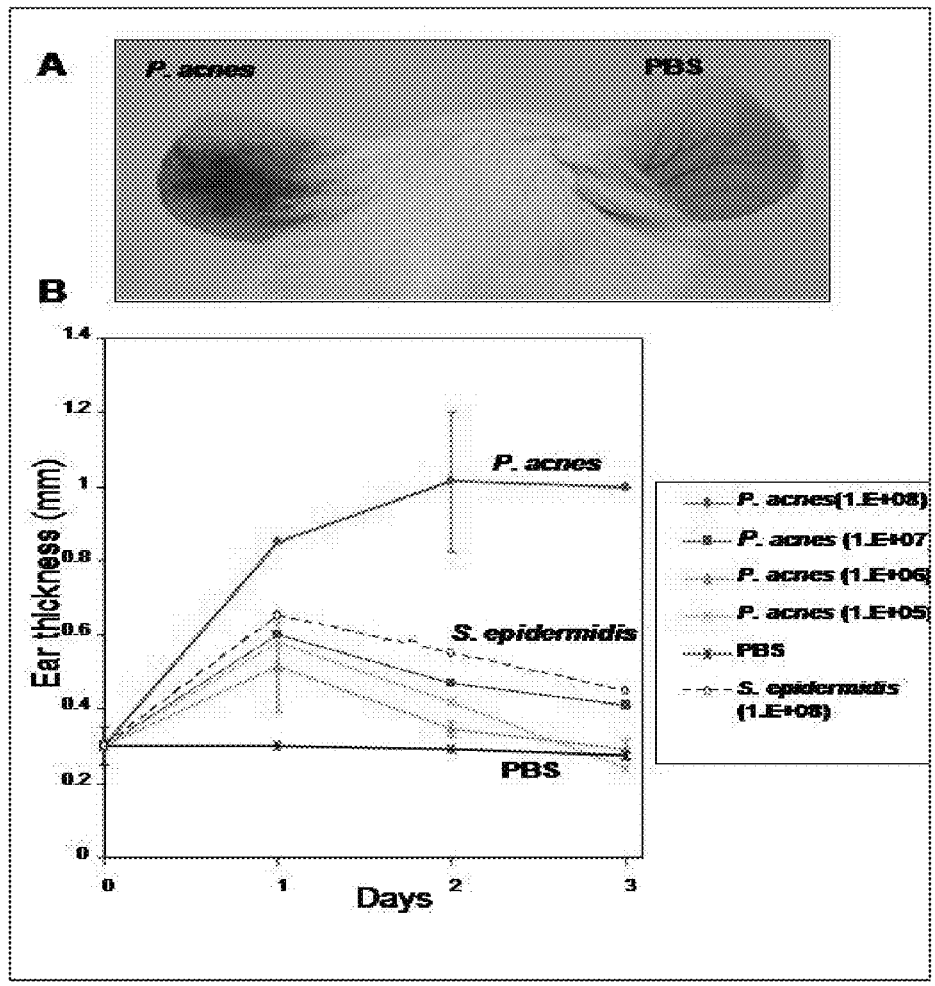
FIG. 1A-B shows ear inflammation and thickness after injection with *P. acnes* and *S. epidermidis*. Ear inflammation was observed when an ICR mouse was subcutaneously injected with 25 µl of *P. acnes* ($10^8$ CFU) (A). Injection with 25 µl of PBS into the other ear of the same mouse did not cause visible inflammation. *P. acnes* ($10^5$ to $10^8$ CFU) and *S. epidermidis* ($10^8$) were subcutaneously injected into mouse skins. Ear thickness was measured everyday for 3 days using Peacock Thickness gauge (B). The ears of two mice per group were measured.

The exemplary descriptions provided herein are exemplary and explanatory only and are not restrictive of the invention, as claimed. Moreover, the invention is not limited to the particular embodiments described, as such may, of course, vary. Further, the terminology used to describe particular embodiments is not intended to be limiting.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

It must be noted that, as used herein and in the appended claims, the singular forms "a" and "the" include plural referents unless the context clearly dictates otherwise. Thus, for example, reference to "a polypeptide" includes a plurality of such polypeptides and reference to "the bacteria" includes reference to one or more bacteria and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

*Propionibacterium acnes* (*P. acnes*) is involved in many human polymicrobial diseases including acne vulgaris, endocarditis, endophthalmitis, osteomyelitis, joint, nervous system, and cranial neurosurgery infections, and implanted biomaterial contamination. More than fifty million people in the U.S have acne vulgaris. In addition, acne vulgaris is the most common skin disease that affects 85-100% of people at some time during their lives. Systemic antibiotic therapy for acne lesions non-specifically kills the majority of skin bacteria, which impacts the homeostasis of skin resident flora. Vaccines against acne vulgaris and *P. acnes*-induced diseases were not available prior to this disclosure. The disclosure provides anti-*P. acnes* vaccines to suppress *P. acnes*-induced skin inflammation.

Proliferation of *P. acnes* starts in the microcomedone, which is the precursor of acne lesion characterized by hyperkeratinization, formation of a keratin plug, and increase in sebum secretion by sebaceous gland. The microcomedo provides an anaerobic, sebum-rich microenvironment in the hair follicle, which promotes overgrowth of *P. acnes*. The initial event in acne inflammation is the disruption of follicular epithelium by this overgrowth of *P. acnes*, allowing the bacteria in the comedo to come in contact with the host immune systems, triggering granulomatous inflammation (typical inflammatory acne). *P. acnes* stimulates the production of pro-inflammatory cytokines, including interleukins-1β, -8, -12, and tumor necrosis factor-α, via toll-like receptor 2.

Acne vulgaris is one of the most common skin diseases that can result in severe inflammatory lesions that are highly associated with P. acnes infection. S. epidermidis and P. acnes have been recognized as major skin bacteria that cause the formation of acne vulgaris. In addition, these bacteria have the ability to synthesize lipases that degrade sebum triglycerides into free fatty acids which trigger inflammatory responses. Treatment of acne should be started as early as possible to minimize the risk of scarring and adverse psychological effects. Many antibiotics have been used for acne treatment, but these antibiotics in general are non-specific, short lasting and normally are applied when acne lesions have already occurred (such as in late stages of acne). Development of anti-acne vaccines can prevent acne progression from the early stages and increase the specificity of treatments as described herein.

Acne vulgaris is a multi-factorial disease associated with polymicrobial infection, hormone regulation and immune responses. The inflammatory stage of acne vulgaris is usually of greatest concern to the patient. Inflammatory lesions may lead to scarring and adverse psychological effects. Vaccines, which selectively suppress the P. acnes-induced inflammation, will minimize the risk of changing the homeostasis of body hormones and resident skin microbes.

Hemolysis is a virulence factor employed by numerous bacterial pathogens to degrade, invade host cells, and resist the host immune attack. This is achieved through various mechanisms targeting the cell membrane: enzymatic, pore-forming, or surfactant. When P. acnes is grown on a sheep blood agar plate in close proximity to beta-hemolytic microorganisms, such as Staphylococcus aureus (S. aureus) and Clostridium perfringens, it synergistically enhances hemolysis similar to the classical Christie, Atkins, Munch-Peterson (CAMP). CAMP reactions are induced by the combination of CAMP factor co-hemolysin, which is a pore-forming toxin, and sphingomyelinase (SMase) derived from the other bacterial partner. CAMP factor itself has only weak hemolytic activity on the erythrocytes, but pretreating the cells with SMase enhances its activity. SMase initially hydrolyzes sphingomyelin on the cell membrane of erythrocytes to ceramide, which renders the cells susceptible to the hemolytic activity of CAMP factor. The entire genomic sequence of P. acnes includes numerous genes whose products are involved in degrading host molecules, and five genes encoding CAMP factor homologs of Streptococcus agalactiae (S. agalactiae) have been found in the genome information. This comprehensive analysis of P. acnes proteins by a proteomic technique utilizing isotope-coded protein labels coupled to NanoLC-MS analysis revealed that one of the CAMP factor homologs (accession number: gi/50842175, incorporated herein by reference), showing 42% identity in nucleotide sequence to the S. agalactiae CAMP factor, is produced at higher concentrations by bacteria cultured under anaerobic condition than under aerobic conditions. These data suggest a physiological significance for the CAMP factor for P. acnes.

The CAMP factor from Streptococcus agalactiae binds to the Fc region of IgG and IgM molecules, similar to the binding of IgG by Staphylococcus aureus protein A (Jurgens et al., 1987), and partial amino acid sequence similarity between the CAMP factor protein of Streptococcus agalactiae and Staphylococcus aureus protein A has been demonstrated (Ruhlmann et al., 1988). Evidence is presented of differences amongst P. acnes types IA, IB and II in the expression of proteins with sequence similarity to the CAMP co-haemolysin.

The disclosure demonstrates that P. acnes secretes CAMP factor, which is shown to act synergistically with bacterial sphingomyelinase (SMase) to lyse erythrocytes. Furthermore, the disclosure demonstrates that recombinant P. acnes CAMP factor alone induced cell death in human keratinocyte (HaCaT) and murine macrophage (RAW264.7) cell lines in a dose-dependent manner. For example, intradermal injection of mouse ears with CAMP factor induced significant ear swelling. In addition, host acid SMase (ASMase) was released/secreted from HaCaT and RAW264.7 cells when the cells were co-cultured with P. acnes. P. acnes-induced cytotoxicity in both cell lines was significantly neutralized by including either a selective ASMase inhibitor, anti-ASMase antibodies or anti-CAMP factor antiserum. Intradermal injection of mouse ears with live P. acnes attracted numerous macrophages, which strongly express ASMase, resulting in an increase in soluble ASMase in the ear after P. acnes challenge. Most notably, vaccination of ICR mice with CAMP factor yielded protective immunities against P. acnes-induced inflammation and the development of skin lesions. In addition, the combination of vaccinating with CAMP factor and locally injecting anti-ASMase IgG synergistically reduced P. acnes-induced ear swelling. These data demonstrate that P. acnes benefits from host enzymes that amplify its pathogenicity; P. acnes may utilize host ASMase to enhance the toxicity of its CAMP-factor, which may contribute to its evasion of host immune defenses, degrade host tissues, and spread the pathogen.

The complete genome sequence of P. acnes is known and incorporated herein by reference in its entirety. The disclosure identifies virulence factors and provides a set of vaccines capable of providing protective immunity against P. acnes. Other virulence factors and antigenic compositions will be readily apparent and are encompassed by the disclosure. Specifically, the antigens upregulated in anaerobic conditions as identified in Table 1 are targets for the development of vaccines based upon the teachings herein. The disclosure establishes a proteome of P. acnes by comparing the differential expression of P. acnes proteins between anaerobic and aerobic conditions (see examples and Table 1). This analysis revealed a number of genes that were upregulated. The disclosure further provides additional data on three secretory virulence factors (CAMP factor, lipase, and sialidase) associated with P. acnes-induced host cell damage and inflammation.

The anti-P. acnes vaccines provided by the disclosure benefit subjects suffering from polymicrobial P. acnes associated diseases including acne vulgaris, endocarditis, endophthalmitis, osteomyelitis, joint, nervous system, and cranial neurosurgery infections, and implanted biomaterial contamination.

In addition to vaccine targets, three secretory virulence factors (CAMP factor, lipase, and sialidase) as well as killed-P. acnes serve as candidates for development of anti-P. acnes drugs. For example, based upon the disclosure methods of identifying therapeutics for the treatment of microbial infections can include approaches from proteomic protein identification to vaccine evaluation. The disclosure provides a platform for the studies of functional proteomics and vaccine/drug creation using the identified secretory virulence factors.

The disclosure provides, for example, anti-P. acnes vaccines targeting secreted CAMP factor, lipase and sialidase as well as antigens from Killed-P. acnes. The vaccines of the disclosure were demonstrated both in vitro and in vivo. The vaccines reduced inflammation caused by P. acnes.

The disclosure further demonstrates that targeting secretory virulence factors is an effective strategy to decrease P. acnes-induced inflammation.

The vaccines of the disclosure can be used alone or with systemic antibiotic therapy.

A "polynucleotide" generally refers to any polyribonucleotide (RNA) or polydeoxyribonucleotide (DNA), which may be unmodified or modified RNA or DNA. Polynucleotides include, without limitation, single-stranded and double-stranded DNA, DNA that is a mixture of single-stranded and double-stranded regions, single-stranded and double-stranded RNA, and RNA that is a mixture of single-stranded and double-stranded regions. Polynucleotides also include hybrid molecules comprising DNA and RNA that may be single-stranded or, more typically, double-stranded or a mixture of single-stranded and double-stranded regions. In addition, "polynucleotide" refers to triple-stranded regions comprising RNA or DNA or both RNA and DNA. Polynucleotides also include DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. Oligonucleotides are relatively short polynucleotides. Examples of polynucleotides useful in the methods of the disclosure to produce antigen to induce an immune reaction include those set forth in Table 1, including fragments thereof encoding antigenic epitopes.

TABLE 1

Protein differential expression with/without oxygen

| Accession # | Proteins | $+O_2$ | $-O_2$ |
|---|---|---|---|
| *Secretory virulence factors* | | | |
| gi/50842175 | CAMP factor | | * |
| gi/50843543 | lipase | | * |
| *Membrane proteins* | | | |
| gi/50841878 | ABC transporter ATP-binding protein | * | |
| gi/50843296 | Extracellular solute-binding transport protein, putative oligopeptide-binding protein | | * |
| gi/50843565 | S-layer protein | | * |
| *Enzymes* | | | |
| gi/50843566 | Arginyl-tRNA synthetase | | * |
| gi/50842182 | Aminopeptidase | | * |
| gi/50843224 | Biofunctional GMP synthase | * | |
| gi/50842971 | Carbamate kinase | | * |
| gi/50841588 | Catalase | | * |
| gi/50842082 | Methylmalonyl-CoA mutase | * | |
| gi/50842890 | Phenylalanyl-tRNA synthetase beta chain | | * |
| gi/50842304 | Phosphoglycerate kinase | | * |
| gi/50842950 | Polyribonucleotide nucleotidyltransferase | | * |
| gi/50841767 | Putative Clp-family ATP-binding protease | * | |
| gi/50841972 | UTP-glucose-1-phosphate uridylyltransferase | | * |
| *Others* | | | |
| gi/50843142 | Conserved protein (DUF174) | | * |
| gi/50843329 | Elongation factor G | * | |
| gi/50843484 | Molecular chaperone DnaK | | * |
| gi/50841600 | Myosin-crossreactive antigen | | * |
| gi/50843708 | Rare lipoprotein A, RlpA family | * | |
| gi/50843315 | 50S Ribosomal protein L2 | * | |
| gi/50843340 | 50S Ribosomal protein L10 | * | |

The sequences associated with the foregoing accession numbers are incorporated herein by reference in their entirety.

A "polypeptide" refers to any polypeptide comprising two or more amino acids joined to each other by peptide bonds or modified peptide bonds. "Polypeptide" refers to both short chains, commonly referred to as peptides, oligopeptides or oligomers, and to longer chains, generally referred to as proteins. Polypeptides may contain amino acids other than those normally encoded by a codon.

Polypeptides include amino acid sequences modified either by natural processes, such as post-translational processing, or by chemical modification techniques that are well known in the art. Such modifications are well described in the literature and are known in the art. Modifications may occur anywhere in a polypeptide, including the peptide backbone, the amino acid side-chains and the amino or carboxyl termini. Such modifications may be present to the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from post-translation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Examples of polypeptides useful in the methods and compositions of the disclosure comprise the *P. acnes* polypeptides set forth in SEQ ID Nos: 2, 3, 7 and 9 and human ASMase as set forth in SEQ ID NO: 11, antigenic fragment thereof, and antigenic fragments comprising 80%, 85%, 90%, 95%, 98%, or 99% identity to SEQ ID NO: 2, 3, 7, 9 and 11. Such polypeptides and fragments thereof are useful for immunization and to raise antibodies. Antigens comprising polypeptides of the disclosure are useful for generating an immune response in a subject.

An immune response is generated to an antigen through the interaction of the antigen with the cells of the immune system. The resultant immune response may be broadly distinguished into two extreme categories, being humoral or cell mediated immune responses (traditionally characterized by antibody and cellular effector mechanisms of protection, respectively). These categories of response have been termed Th1-type responses (cell-mediated response), and Th2-type immune responses (humoral response). Extreme Th1-type immune responses may be characterized by the generation of antigen-specific, haplotype-restricted CTLs, and natural killer cell responses. In mice, Th1-type responses are often characterized by the generation of antibodies of the IgG2a subtype, while in the human these correspond to IgG1 type antibodies. Th2-type immune responses are characterized by the generation of a broad range of immunoglobulin isotypes including in mice IgG1, IgA, and IgM.

The driving force behind the development of these two types of immune responses is cytokines, a number of identified protein messengers which serve to help the cells of the immune system and steer the eventual immune response to either a Th1 or Th2 response. Thus, high levels of Th1-type cytokines tend to favor the induction of cell mediated immune responses to the given antigen, while high levels of Th2-type cytokines tend to favor the induction of humoral immune responses to the antigen. It is important to remember that the distinction of Th1 and Th2-type immune responses is not absolute. In reality, an individual will support an immune response which is described as being predominantly Th1 or predominantly Th2. Traditionally, Th1-type responses are associated with the production of the INF-γ and IL-2 cytokines by T-lymphocytes. Other cytokines often directly associated with the induction of Th1-type immune responses are not produced by T-cells, such as IL-12. In contrast, Th2-type responses are associated with the secretion of IL-4, IL-5, IL-6, IL-10 and tumor necrosis factor-β(TNF-β.

The disclosure provides *P. acnes* antigens that are immunoprotective. Such antigens can be delivered in a number of ways to the host so as to stimulate a protective immune response against *P. acnes*. The antigens can be delivered via an attenuated vector that results in presentation via MHC class I (e.g., such vectors include *L. monocytogenes, E. coli*, non-virulent *P. acnes* or another attenuated bacterial vector such as *Mycobacterium bovis* BCG, *Shigella flexneri*). The term "attenuated," when used with respect to a bacteria, means that the bacteria has lost some or all of its ability to proliferate and/or cause disease or other adverse effect when the bacteria infects an organism. For example, an "attenuated" bacterium may be unable to replicate at all, or be limited to one or a few rounds of replication, when present in an organism in which a wild-type or other pathogenic version of the attenuated bacteria can replicate. Alternatively or additionally, an "attenuated" bacterium might have one or more mutations in a gene or genes that are involved in pathogenicity of the bacteria. Many genes, loci, or operons are known, mutations in which will result in an attenuated bacteria. Examples of attenuated bacteria used as live vaccines include *S. typhi* carrying a mutation in its galE or htrA gene, and *V. cholerae* carrying mutations in its ctxA gene.

Microorganisms which are used to express the *P. acnes* for use in immunoprotective compositions include, without limitation, *Campylobacter* sp., *Yersinia* sp., *Helicobacter* sp., *Gastrospirillum* sp., *Bacteroides* sp., *Klebsiella* sp., *Lactobacillis* sp., *Streptococcus gordonii, Enterobacter* sp., *Salmonella* sp., *Shigella* sp., *Aeromonas* sp., *Vibrio* sp., *Clostridium* sp., *Enterococcus* sp. and *Escherichia coli* (see e.g. U.S. Pat. Nos. 5,858,352, and 6,051,416, and Levine et al., in "New Generation Vaccines Second Edition" ed. Levine et al., Marcel Dekker, Inc. pp 351-361 (1997), Levine et al., in "New Generation Vaccines Second Edition" ed. Levine et al., Marcel Dekker, Inc. pp 437-446 (1997), Butterton et al., in "New Generation Vaccines Second Edition" ed. Levine et al., Marcel Dekker, Inc. pp 379-385 (1997) and Fennelly et al., in "New Generation Vaccines Second Edition" ed. Levine et al., Marcel Dekker, Inc. pp 363-377 (1997)). For example, *Campylobacter jejuni, Campylobacter coli, Listeria monocytogenes, Yersinia enterocolitica, Yersinia pestis, Yersinia pseudotuberculosis, Escherichia coli, Shigella flexneri, Shigella sonnei, Shigella dysenteriae, Shigella boydii, Helicobacter pylori, Helicobacter felis, Gastrospirillum hominus, Vibrio cholerae, Vibrio parahaemolyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Klebsiella pneumoniae, Enterobacter cloacae*, and *Enterococcus faecalis* can be used. *Escherichia coli* include, but are not limited to, entero-toxic, entero-hemorrhagic, entero-invasive, entero-pathogenic or other strains can be used in the disclosure.

Alternatively, or in addition to the above, a non-bacterial attenuated vector such as a replication-deficient viral vectors may be used in the methods and compositions of the disclosure. Such viral vectors useful in the methods and compositions of the disclosure include, but are not limited to, Vaccinia, Avipox, Adenovirus, AAV, Vaccinia virus NYVAC, Modified vaccinia strain Ankara (MVA), Semliki Forest virus, Venezuelan equine encephalitis virus, and herpes viruses. Naked DNA vectors can also be used in addition to antigenic proteins alone or in combination with an adjuvant. The naked DNA can be taken up and expressed by cells of the vaccinated subject resulting in the induction of an immune reaction to the expressed polypeptide.

Examples of suitable viral vectors include herpes simplex viral vectors, vaccinia or alpha-virus vectors and retroviruses, including lentiviruses, adenoviruses and adeno-associated viruses. In one embodiment, these vectors are replication defective virus vectors. Gene transfer techniques using these viruses are known to those skilled in the art. Retrovirus vectors, for example, may be used to stably integrate the polynucleotide of the disclosure into the host genome, although such recombination may not be advisable. Replication-defective adenovirus vectors by contrast remain episomal and therefore allow transient expression.

In one embodiment, the adenovirus used as a live vector is a replication defective human or simian adenovirus. Typically these viruses contain an E1 deletion and may be grown on cell lines that are transformed with an E1 gene. Suitable Simian adenoviruses are, for example, viruses isolated from Chimpanzee. Examples of viruses suitable for use in the disclosure include C68 (also known as Pan 9) (U.S. Pat. No. 6,083,716, incorporated herein by reference) and Pan 5, 6 and Pan 7 (WO 03/046124 incorporated herein by reference). Thus, these vectors can be manipulated to insert a heterologous polynucleotide coding for an antigen such that the product is expressed. The use formulation and manufacture of such recombinant adenoviral vectors is set forth in detail in WO 03/046142, which is incorporated by reference.

The disclosure also contemplates the use of plant systems for expression of antigens of the disclosure. The plant tissue or purified polypeptide may be used for immunization. For example, agroinfiltration is a method by which transient expression of genes or production or protein is accomplished in a plant. In the method a suspension of *Agrobacterium* is delivered to a plant leaf, where the *agrobacterium* transfers a desired coding sequence (e.g., a CAMP polynucleotide) to plant cells. A strain of *Agrobacterium* is transformed with a polynucleotide comprising the coding sequence of interest. Subsequently the strain is grown in culture the *agrobacterium* is then injected into a plant tissue (e.g., the airspaces inside the leaf through stomata. Once inside the leaf polynucleotide is then transiently expressed. Many plants can be transformed by this method, but the most common ones are *Nicotiana benthamiana* and *Nicotiana tabacum*.

In addition, the disclosure envisions immunization utilizing a combination of antigens and/or vectors. The disclosure contemplates a homologous or heterologous prime-boost vaccination strategy. The heterologous strategy may include priming with one vector, e.g. *L. monocytogenes* expressing one or more proteins, and boosting with another vector, e.g., adenovirus expressing the same protein or proteins, or vice versa. Boosting may also include immunizing with a *P. acnes* protein or proteins or fragments thereof in an adjuvant. The specific examples provided herein demonstrate the delivery of the antigens to an animal host utilizing various vaccination strategies and the resulting immunoprotection against *P. acnes* challenge.

The disclosure comprises several types of vaccines. One group of vaccines comprises an attenuated bacterial vector expressing one or more *P. acnes* antigens. Other vaccines of the disclosure comprise *P. acnes* antigens (e.g., polypeptide or fusion polypeptides) in a suitable adjuvant. Another group of vaccines of the disclosure comprise a viral vector (e.g., adenovirus) expressing one or more *P. acnes* antigens.

Each vaccine is administered, e.g. transdermally, subcutaneously, intramuscularly, intranasally, inhaled, or even orally to a mammalian host. The vaccine can be administered as part of a homologous or heterologous prime-boost strategy. Most importantly, the vaccine protects the mammalian hosts against infection with *P. acnes*.

A "vaccine" as used herein refers to a composition of matter comprising a molecule that, when administered to a subject, induces an immune response. Vaccines can comprise polynucleotide molecules, polypeptide molecules, and carbohydrate molecules, as well as derivatives and combinations of each, such as glycoproteins, lipoproteins, carbohydrate-protein conjugates, fusions between two or more polypeptides or polynucleotides, and the like. A vaccine may further comprise a diluent, an adjuvant, a carrier, or combinations thereof, as would be readily understood by those in the art.

A vaccine may be comprised of separate components. As used herein, "separate components" refers to a situation wherein the vaccine actually comprises two discrete vaccines to be administered separately to a subject. In that sense, a vaccine comprised of separate components may be viewed as a kit or a package comprising separate vaccine components. For example, in the context of the disclosure, a package may comprise a first immunogenic composition comprising an attenuated bacterial vector and a second antigenic composition comprising an attenuated viral vector comprising the same or different *P. acnes* antigens (e.g., CAMP factor, a lipase, or a sialidase).

A vaccine "induces" an immune response when the antigen or antigens present in the immunogenic compositions/vaccine cause the vaccinated subject to mount an immune response to that antigen or antigens. The vaccinated subject will generate an immune response, as evidenced by activation of the immune system, which includes the production of vaccine antigen-specific T cells, vaccine antigen-specific B cells, vaccine antigen-specific antibodies, and cytokines. The resulting immune response may be measured by several methods including ELISPOT, ELISA, chromium release assays, intracellular cytokine staining, FACS analysis, and MHC tetramer staining (to identify peptide-specific cells). A skilled artisan may also use these methods to measure a primary immune response or a secondary immune response.

An "antigen" is a substance capable of generating an immune response in a subject exposed to the antigen. Antigens are usually polypeptides and are the focus of the host's immune response. An "epitope" or "antigenic determinant" is that part of an antigen to which T cells and antibodies specifically bind. An antigen may contain multiple epitopes. Antigens of the disclosure comprise *P. acnes* extracellular or immunogenic polypeptides (e.g., lipase, CAMP Factor and those set forth in Table 1). In specific embodiments, the *P. acnes* polypeptides comprises an antigenic fragment of a polypeptide comprising the sequence as set forth in SEQ ID NO: 2, 3, 7 or 9 and antigenic fragments of human ASMase of SEQ ID NO:11 or fragments that have at least 80%-99% identity to an antigenic fragment of SEQ ID NO: 2, 3, 7, 9 and 11.

In one embodiment, the vaccine comprises an antigenic fragment of a *P. acnes* CAMP factor. An antigenic fragment typically comprises at least 6 amino acid (e.g., 6-10, 10-12, 12-20, 30-50 or more amino acids). Typically the antigenic fragment is a fragment of the protein found on the surface of the protein and is comprises a soluble domain. In one embodiment, the antigenic fragment may be part of a fusion protein comprising one or more non-contiguous sequence of the protein (e.g., non-contiguous sequence of CAMP factor of *P. acnes*). In one embodiment, the vaccine comprises an antigenic domain of a polypeptide comprising SEQ ID NO:7. In one embodiment, the vaccine comprises a polypeptide comprising a sequence at least 80%, 90%, 95%, 98% or 99% identical to SEQ ID NO:7. In yet another embodiment, the vaccine comprises a polypeptide having a sequence as set forth in SEQ ID NO:7 or a fragment thereof of at least 6 amino acids and which is capable of producing antibodies that specifically bind to a *P. acnes* CAMP factor (e.g., a polypeptide consisting of SEQ ID NO:7).

A vaccine can include killed and disrupted *P. acnes*. As described more fully below the killing and disruption results in the release of various antigens that may not be secreted unless cultured in an anaerobic environment. Thus, in one embodiment, the disclosure contemplates culturing *P. acnes* under anaerobic conditions followed by killing and/or disruption of the bacterial and preparing a vaccine from the disrupted *P. acnes* preparation. The disrupted preparation may be further purified to enrich an antigen or antigens in the immunogenic compositions. In another embodiment, anaerobically cultured *P. acnes* are killed by gamma irradiation or other methods known to those of skill in the art and the whole bacterial cell used in an immunogenic preparation.

A priming vaccine used in some embodiments of the disclosure comprises a *P. acnes* CAMP Factor, lipase or sialidase antigen. The priming vaccine comprises an antigenic epitope of a *P. acnes* antigen, the full length antigen, a vector comprising a polynucleotide encoding the antigen and the like. In one embodiment, the priming vaccine comprises a polynucleotide encoding an antigen under control of a foreign promoter within a bacterium, plant cell or virus. The polynucleotide of the priming vaccine is present in a suitable delivery vector such as a plasmid or other vector such as a bacterial, plant cell or viral vector. The polynucleotide may be under the control of a suitable promoter such as a promoter derived from the HCMV IE gene. The priming vaccine is administered in an amount effective for priming an immune response to the *P. acnes* antigen. As used herein, "priming" of an immune response occurs when an antigen is presented to T cells or B cells. As a result, primed cells can respond to the same antigen again as memory cells in a second, subsequent immune response. Thus, priming generates both the primary immune response and establishes immunological memory. One skilled in this art appreciates that a primary immune response represents the adaptive immune response upon initial exposure to an antigen in a particular context such as in the pathogen or in a vaccine. However, it will also be appreciated that the disclosure is not limited to use of the priming vaccine in the context of immunologically naive individuals. Rather, priming may also occur in individuals who have been exposed to the antigen but who have not received the priming vaccine.

The priming immunogenic (vaccine) composition may be administered once prior to administration of the boosting immunogenic (vaccine) composition. In another embodiment, the priming vaccine may be administered several times.

The boosting vaccine used in the method of the disclosure may comprise at least one *P. acnes* antigen (e.g., CAMP Factor, lipase or sialidase antigen polypeptide or fragment thereof) corresponding to the antigen of the priming vaccine. In addition, the boosting vaccine may comprise (in addition to the priming antigen) a different antigen or vector comprising the antigen or coding region thereof. In one embodiment, the boosting vaccine comprises a *P. acnes* polypeptide antigen to enhance the immunogenicity of the subject to *P. acnes*. For example in one embodiment, the boosting vaccine comprises a *P. acnes* antigen expressed in a viral vector. The *P. acnes* antigen can be selected from the group of antigen listed as upregulated in Table 1 including, but not limited to, CAMP Factor, lipase, sialidase antigens, fragments or combinations thereof.

The boosting vaccine is administered in an amount effective for "boosting" a primed immune response to the *P. acnes* antigen. As used herein, "boosting" an immune response means to induce a secondary immune response in a subject that has been primed (i.e., already exposed) by an initial exposure to an antigen. A secondary immune response is characterized by the activation and expansion of specific memory T cells and B cells. Thus, boosting a specific immune response augments the primed immune response by inducing immune cells to proliferate and differentiate upon subsequent exposure to that antigen. The boosting vaccine may achieve one or more of the following effects: induces CD4+ T cells, induces anti-*P. acnes* antibodies (e.g., antibodies to the antigen in the vaccine), boosts the activity of the CD8+ T cells primed by the priming vaccine, and induces additional CD8+ T cells not originally identified in the initially primed immune response. The boosting vaccine may also induce CD4+ T cells and induce anti-*P. acnes* antibodies (e.g., anti-CAMP factor antibodies).

The existence of an immune response to the first dose of the immunoprotective composition may be determined by known methods (e.g., by obtaining serum from the individual before and after the initial immunization, and demonstrating a change in the individual's immune status, for example an immunoprecipitation assay, or an ELISA, or a bactericidal assay, or a Western blot, or flow cytometric assay, or the like) prior to administering a subsequent dose. The existence of an immune response to the first dose may also be assumed by waiting for a period of time after the first immunization that, based on previous experience, is a sufficient time for an immune response and/or priming to have taken place. Boosting dosages of an immunoprotective composition can be administered as needed.

Certain vaccine adjuvants are particularly suited to the stimulation of either Th1 or Th2-type cytokine responses. Traditionally, the best indicators of the Th1:Th2 balance of the immune response after a vaccination or infection includes direct measurement of the production of Th1 or Th2 cytokines by T lymphocytes in vitro after restimulation with antigen, and/or the measurement of the IgG1:IgG2a ratio of antigen specific antibody responses. Thus, a Th1-type adjuvant is one which stimulates isolated T-cell populations to produce high levels of Th1-type cytokines when re-stimulated with antigen in vitro, and induces antigen specific immunoglobulin responses associated with Th1-type isotype.

The disclosure further relates to antibodies for the prevention and/or treatment of a *P. acnes* infection. In a first embodiment, an antibody is raised against a *P. acnes* antigen of the disclosure. Such antibodies are produced by administering an antigenic composition comprising an antigenic polypeptide (e.g., a *P. acnes* CAMP Factor), a vector expressing an antigenic polypeptide or a purified preparation of a *P. acnes* antigen as a vaccine.

Antibodies (such as anti-CAMP Factor or anti-ASMase antibodies) according to the disclosure will be administered in one or more dosages, and the amount needed will depend on during which phase of the disease the therapy is given as well as on other factors. In order to produce such antibodies, the antigenic composition (such as an antigenic fragment of an CAMP factor or ASMase) according to the disclosure will be administered to a subject in order to induce the production of the above described antibodies. The antibodies can be monoclonal antibodies. Once obtained, such novel antibodies may be produced by conventional techniques and used in therapy. In general, a monoclonal antibody to an epitope of an antigen can be prepared by using a technique which provides for the production of antibody molecules from continuous cell lines in culture and methods of preparing antibodies are well known to the skilled in this field (see e.g. Coligan (1991) Current Protocols in Immunology, Wiley/Greene, NY; Harlow and Lane (1989) Antibodies: A Laboratory Manual, Cold Spring Harbor Press, NY; and Goding (1986) Monoclonal Antibodies: Principles and Practice (2nd ed) Academic Press, New York, N.Y.). In addition, such antibodies may be humanized using techniques known in the art. Furthermore, the antibody may include antibody fragments known in the art.

Passive immunization is the induction of immunity acquired by the transfer of antibodies from another individual (A Keller and Stiehm, 2000). There are many advantages of passive immunization. (a) Unlike active immunization (vaccines), biological effects of passive immunization are immediate and can be of value, as in cases where symptoms have already occurred. Thus, the modality using passive neutralization of *P. acnes* CAMP factor may benefit patients who have already developed acne. (b) No cell-mediated immunity and no direct bactericidal effect that will have low impact on microbe commensalisms. (c) No adjuvant-derived side effects are induced. (d) The administered dose can be adjusted based on the severity of disease. (e) It can be easily combined with other therapies. Additionally, unlike active immunization, which requires time to induce protective immunity and depends on the host's ability to mount an immune response, passive antibody can theoretically confer protection regardless of the immune status of the host (Casadevall, 2002). The disclosure demonstrates that passive immunization targeting secretory CAMP factors instead of bacterial surface proteins can neutralize the *P. acnes* virulence without directly killing bacteria, lowering the risk of creating drug-resistant *P. acnes* and altering the commensalisms of *P. acnes*.

As demonstrated herein, a synergistic effect can be seen in the treatment of a *P. acnes* infection by immunizing with an antigenic CAMP factor peptide or polypeptide and also contacting the subject with an antibody to ASMase or an ASMase inhibitor. For example, the disclosure contemplate treating or preventing a *P. acnes* infection using (a) a vaccine comprising a *P. acnes* CAMP factor peptide or polypeptide, (b) an anti-ASMase antibody, (c) an ASMase inhibitor, and (d) any combination of the foregoing. Again, as used herein a CAMP factor peptide or polypeptide does not necessarily refer to the origin of the peptide or polypeptide but rather to (a) the sequence, which will have some degree of identity to the wild-type CAMP factor; and (b) the ability of an antibody developed against such a sequence to recognize For therapeutic purposes, the antibody is formulated with conventional pharmaceutically or pharmacologically acceptable vehicles for administration, conveniently by injection. Vehicles include deionized water, saline, phosphate-buffered saline, Ringer's solution, dextrose solution, Hank's solution, and the like. Other additives may include additives to provide isotonicity, buffers, preservatives, and the like. The antibody may be administered parenterally, typically intravenously or intramuscularly, as a bolus, intermittently or in a continuous regimen.

Methods for ameliorating *P. acnes* in a subject by administering to the subject a *P. acnes* antigen(s) (e.g., a *P. acnes* CAMP Factor protein, polypeptide, peptide) or a vector comprising a *P. acnes* antigen alone or in combination with an anti-SMase (e.g., an anti-ASMase) antibody or inhibitor thereof, in a pharmaceutically acceptable carrier, are also provided. In addition, methods for ameliorating P. acnes in a subject, by administering to the subject antibodies that bind to P. acnes antigens or to an ASMase, in a pharmaceutically acceptable carrier, are also provided.

Attenuated vaccines can be administered directly to the mammal. The immunogenic compositions and vaccines obtained using the methods of the disclosure can be formulated as pharmaceutical compositions for administration in any suitable manner. One route of administration is oral. Other routes of administration include rectal, intrathecal, buccal (e.g., sublingual) inhalation, intranasal, and transdermal and the like (see e.g. U.S. Pat. No. 6,126,938). Although more than one route can be used to administer a particular composition, a particular route can often provide a more immediate and more effective reaction than another route.

The immunoprotective compositions to be administered are provided in a pharmaceutically acceptable solution such as an aqueous solution, often a saline or buffered solution, or they can be provided in powder form. There is a wide variety of suitable formulations of pharmaceutical compositions of the disclosure. See, e.g., Lieberman, Pharmaceutical Dosage Forms, Marcel Dekker, Vols. 1-3 (1998); Remington's Pharmaceutical Science, 17th ed., Mack Publishing Company, Easton, Pa. (1985) and similar publications. The compositions may also include an adjuvant. Examples of known suitable adjuvants include alum, aluminum phosphate, aluminum hydroxide, and MF59 (4.3% w/v squalene, 0.5% w/v Tween 80, 0.5% w/v Span 85)—these are the only ones currently licensed for use in humans. For experimental animals, one can use Freund's, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dip-almitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, or Bacille Calmette-Guerin (BCG). The effectiveness of an adjuvant may be determined by measuring the amount of antibodies directed against the immunogenic antigen.

The concentration of immunogenic antigens of the disclosure in the pharmaceutical formulations can vary widely, e.g., from less than about 0.1%, usually at or at least about 2% to as much as 20% to 50% or more by weight, and will be selected primarily by fluid volumes, viscosities, and the like, in accordance with the particular mode of administration selected.

Formulations suitable for oral administration can comprise (a) liquid solutions, such as an effective amount of the recombinant bacteria or polypeptide suspended in diluents, such as buffered water, saline or PEG 400; (b) capsules, sachets or tablets, each containing a predetermined amount of the active ingredient, as lyophilized powder, liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, tragacanth, microcrystalline cellulose, acacia, gelatin, colloidal silicon dioxide, croscarmellose sodium, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art. It is recognized that the attenuated vaccines, when administered orally, must be protected from digestion. This is typically accomplished either by complexing the vaccines with a composition to render it resistant to acidic and enzymatic hydrolysis or by packaging the vaccines in an appropriately resistant carrier such as a liposome or enteric coated capsules. Means of protecting the attenuated bacteria or antigen from digestion are well known in the art. The pharmaceutical compositions can be encapsulated, e.g., in liposomes, or in a formulation that provides for slow release of the active ingredient.

The vaccines, alone or in combination with other suitable components, can be made into aerosol formulations (e.g., they can be "nebulized") to be administered via inhalation. Aerosol formulations can be placed into pressurized acceptable propellants, such as dichlorodifluoromethane, propane, nitrogen, and the like.

The dose administered to a subject, in the context of the disclosure should be sufficient to effect a beneficial therapeutic and/or prophylactic response in the subject over time. The dose will be determined by the efficacy of the particular vaccine employed and the condition of the subject, as well as the body weight or vascular surface area of the subject to be treated. The size of the dose also will be determined by the existence, nature, and extent of any adverse side-effects that accompany the administration of a particular vaccine in a particular subject.

In determining the effective amount of the vaccine to be administered in the treatment or prophylaxis of an infection or other condition, the physician evaluates vaccine toxicities, progression of the disease, and the production of anti-vaccine antibodies, if any.

The compositions are administered to a subject that is at risk from acquiring an infection caused by P. acnes or to prevent or at least partially arrest the development of the infection and its complications. An amount adequate to accomplish this is defined as a "therapeutically effective dose" or "therapeutic effective amount." Amounts effective for therapeutic use will depend on, e.g., the antigen composition, the manner of administration, the weight and general state of health of the subject, and the judgment of the prescribing physician. Single or multiple doses of the antigen compositions may be administered depending on the dosage and frequency required and tolerated by the subject, and route of administration. In addition, a booster may be administered in the same or different formulation. For example, the method contemplates administration of a first composition comprising a P. acnes antigen in an attenuated bacterial vector and a second composition comprising a P. acnes antigen in an attenuated non-bacterial vector. The second composition may be administered simultaneously or subsequent to administration of the first immunogenic composition.

In particular embodiments, a therapeutically effective dose of the immunoprotective composition is administered to a subject. Amounts of live attenuated bacteria or non-bacteria expressing the P. acnes or other antigens present in the initial immunization generally range from about $5 \times 10^5$ to $5 \times 10^{11}$ organisms per subject, and more commonly from about $5 \times 10^8$ to $5 \times 10^9$ organisms per subject.

The immunoprotective compositions are typically administered to an individual that is immunologically naive with respect to P. acnes. Usually, 2-4 doses of an immunological composition of the disclosure may be sufficient, however additional doses may be required to achieve a high level of immunity. Additional booster doses may be given every 1-5 years, as necessary, to maintain a high level of immunity.

In general, administration to any individual should begin prior to the first sign of disease, or possibly at the first sign of possible or actual exposure to P. acnes.

The vaccines of the disclosure can be packaged in packs, dispenser devices, and kits for administering vaccines to a mammal. For example, packs or dispenser devices that contain one or more unit dosage forms are provided. Typically, instructions for administration of the compounds will be provided with the packaging, along with a suitable indication on the label that the compound is suitable for treatment of an indicated condition. For example, the label may state that the active compound within the packaging is useful for treating a particular infectious disease or for preventing or treating other diseases or conditions that are mediated by, or potentially susceptible to, a mammalian immune response.

The following specific examples are meant to be illustrative and non-limiting. Those of skill in the art will recognize various modification and substitutions that can be made in the compositions and methods that follow. Such modification and substitutions do not depart from the disclosure and are encompassed herein.

EXAMPLES

Figure 2:
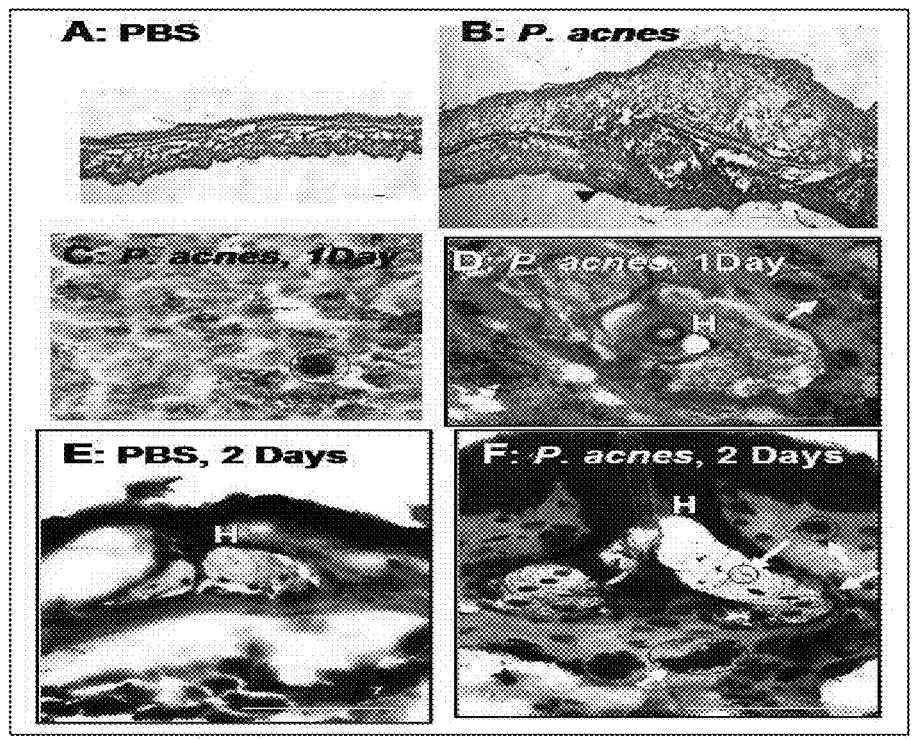
FIG. 2A-F show *P. acnes* induces gramulomatous response and colonizes in the root of hair follicle. H&E staining demonstrated that injection with *P. acnes* ($10^8$ CFU) into mouse ears for one day increased ear thickness and caused a granulomatouse response (arrowhead) (B). PBS injection serves as a control (A). The area of granulomatouse response was stained with Accustain Gram stain (a gram-positive bacteria staining kit) (Sigma, St. Louis, Mo.). *P. acnes* (circle; stained in purple) was surrounded by a densely packed granulomatous infiltrate (C) one day after injection. There is no *P. acnes* accumulated in hair follicle (D) one day after injection. However, two days after injection, *P. acnes* (circles and arrows) migrated to hair follicle and colonized in the root follicle (F). Histology of hair follicle from mice injected with PBS for two days were illustrated as a control (E). Bars: 100 µm.

The disclosure indicates that injection of P. acnes (ATCC 6919; $10^8$ CFU) into ICR mouse ears induced an increase in the ear thickness (FIG. 1) and gramulomatous response (FIG. 2A, B). One day after injection, P. acnes was surrounded by a densely packed granulomatous infiltrate (FIG. 2C). P. acnes immigrated to hair follicles and aggregated in the sebaceous glands two days after injection (FIG. 2 D, E). Although ears injected with S. epidermidis (ATCC 12228; $10^8$ CFU) had a minor swelling, this swelling can be rapidly subsided within four days. Thus, the disclosure provides a model for measurement and testing of agents that effect P. acnes. For example, the mouse ear model of the disclosure can be used to test the cytotoxicities of virulence factors of P. acnes. Additionally, the model is useful for evaluating the anti-inflammatory effects of P. acnes vaccines.

When P. acnes is grown on a sheep blood agar plate in close proximity to beta-hemolytic microorganisms, such as Staphylococcus aureus (S. aureus) and Clostridium perfringens, it synergistically enhances hemolysis similar to the classical Christie, Atkins, Munch-Peterson (CAMP). CAMP reactions are induced by the combination of CAMP factor co-hemolysin, which is a pore-forming toxin, and sphingomyelinase (SMase) derived from the other bacterial partner. CAMP factor itself has only weak hemolytic activity on the erythrocytes, but pretreating the cells with SMase enhances its activity. The entire genomic sequence of P. acnes includes numerous genes whose products are involved in degrading host molecules, and five genes encoding CAMP factor homologs of Streptococcus agalactiae (S. agalactiae) have been found in the genome information. This analysis of P. acnes proteins by a proteomic technique utilizing isotope-coded protein labels coupled to NanoLC-MS analysis revealed that one of the CAMP factor homologs (accession number: gi/50842175, incorporated herein by reference), showing 42% identity in nucleotide sequence to the S. agalactiae CAMP factor, is produced at higher concentrations by bacteria cultured under anaerobic condition than under aerobic conditions. These data suggest a physiological significance for the CAMP factor for P. acnes.

SMases have been widely isolated and characterized from bacteria, yeast, and various tissues and biological fluids of mammalians. In spite of low identity between bacterial and mammalian SMases, the amino acid sequences share a number of conserved residues, suggesting a common catalytic mechanism. The disclosure demonstrates that P. acnes benefits from a host SMase that amplifies its CAMP factor-mediated pathogenicity. The disclosure show a host SMase in CAMP factor-mediated pathogenicity of P. acnes both in vitro and in vivo, and the synergistic potential of a vaccine treatment targeting CAMP factor and local injection with IgG against a host SMase in P. acnes-associated inflammatory acne vulgaris.

Figure 3:
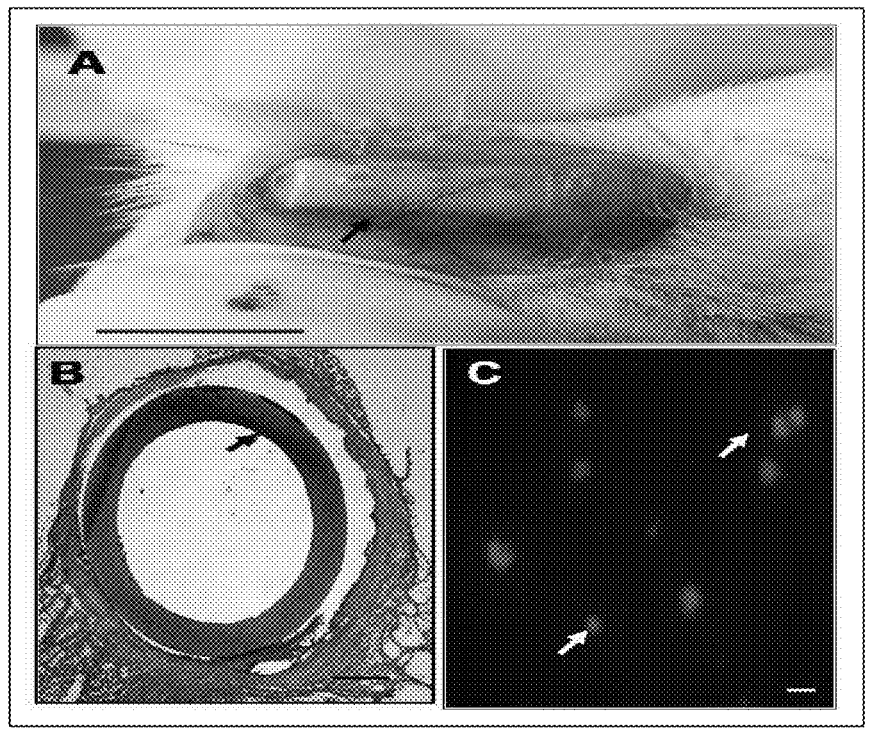
FIG. 3A-C shows implantation of tissue chambers and phagocytes in tissue chamber fluids. A tissue chamber (internal and external diameters, 1.5 and 3 mm, respectively, length, 1 cm; internal volume, 80 µl) was subcutaneously implanted into abdominal skin (A) of ICR mice for 7 days before bacteria injection. The tissue chamber consisted of closed ploytetrafluoroethylene Teflon cylinders with 12 regularly spaced 0.1 mm holes. Bar: 1 cm. H&E staining showed that mouse tissues wrapped a tissue chamber after 7-day implantation (B). Bar: 1.0 mm. Tissue chamber fluids were drawn by pecutaneous aspiration. After centrifugation, infiltrated cells (phagocytes) were stained with nucleus dye Hoechst 33258 (C). Arrows indicated phagocytes in tissue chamber fluids. Bar: 5 µm.

A tissue chamber model was used to detect pro-inflammatory cytokines and bacterial growth. The tissue chamber model was first described and extensively characterized in the guinea pig and then adapted to the mouse. This model accurately mimics bacterial infections in vivo. Because bacteria are inoculated directly into the chamber, with no adherence and invasion step through epithelia, the minimal infective dose of P. acnes which is required for a persistent infection reflects virulence. The host response is mediated exclusively by phagocytes and comprises antimicrobial peptides, cytokines, chemokines, leukocyte infiltration, and apoptosis. A tissue chamber model was utilized to evaluate the efficacy of anti-P. acnes vaccines. A tissue chamber (FIG. 3) was subcutaneously implanted into abdominal skin of ICR mice for 7 days.

Figure 4:
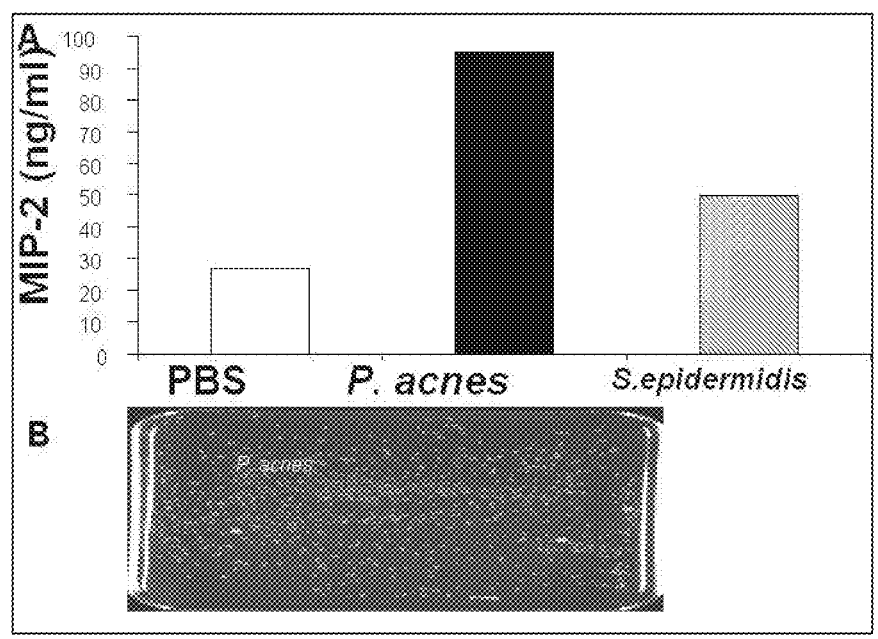
FIG. 4A-B shows detection of macrophage-inflammatory protein (MIP)-2 concentration and *P. acnes* growth in tissue chamber fluids. After implantation of tissue chambers for 7 days, *P. acnes*, *S. epidermidis* (20 µl; $10^7$ CFU) or PBS (20 µl) were injected into tissue chambers. Sampling tissue chamber fluids was performed 3 days after bacterial injection. Measurement of MIP-2 in the supernatants of fluids was carried out by sandwich ELISA that used the Quantikine M mouse MIP-2 set (R&D System, Minneapolis, Minn.) (A). In vivo *P. acnes* growth was detected by spreading the tissue chamber fluids on MHB agar plates to quantify CFU (B).

After implantation of tissue chambers, P. acnes, S. epidermidis (20 µl; $10^7$ CFU) or PBS (50 µl) were injected into tissue chambers. Three days after bacterial injection, tissue chamber fluids were harvested for detection of macrophage-inflammatory protein (MIP)-2. Compared with PBS-injected mice, the level of MIP-2 was significantly increased by three and two folds in P. acnes- and S. epidermidis-injected mice, respectively (FIG. 4A). In vivo survival (colonies) of P. acnes can be detected on MHB agar plates after spreading the tissue chamber fluids on plates (FIG. 4B).

Figure 5:
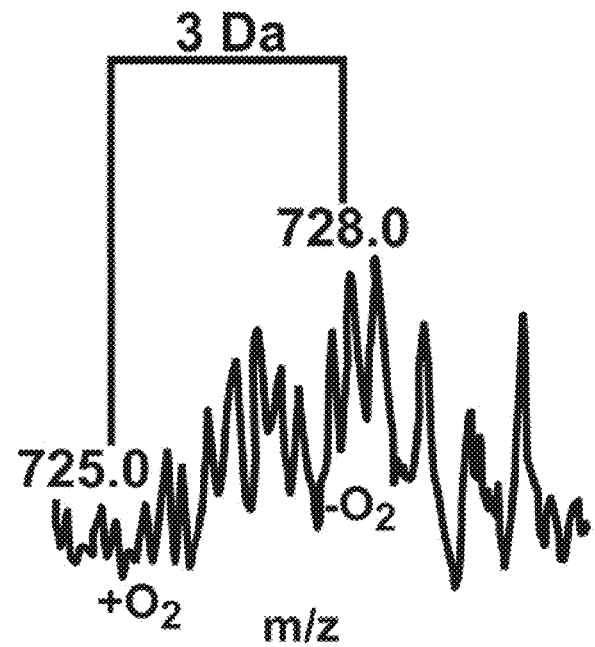
FIG. 5A-D shows quantitative analysis of *P. acnes* proteome alterations using isotope-coded protein labels (ICPL): Identification of CAMP factor and lipase. *P. acnes* was grown under aerobic and anaerobic conditions. Lysates (1 mg) of *P. acnes* from aerobic and anaerobic growth were labeled with ICPL tags, $C^{12}$—N-nicotinoyloxy-succinimide (Nic-NHS) and $C^{13}$-Nic-NHS, respectively. All lysine side chains of proteins in lysates were modified selectively. After mixing $C^{12}$-Nic-NHS- with $C^{13}$-Nic-NHS-labeled samples, the mixture was subjected to a LTQ mass spectrometer (Thermo Electron Corp. Waltham, Mass.) for protein identification and quantification. Two-tag labeling introduced a mass difference of 6 Da per labeled site in mass spectra. More than 300 proteins of *P. acnes* were identified. 23 proteins were either up- or down-regulated under anaerobic or aerobic conditions (Table 1). Two secretory virulence factors (lipase and CAMP factor) with double charges and 3 Da mass differences were shown (A and B). Both of the virulence factors have a higher expression in *P. acnes* under anaerobic conditions. Two peptides (SYSEKHLGVAFR (SEQ ID NO:1) and DLLKAAFDLR (SEQ ID NO:2)) were sequenced and assigned to the internal peptides of lipase (C) and CAMP factor (D), respectively.
Figure 5:
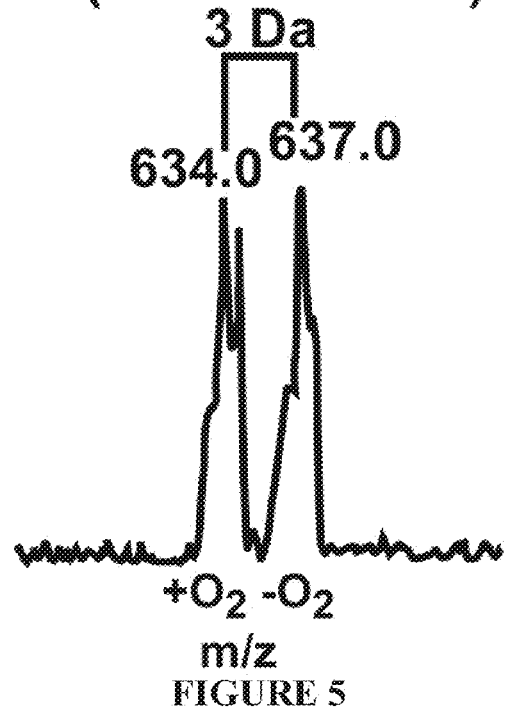
Figure 5:
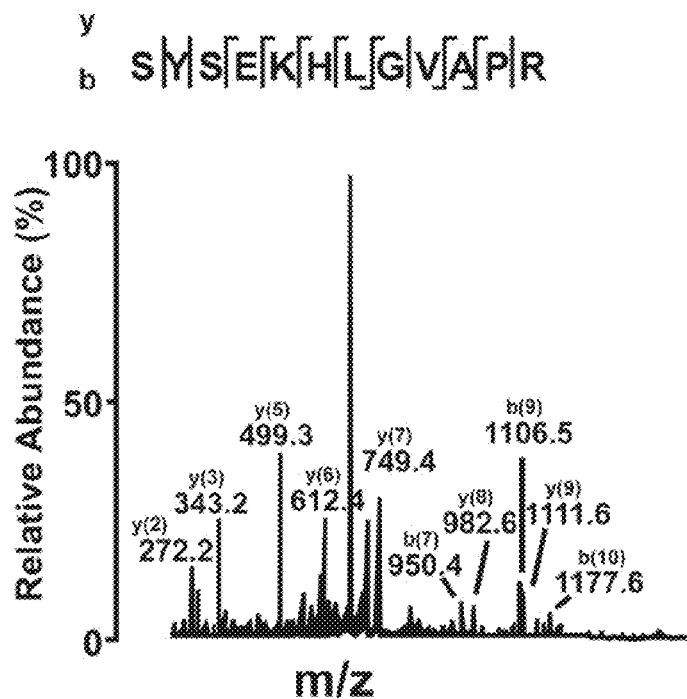
Figure 5:
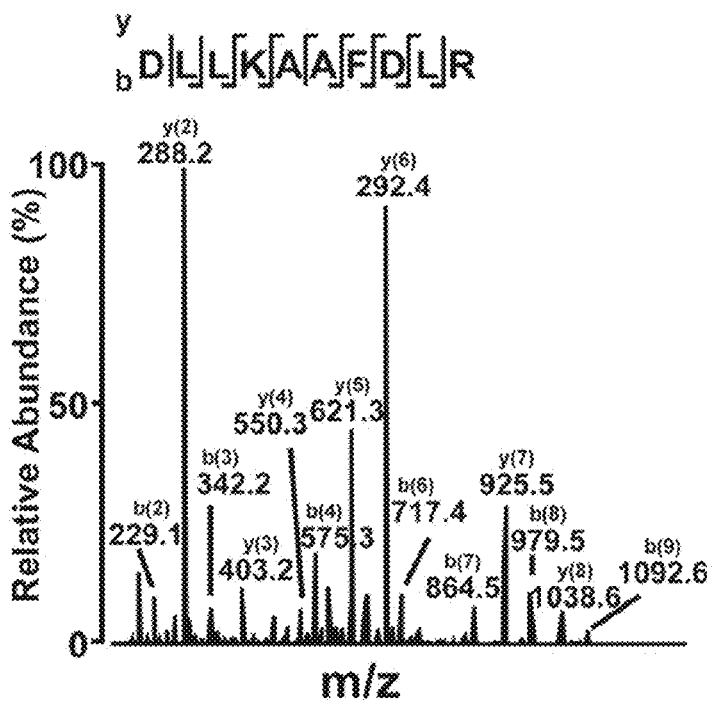

In humans P. acnes multiplies in anaerobic environment where sebum accumulate in clogged follicles. It has been demonstrated that the level of lipase production was increased markedly by P. acnes in the absence of oxygen. In an effort to identify the virulence factors which were highly expressed under anaerobic conditions, a comprehensive quantitative proteome analysis was performed on P. acnes in the presence or absence of oxygen. Identified virulence factors were selected as P. acnes vaccine candidates. Changes in the abundances of individual protein species in $O_2$-grown P. acnes as compared to no-$O_2$-grown P. acnes were analyzed using a nongel-based isotope-coded protein label (ICPL) method. 342 P. acnes proteins were identified and sequenced by LTQ MS/MS. 152 of 342 proteins were successfully labeled with ICPL. 23 proteins were identified as up- or down-regulated under anaerobic or aerobic conditions (Table 1). Two secretory virulence factors (CAMP factor and lipase) were highly expressed under anaerobic conditions (FIGS. 5A and B). Two internal peptides (SYSEKHLGVAFR (SEQ ID NO:1) and DLLKAAFDLR (SEQ ID NO:2)) of lipase and CAMP factor were presented, respectively (FIGS. 5C and D). Although it is well known that lipase is involved in the pathogenesis of acne lesions, the role of CAMP factor in acne development is totally unknown. More recently, it was reported that CAMP factor of Streptococcus agalactiae behaved as a pore-forming toxin. Thus CAMP factor was selected as a target for the development of P. acnes vaccines.

Treatment of sialidase increases the susceptibility of human sebocytes to P. acnes. A variety of sialidases have been uncovered in the genome of *P. acnes*. Three sialidases were selected from *P. acnes* genome for cloning, including a cell wall-anchored sialidase (accession # gi|50843035; (SEQ ID NO:12 and 13, polynucleotide and polypeptide, respectively), a secreted sialidase B (accession# gi|50842171; SEQ ID NO:14 and 15, polynucleotide and polypeptide, respectively) and a sialidase-like protein (accession# gi|50843043; SEQ ID NO:16 and 17, polynucleotide and polypeptide, respectively). The cell wall-anchored sialidase (accession # gi|50843035) exhibits the strongest enzyme activity in removing the sialic acids from the surface of human SZ95 sebocytes. In addition, the selected *P. acnes* sialidase is a surface protein that potentially serves as an excellent target for vaccine development. Thus, this protein was selected to investigate immunogenicity. The cell wall-anchored sialidase contains an LPXTG cell wall-anchoring motif in the C-terminal domain. Although it is known that sialidase of *P. acnes* shares identities (~30%) with sialidase (EC 3.2.1.18) (accession#Q02834) of *Micromonospora viridifaciens* and a cell wall surface anchor family protein (accession# Q04M99) of *Streptococcus pneumoniae* serotype 2, the immunogenicity of sialidase of *P. acnes* was unexplored.

A gene encoding sialidase was PCR amplified from template DNA prepared from *P. acnes*. Specific primers including the sense and anti-sense primer were designed. The PCR products were inserted into a pEcoli-Nterm 6×HN plasmid and expressed in *E. coli* [*E. coli* BL21 (DE3)]. After IPTG induction, over-expressed sialidase-6×NH fusion protein from *E. coli* was detected in a Coomassie blue stained SDS-PAGE gel at approximately 53.1 kDa molecular weight. The sialidase-6×NH fusion protein was purified using a TALON resin column. The sialidase expression was confirmed by Matrix Assisted Laser Desorption Ionisation—Time of Flight (MALDI-TOF MS) as well as NanoLC-MS/MS sequencing. Purified sialidase-6×NH fusion protein was in-gel digested with trypsin prior to NanoLC-MS/MS analysis. Nineteen internal peptides derived from sialidase were fully sequenced by NanoLC-MS/MS analysis via an HCTultra PTM system ion trap mass spectrometer. The MS/MS spectra of sequenced peptides matched well with those of sialidase (accession # gi|50843035) of *P. acnes*. An internal peptide (VVELSDGTLMLNSR; 316-329 amino acid residue of SEQ ID NO:13) of sialidase was present. These results indicate that sialidase was expressed in *E. coli* BL21 (DE3) and suggest that mass spectrometry provided a powerful modality to confirm the expression of a protein that has no antibody available for western blot.

Figure 6:
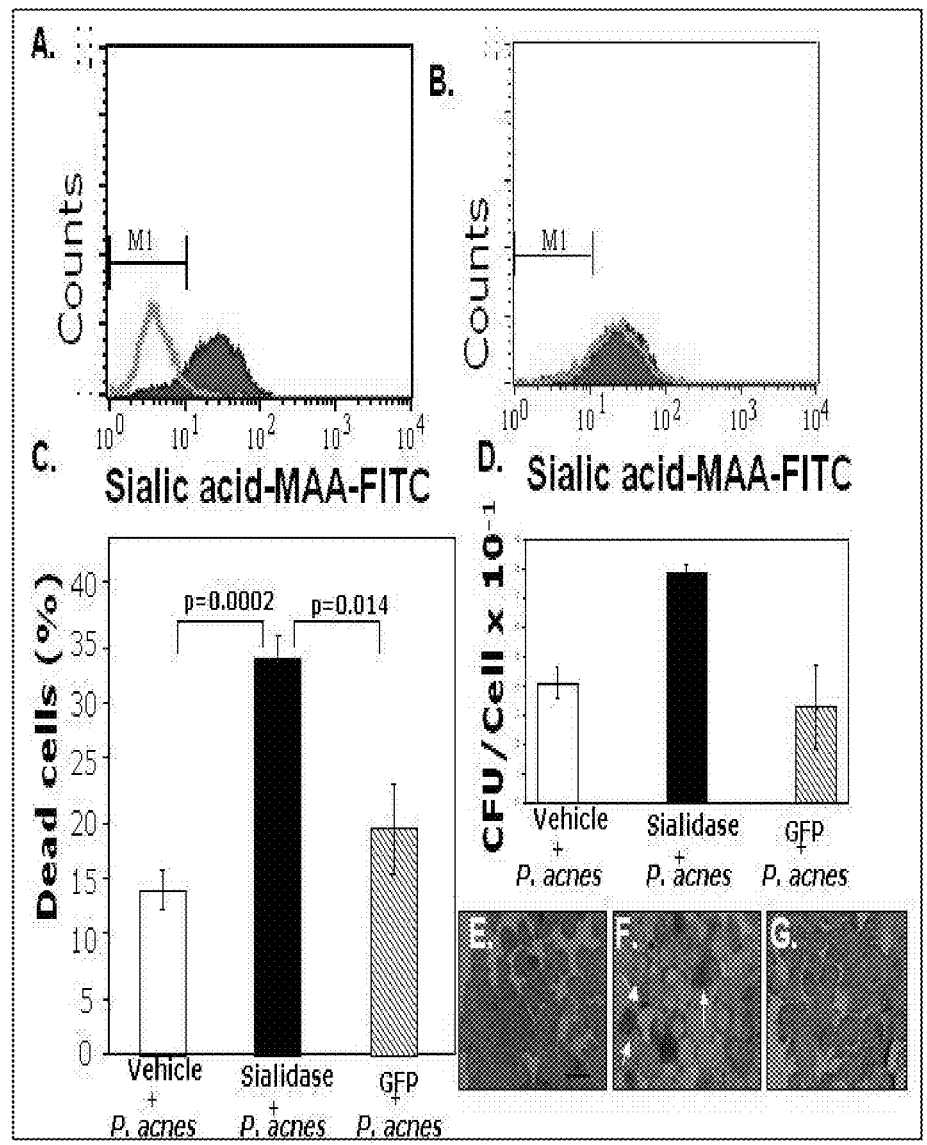
FIG. 6A-G shows removal of sialic acids by sialidase increases the susceptibility of human sebocytes to *P. acnes*. Sialic acids on the cell surface of immortalized human sebocytes (SZ95) were detected by the reaction with biotinylated Maackia Amurensis (MAA) lectin I (10 µg/ml) and streptavidin-FITC conjugate. The FITC-fluorescence intensity was counted by flow cytometry to reflect the level of sialic acids (A). The sebocytes were pre-treated with PBS (vehicle), sialidase (10 µg/ml) (grean, A), or GFP (10 µg/ml) (B) at pH 6 for 2 h. The decrease of the FITC-fluorescence intensity in sialidase-treated sebocytes indicated that pureed sialidase is an effective enzyme. After pretreatment of sialidase (10 µg/ml, 2 h), sebocytes were co-cultured with *P. acnes* ($10^7$ CFU/$10^6$ cells) for 24 h. *P. acnes*-induced cell death in vehicle-, sialidase- or GFP-treated sebocytes were counted by trypan blue staining (C). After washing out with suspended *P. acnes*, the number of *P. acnes* adhered to sebocytes was calculated by spreading trypsinized sebocytes on MHB agar plates to quantify CFU/cells (D). The adherence of *P. acnes* into vehicle (E), sialidase (F, arrows) or GFP (G)-treated sebocytes was visualized by staining with Accustain Gram stain kit.

To determine the enzyme activity, purified sialidase-6×NH fusion protein (10 μg/ml) was added to human SZ95 sebocyte culture for 2 h to remove the sialic acids on the surface of sebocytes. The amount of surface sialic acids was determined by flow cytometry (FACSCalibur, BD Biosciences, San Jose, Calif.) using the reaction of biotinylated Maackia Amurensis lectin I and streptavidin-FITC conjugate. The fluorescence of MAA labeled-sailic acids in sialidase-treated sebocytes was dramatically decreased by 63% (FIG. 6A), whereas the fluorescence in GFP-treated sebocytes was unchanged (FIG. 6B). The data indicated that purified sialidase retained an enzyme activity. After treatment with sialidase (10 μg/ml) for 2 h, sebocytes ($10^6$ cells) were exposed to live *P. acnes* ($10^7$ CUF) overnight. Live *P. acnes* induced an approximately 15~20% of cell death in untreated or GFP-treated sebocytes. However, the *P. acnes*-induced cell death in sialidase-treated sebocytes was significantly increased by 35% (FIG. 6C), demonstrating that the treatment of sialidase increases the susceptibility of sebocytes to *P. acnes*. It has been demonstrated that incubation of human buccal epithelial cells with the sialidase significantly increased *Pseudomonas aeruginosa* adherence. The adherence of *P. acnes* into sialidase-treated sebocytes was examined. The results showed that pre-treatment with sialidase (10 μg/ml for 2 h), but not GFP, considerably increased the adherence of *P. acnes* into sebocytes (FIG. 6D). Accustain Gram stains indicated that the number of *P. acnes* interacted with sebocytes was increased once surface sialic acids of sebocytes were removed by sialidase (FIG. 6E-G). Therefore inhibiting the activity of sialidase or neutralizing sialidase by antibodies, siRNA, small molecules inhibitors the bind the active site, antisense and the like can be useful in providing protection against *P. acnes* infection. Antisense molecules can be generated based upon the polynucleotide sequences provided herein.

The intact particle of *E. coli* has been used as a vector for intranasal and epicutaneous vaccination. To engineer *E. coli* vector-based vaccines targeting an anthrax spore coat associated protein (SCAP), a gene encoded SCAP was constructed into the pET15b vector (EMD Biosciences, Inc.). After IPTG induction, *E. coli* carrying either an empty expression vector or SCAP expression plasmid were killed by UV irradiation. For immunization, the UV-irradiated *E. coli* vector-based vaccine, not mixed with exogenous adjuvants, was then directly administered into the nasal cavity of mice. Sera harvested from each group (n=4) of mice three weeks after immunization was pooled. The production of anti-SCAP IgG was detected by an antigen array. The antigen microarray was created by spotting with recombinant SCAP, maltose binding protein (MBP)-tagged SCAP, and mouse IgG (positive controls). The sera from mice immunized with an empty expression vector and an *E. coli* vector with SCAP over-expression were hybridized on arrays. While the negative control yielded only background signals, the positive control (IgG) generated a dilution-dependent signal reduction. The experiment showed that anti-SCAP antibody was produced after immunization with *E. coli* vector-based vaccine (*E. coli* BL21 (DE3) T7/lacO SCAP) by comparing to control serum. More importantly, the anti-SCAP antibody can be produced without boosting.

Figure 7:
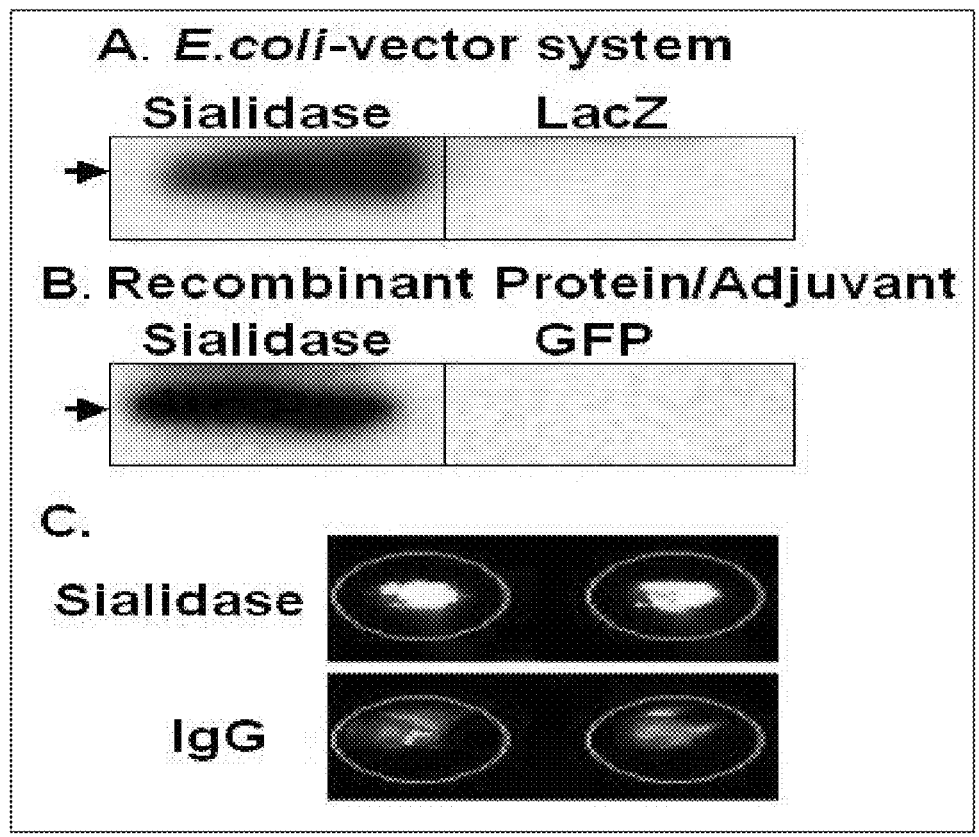
FIG. 7A-C shows that sialidase is immunogenic when mice were immunized with an *E. coli* vector-based vaccine or recombinant protein/Freund (in)complete adjuvants. The irradiated *E. coli* vector-based vaccine (*E. coli* BL21 (DE3) T7/lacO sialidase) was constructed by inserting PCR products of sialidase into the pEcoli-Nterm 6×HN vector (Clontech). The production of antibody *E. coli* vector ($10^9$ CFU)-immunized mice was detected by western blot analysis 6 weeks after vaccination (A). Mice immunized with *E. coli*-empty vector (lacZ) serve as negative controls. ICR mice were also immunized with a recombinant sialidase-6×NH fusion protein or GFP using Freund/(in)complete adjuvants. For the subcutaneous vaccination at first injection, mice were inoculated with 200 μg of the sialidase-6×NH fusion protein or GFP which was emulsified with a complete Freund adjuvant. Two weeks after injection, the second injection was performed. Mice were intramuscularly injected with the same amount of antigens which were mixed well with an incomplete Freund adjuvant. Anti-sialidase antibody was detected by western blot (B) and antigen microarrays (C) one week after second vaccination. 0.35 μg of purified sialidase-6×NH fusion protein and IgG indicated were spotted twice on antigen microarrays. Data is representative of three separate experiments with similar results. Sialidase antibodies can be provoked when mice were immunized with both *E. coli*-vector-based vaccines and recombinant proteins/Freund adjuvants.

A gene encoded SCAP was also constructed into the pCAL-n-FLAG vector (FIG. 7C) followed by transformation into the *E. coli* BL21 strain which served as the antigen carrier. For safety concerns, transformed *E. coli* was destructed by gamma irradiation. ICR mice were immunized via intranasal administration with irradiated *E. coli* vectors encoding SCAP. Antibody production was measured via western blot by reaction with serum obtained from one month post-immunized mice. Mice were able to produce detectable levels of antibody to SCAP without any boost. Pretreatment of a nonionic surfactant (tetradecyl-β-D-maltoside; TDM) (Antatrace Inc., Maumee, Ohio) on the skin surface of ICR mice at a concentration of 0.125% (in sterile water) for 15 min slightly disrupts the stratum corneum barrier but greatly enhances the epicutaneous immunization of *E. coli* based-tetanus toxin C fragment vaccine (*E. coli* BL21 nir/B tetC). Pretreatment of TDM (0.125%) on the skin surface of ICR mice for 15 min, followed by washing and then the epicutaneous application of irradiated *E. coli* vectoring SCAP, these mice can produce an antibody response to SCAP. Antibody production was measured via western blot by reaction with serum obtained from one month post-immunized mice. Mice were able to produce detectable levels of antibody to SCAP without any boost. These results demonstrate that SCAP is an immunogenic anthrax protein when mice were non-invasively immunized with *E. coli* vector-based vaccines. The results demonstrated that TDM can disrupt the stratum corneum barrier of the skin which significantly potentiates skin immunity. The disclosure thus provides an immunization protocol to immunize with CAMP factor and sialidase.

A UV-irradiated *E. coli* vector-based vaccine [*E. coli* BL21 (DE3) T7/lacO Sialidase] was used to test the immunogenicity of *P. acnes* sialidase (accession # gi|50843035). A dose of UV (4,500 J/m$^2$) was given to irradiate all *E. coli*, both expressing (a Sialidase-vector) and not expressing Sialidase genes (a LacZ-empty vector), as demonstrated by the inability to form colonies on LB agar plates. The amount of sialidase in *E. coli* vectors was not changed after UV-irradiation. ICR mice were intranasally immunized with UV-irradiated *E. coli* BL21 (DE3) T7/lacO Sialidase and boosted 3 weeks after the first nasal inoculation. The production of antibody (IgG) in mouse sera was detected 3 and 6 weeks after immunization by western blot. A strong band appearing at approximately 53.1 kDa was visualized when a sialidase-6xNH fusion protein transferred membrane was reacted with mouse serum harvested 6 weeks after immunization. No sialidase-reacted antibody production was found in LacZ-empty vector-immunized mice. ICR mice were also immunized with sialidase-6xNH fusion protein or GFP using Freund/(in)complete adjuvants. The antibody production was detected by western blot analysis three weeks after immunization. A strong band appearing at 53.1 kDa was visualized when the sialidase-6xNH fusion protein was reacted with serum from sialidase-immunized mice. The antibody production was also confirmed by antigen microarray. An antigen microarray was created by printing with sialidase-6xNH fusion protein and mouse IgG (a positive control). After hybridization with mouse sera, fluorescent signals displayed in antigen microarrays indicated sialidase antibody production. The sialidase antibody was detectable in the serum harvested from mice three week after immunization. No sialidase-reacted antibody production was found in GFP-immunized mice. Data from both antigen microarray and western blot confirmed that sialidase was an immunogenic protein.

Protective Immunity of Sialidase-Based Vaccines to *P. Acnes*-Induced Inflammation.

Figure 8:
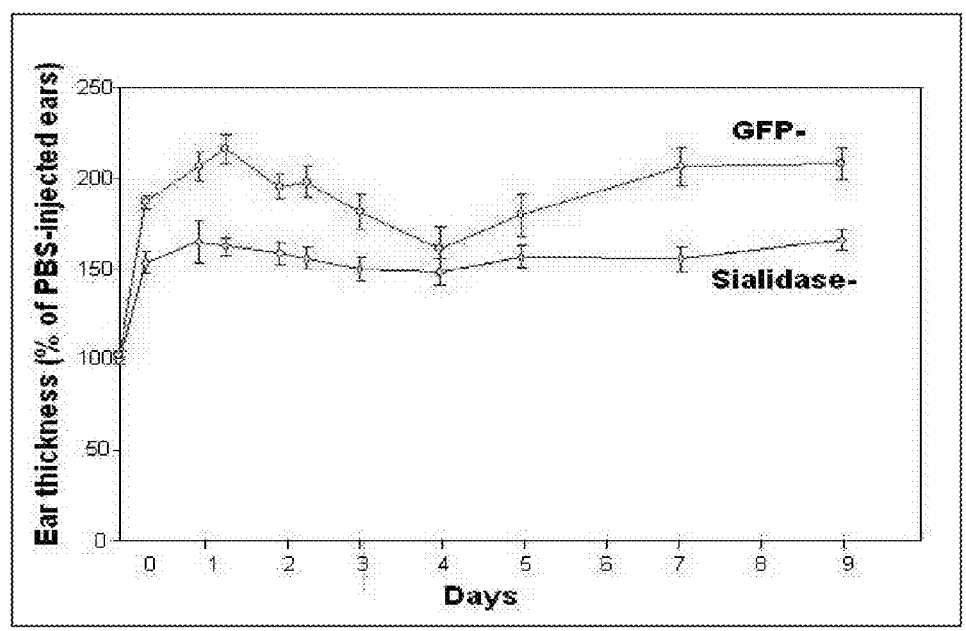
FIG. 8 shows protective immunity of a sialidase-based vaccine to *P. acnes*-induced ear thickness. ICR mice were immunized with recombinant sialidase-6×NH fusion protein or GFP using Freund (In)complete adjuvants. After confirmation of antibody production by western blot, *P. acnes* ($10^7$ CFU, 25 μl) was subcutaneously injected into ears of sialidase- and GFP-immunized mice. Injection of PBS (25 μl) served as a control. Ear thickness was measured for 9 days after injection and calculated as % of ear thickness in PBS-injected ears.

ICR mice immunized with recombinant proteins (sialidase or GFP) using Freund/(in)complete adjuvants (FIG. 8) were challenged with live *P. acnes* (10$^7$ CFU). Three weeks after vaccination, one ear of mouse was subcutaneously injected with 25 µl of *P. acnes* (10$^7$ CFU) and the other ear was injected with 25 µl of PBS as a control. Injection of *P. acnes* induced ear thickness and redness. Ear thickness was measured every day for 9 days. Ear thickness in GFP-immunized mice was rapidly elevated by more than two folds one day after *P. acnes* challenge. The elevation of ear thickness was significantly reduced by more than 50% when mice were immunized with sialidase (FIG. 8). The ear redness in GFP-immunized mice was subsided 7 days after *P. acnes* challenge, whereas the recovery of ear redness in sialidase-immunized mice was occurred 3 days after *P. acnes* challenge. These results indicated that sialidase-immunized mice suppressed *P. acnes*-induced ear inflammation. The production of *P. acnes*-induced pro-inflammatory cytokines were also measured after vaccination. A tissue chamber model (FIG. 3) was employed to detect the level of in vivo pro-inflammatory cytokines. A tissue chamber was subcutaneously implanted into abdominal skin of ICR mice 7 days before *P. acnes* (10$^7$ CFU) injection. The data indicated that tissue chamber fluid contains various immune cells including macrophages (CD11b$^+$, neutrophils (Gr-1$^+$), NK cells (CD49b$^+$) and T cells (CD3$^+$), suggesting an influx of immune cells into a tissue chamber. Three days after *P. acnes* injection, tissue chamber fluids containing pro-inflammatory cytokines were drawn by pecutaneous aspiration. The level of MIP-2 cytokine in immunized mice was measured by ELISA. In the GFP-immunized mice, a significant increase in MIP-2 level was observed 3 days after *P. acnes* injection. Importantly, the *P. acnes*-induced increase of MIP-2 cytokine was reduced by 61% in the sialidase-immunized mice. These results demonstrate that sialidase-based vaccines effectively decrease ear thickness and the production of pro-inflammatory cytokines in the mice.

Figure 9:
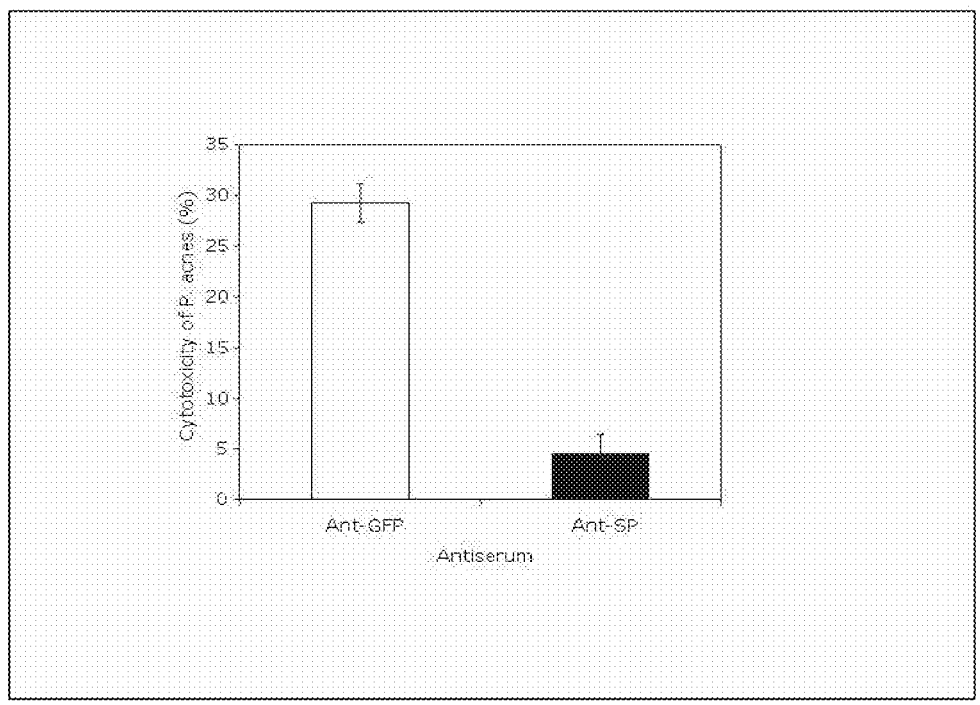
FIG. 9 shows anti-sialidase antiserum in vitro. *P. acnes* was pre-incubated with anti-sialidase antiserum for 2 h. The immortalized human sebocytes (SZ-95) were co-cultured with the antiserum-treated *P. acnes* 18 hr. After incubation, the cell death of sebocytes induced by cytotoxicity of *P. acnes* was determined with pNPP. The immortalized human sebocyte line, SZ95, was cultured on a 96-well plate until a density of $2 \times 10^5$ cells/well in Sebomed basal medium (Biochrom, Berlin, Germany) supplemented with 5 ng/ml human recombinant epidermal growth factor (Sigma, St. Louis, Mo.), 10% (v/v) heat-inactivated fetal bovine serum (Mediatech Inc., Herndon, Va.), at 37° C. under atmosphere of 5% (v/v) $CO_2$ in air. *P. acnes* were cultured as described above, washed with PBS by centrifuging. *P. acnes* were suspended to Sebomed basal medium containing 2.5% (v/v) anti-sialidase or anti-GFP (control) antiserum, and incubated at 37° C. for 2 h. The sebocytes were washed with PBS two times and then incubated with 100 μl of the neutralization reaction mixtures containing $2 \times 10^6$ CFU *P. acnes* and 2.5 μl antiserum for 18 h. As a control, an equal amount of PBS was added instead of *P. acnes*. As a background, Triton-X was added to get a final concentration of 0.1% (v/v) to kill sebocytes. After incubation, cytotoxicity of neutralizing mixture was determined with p-Nitrophenyl phosphate disodium (pNPP). The sebocytes were washed with PBS three times and incubated with 100 μl of 2.5% (w/v) pNPP in ACPI for 1 hr at 37° C. After incubation, 10 μl of 1N NaOH was added to stop the reaction and absorbance at 405 nm was measured. Cytotoxicity of neutralizing mixture was calculated as (no *P. acnes* group-*P. acnes* added group)-(no *P. acnes* group-back ground group)× 100.
Figure 10:
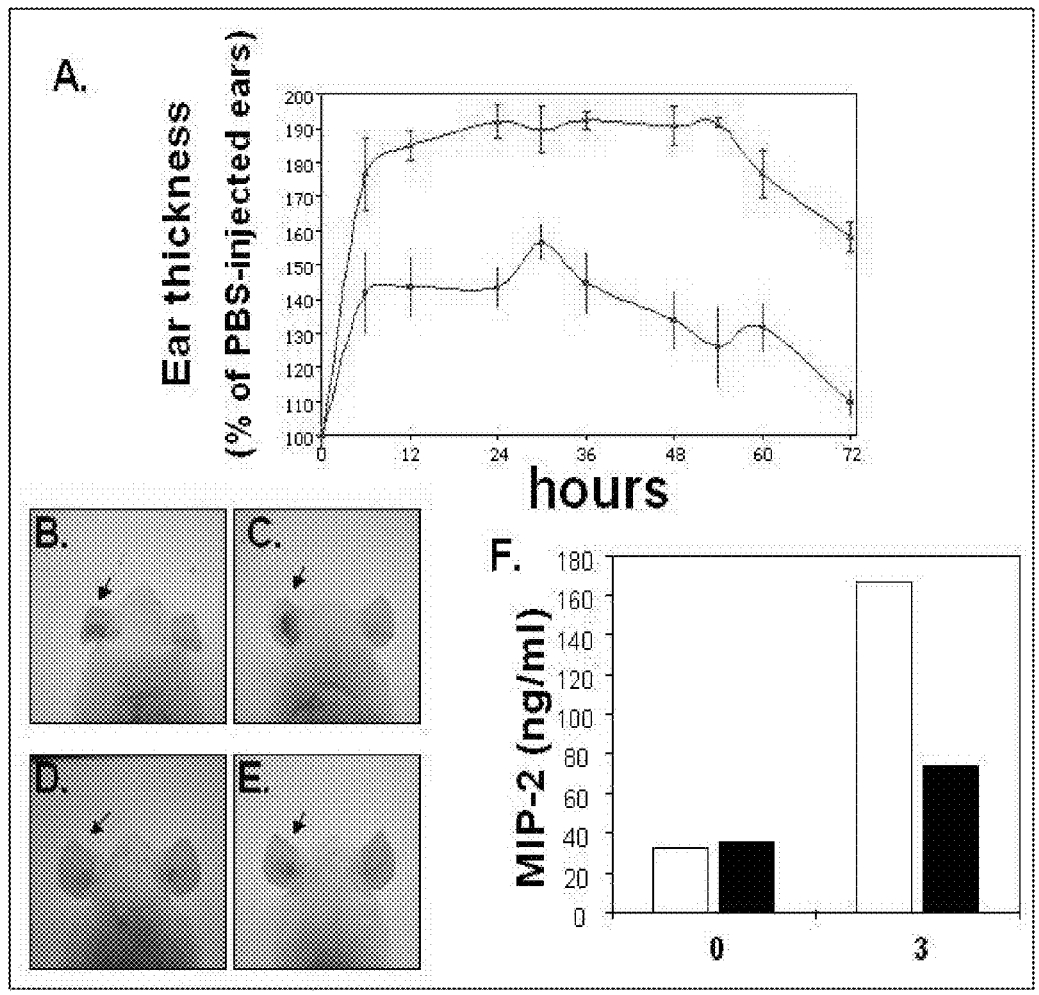
FIG. 10A-F shows protective immunity of an inactivated *P. acnes* vaccine. ICR mice were immunized with heat-killed *P. acnes* ($10^8$ CFU) and boosted twice at the three week intervals. Ten weeks (one week after second boost) after immunization, live *P. acnes* ($10^7$ CFU, 25 μl) or PBS (25 μl) was subcutaneously injected into ears of killed *P. acnes*-immunized and PBS-inoculated mice. Ear thickness was calculated as % of ear thickness in PBS-injected ears (A). 24 (B, C) and 72 h (D, E) after live *P. acnes* injection, the ear redness in killed *P. acnes*-immunized (B, D) and PBS-inoculated (C, E) mice was shown. Measurement of MIP-2 in the supernatants of fluids was conducted by sandwich ELISA. The elevation of MIP-2 induced by *P. acnes* (20 μl; $10^7$ CFU) injection was considerably suppressed in killed *P. acnes*-immunized mice (F).

Pretreatment of *P. acnes* with serum from sialidase-immunized mice significantly decreased the cytotoxicity of *P. acnes* to human sebocytes (FIG. 9). The culture of sebocytes with anti-GFP serum-treated *P. acnes* causes an approximately 30% of cell death, whereas the cell death of sebocytes was decreased to nearly 5% when cells were co-cultured with anti-sialidase serum-treated *P. acnes*. The results indicated that sialidase-immunized mice provoked antibodies that can effectively neutralize the cytotoxicity of *P. acnes* to human sebocytes.

Figure 11:
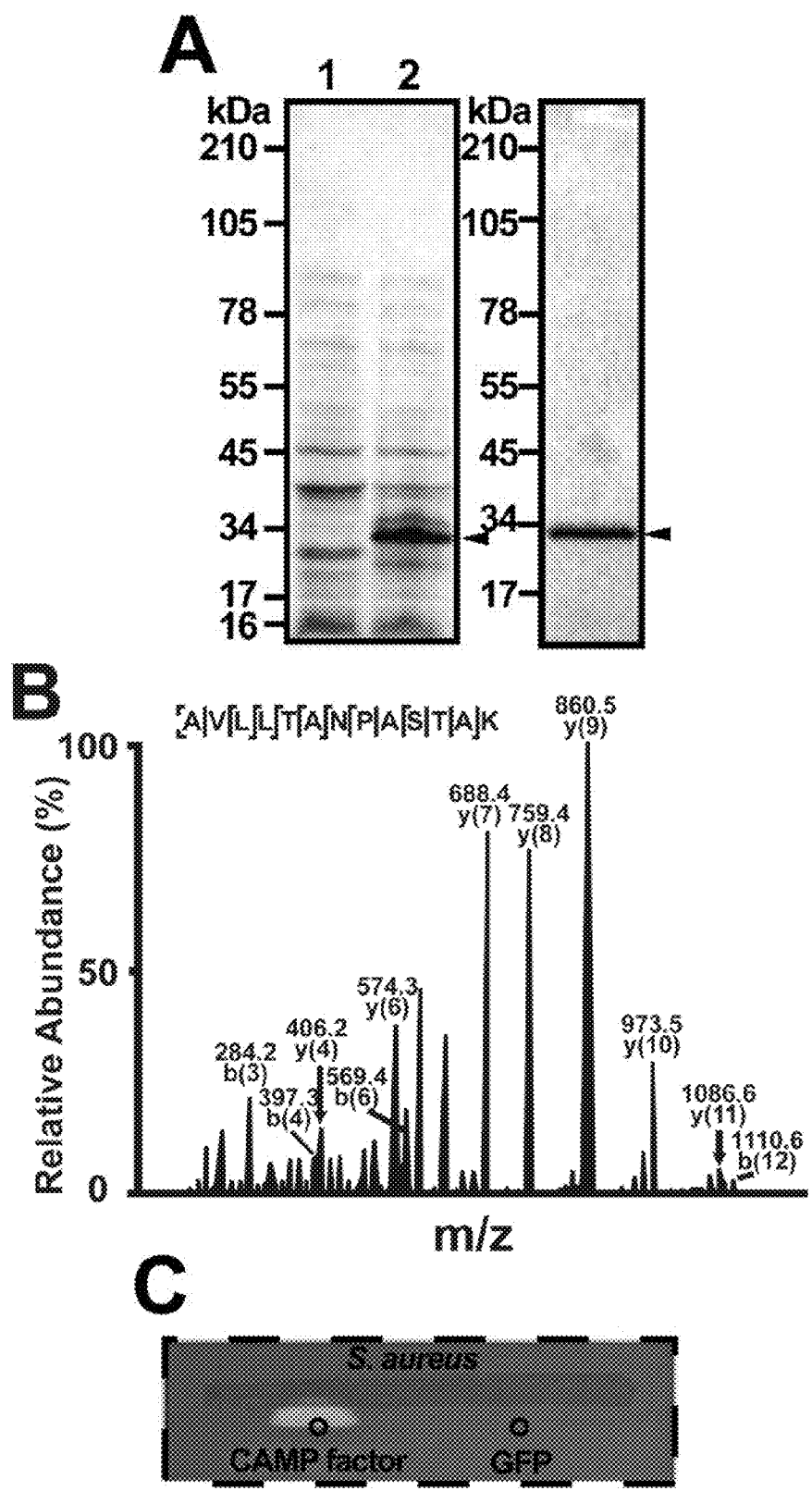
FIG. 11 shows characterization of *P. acnes* CAMP factor. (A) Recombinant *P. acnes* CAMP factor was expressed in *E. coli* (arrowhead). *E. coli* transformed with pEcoli-Nterm 6×HN vector containing a cDNA insert encoding CAMP factor was incubated without (lane 1) or with (lane 2) IPTG, disrupted, and separated by SDS-PAGE (10% acrylamide). Purified CAMP factor is shown on the right panel. (B) The expression and purity of CAMP factor was confirmed by NanoLTQ MS/MS mass spectrometry. A sequenced internal peptide (AVLLTANPASTAK; SEQ ID NO:3)) of CAMP factor is presented. (C) Co-hemolytic activity of recombinant CAMP factor was examined on a sheep blood agar plate. *S. aureus* strain 113 ($2 \times 10^5$ CFU/10 ul) was streaked on agar plate. Ten ul of recombinant CAMP factor (250 ug/ml) or GFP as a control protein (250 ug/ml) was spotted beside the *S. aureus* streak. (D) Immunogenicity of CAMP factor in ICR mice was evaluated by Western blot. Mice were intranasally vaccinated with UV-killed *E. coli* over-expressing CAMP factor or GFP. The mice were bled 14 days after the vaccination. Anti-CAMP factor (1:2,000 dilution; lanes 1 and 2) or anti-GFP antiserum (lanes 3 and 4) was reacted with recombinant CAMP factor (0.2 μg; lanes 1 and 3) or GFP (lanes 2 and 4). The immunoreactivity was detected with goat anti-mouse IgG (H+L)-HRP conjugate. (E) The titer of CAMP factor antibodies was determined by ELISA. The mice were bled 14, and 21 days after the vaccination with CAMP factor or GFP (n=10). The antisera (1:10,000 dilution) were reacted with CAMP factor immobilized on a microtiter ELISA plate. The captured antibodies were detected with goat-anti-mouse IgG (H+L)-HRP conjugate and OptEIA™ Reagent Set. The optical density of each well was measured at 450 nm. Horizontal bar represents average of 10 individual assays. (F) CAMP factor was detected in the supernatant of *P. acnes* culture by Western blotting. Recombinant CAMP factor (0.2 μg; lane 1) as a positive control, 10-fold concentrate of *P. acnes* culture supernatant (70 μg total protein; lane 2), and 10-fold concentrate of RCM (70 μg total protein; lane 3) as a negative control were separated by SDS-PAGE (10% acrylamide), transferred to a polyvinylidene fluoride membrane and reacted with mouse anti-CAMP factor antiserum (1:1,000 dilution, left panel) or anti-GFP antiserum (right panel). The 6×HN tag of recombinant CAMP factor was removed by enterokinase before loading into a SDS-PAGE. (G) Cytotoxicity of recombinant CAMP factor was examined in the human keratinocyte cell line (HaCaT) or murine macrophage cell line (RAW264.7). The cells ($1 \times 10^5$/well) were incubated with the indicated concentration of recombinant CAMP factor or GFP at 37° C. for 18 hr. After the incubation, cell viability was determined and cytotoxicity was calculated as described in Methods. The data represent mean±SE (n=6, $p<0.005$ and $p<0.0005$* by Student's t-test, vs. GFP control). (H) Intradermal injection with CAMP factor induced inflammatory reaction in ICR mouse ear. The left ear was intradermally injected with recombinant CAMP factor (10 μg/20 μl) or GFP (10 μg/20 μl) in PBS. Right ear received an equal amount of PBS (20 μl). The ear thickness was measured using a micro caliper 24 hr after the injection and changes reported as % of ear thickness in PBS-injected ears. The data represented as mean±SE (n=4, $p<0.005$** by Student's t-test).
Figure 11:
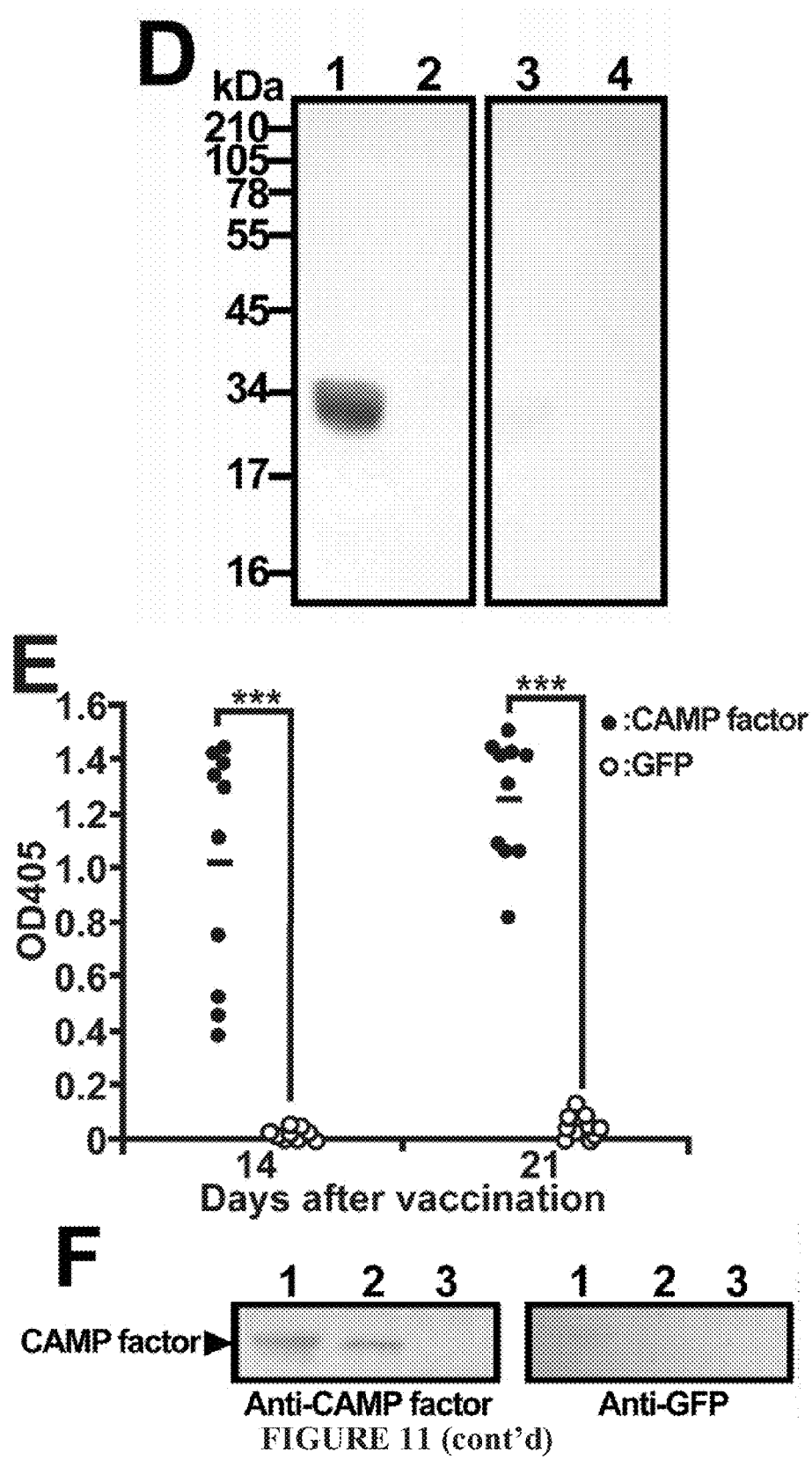
Figure 11:
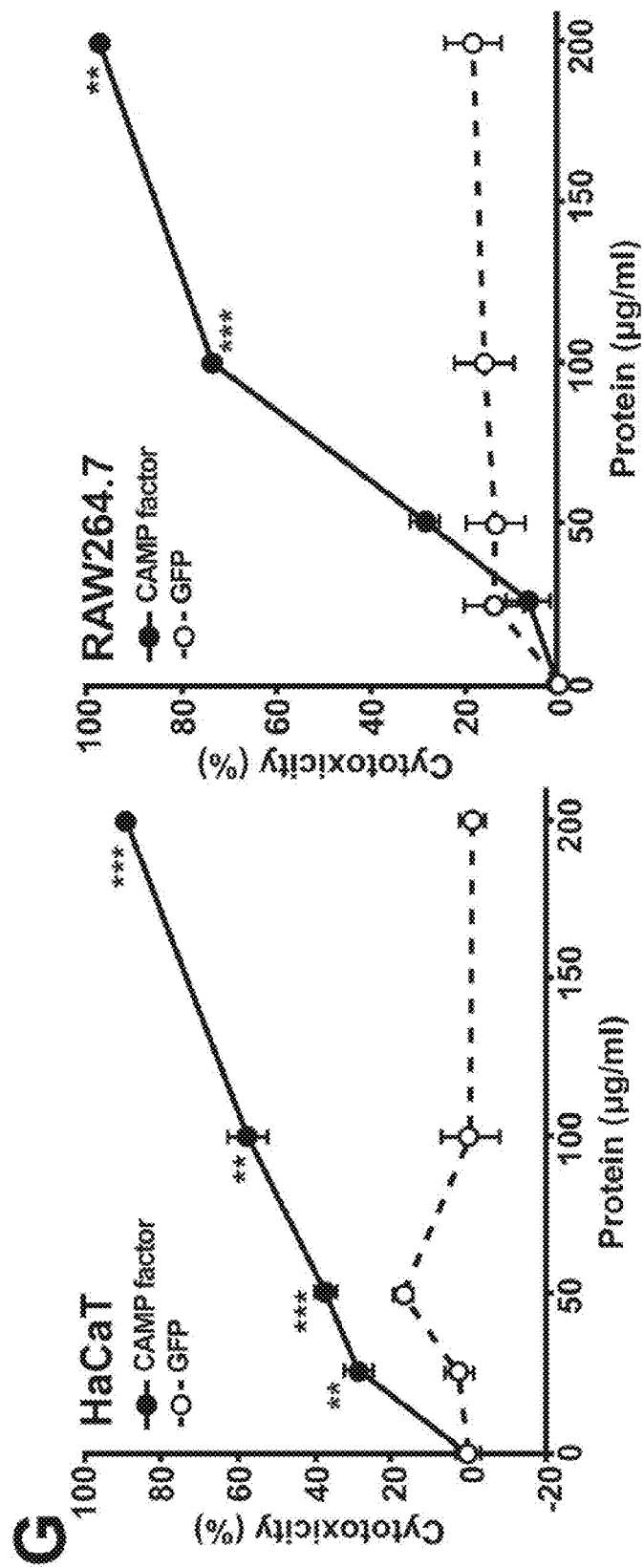
Figure 11:
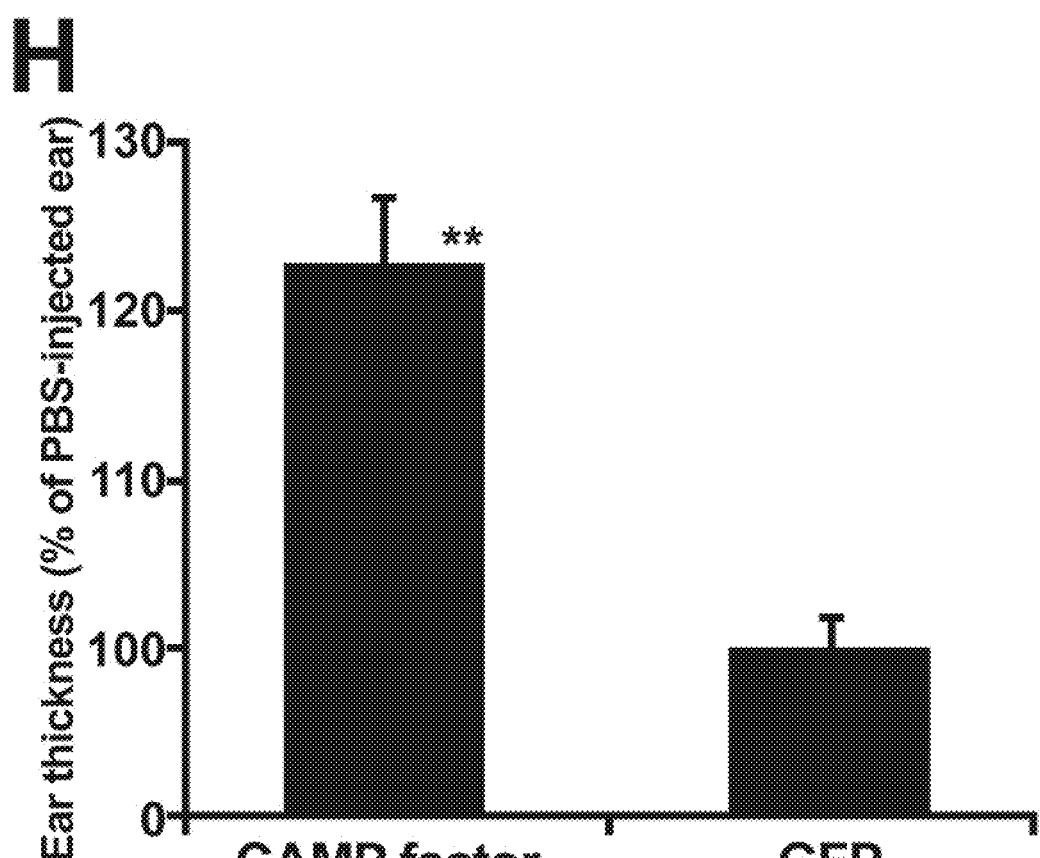

The CAMP factor was up-regulated in *P. acnes* under anaerobic or aerobic conditions. Thus, whether CAMP factor exerts a toxic effect on skin cells was examined. Keratinocytes have been known to be one of the primary targets of *P. acnes* during acne lesions. Therefore, whether CAMP factor exerts a detrimental effect on keratinocytes in the ears of ICR mice was tested. Purified recombinant CAMP factor was obtained by using the same protocol used to clone and purify sialidase. The PCR products of CAMP factor were inserted into a pEcoli-Nterm 6xHN plasmid and expressed in *E. coli* [*E. coli* BL21 (DE3 CAMP factor)]. After IPTG induction, the expression of CAMP factor-6xNH fusion protein was detected in a Coomassie blue stained SDS-PAGE gel at approximately 36 kDa molecular weight (FIG. 11, lanes 1 and 2). The CAMP factor-6xNH fusion protein was purified using a TALON resin column and confirmed by NanoLC-MS/MS sequencing. Sixteen internal peptides derived from CAMP factor were fully sequenced by NanoLC-MS/MS analysis via an HCTultra PTM system ion trap mass spectrometer. The MS/MS spectra of sequenced peptides matched well with those of CAMP factor (accession # gi|50842175) of *P. acnes*. An internal peptide (AVLLTANPASTAK (SEQ ID NO:3); 147-159 amino acid of SEQ ID NO:11) of CAMP factor was presented (FIG. 11B). Purified CAMP factor and GFP (1 µg/µl) were subcutaneously injected into the ears of ICR mice. After one-day injection, apoptotic cells were examined by terminal deoxynucleotidyltransferase dUTP nick end labeling (TUNEL) assay. Injection of recombinant CAMP factor did not induce detectable ear thickness. No apoptotic cells were detected from mice injected with GFP. Apoptotic cells are only detectable in the CAMP factor-injected mice, suggesting that CAMP factor is a toxic protein. During TUNEL assay, tissue sections of CAMP factor-injected ears were double-stained with a differentiated keratinocyte marker K10. The localization of apoptotic cells in keratinocytes suggested that CAMP factor is harmful to skin keratinocytes. To test the immunogenicity of CAMP factor, mice were immunized with a UV-irradiated *E. coli* vector-based vaccine [*E. coli* BL21 (DE3) T7/lacO CAMP factor]. A dose of UV (4,500 J/m$^2$) was given to irradiate all *E. coli*, both expressing (a CAMP factor-vector) and not expressing CAMP factor genes (a LacZ-empty vector). ICR mice were intranasally immunized with UV-irradiated *E. coli* BL21 (DE3) T7/lacO CAMP factor. The anti-CAMP factor antibody (IgG) in mouse sera was detectable 3 weeks after immunization. The result suggested that anti-CAMP factor antibody can be produced without boosting if mice were immunized with an irradiated *E. coli*-vector-based vaccine [*E. coli* BL21 (DE3 CAMP factor)]. No CAMP factor-reacted antibody production was found in the LacZ-empty vector-immunized mice. The anti-CAMP factor antibody can be also produced when mice were immunized with recombinant proteins/(in)complete adjuvants. ICR mice were immunized with CAMP factor-6×NH fusion protein or GFP using Freund/(in)complete adjuvants following the protocols as described above. The anti-CAMP factor antibody was detectable in the CAMP factor-, but not GFP-immunized mice. These results indicated that CAMP factor is immunogenic when mice were immunized with *E. coli*-vector based vaccines or recombinant proteins/(in)complete adjuvants. However, it is worthwhile to note that mice cannot produce anti-CAMP factor antibody if they were immunized with whole organism *P. acnes*.

Protective immunity in heat-killed *P. acnes*-immunized mice. The heat-killed *P. acnes* was used as an inactivated anti-*P. acnes* vaccines. After inactivating *P. acnes* at 65° C. for 30 min, inactivated *P. acnes* was spread on LB agar plates. The inability to form colonies indicated that the inactivation of *P. acnes* was completed. For immunization, heat-killed *P. acnes* ($10^8$ CFU; 50 µl) was intranasally inoculated into ICR mice for three times (first inoculation, a first boost at third week, and a second boost at the sixth week). Mice inoculated with 50 µl PBS serve as controls. The antibody production was detected by western blot ten weeks after immunization. For detection of protective immunity, ears of ICR mice immunized with heat-killed *P. acnes* were subcutaneously challenged with live *P. acnes* ($10^7$ CFU). Ear thickness was measured for three days. The challenge of *P. acnes* to PBS-inoculated mice induced a 1.8-fold increase in ear thickness. Importantly, the increase of *P. acnes*-induced ear thickness was decreased by 40% in the killed-*P. acnes*-immunized mice. Similarly, the *P. acnes*-induced ear redness was significantly suppressed in killed-*P. acnes*-immunized mice, suggesting that mice immunized with killed-*P. acnes* produced a protective immunity to *P. acnes* infection. The change in the level of pro-inflammatory cytokines was determined after immunization. A tissue chamber was subcutaneously implanted into abdominal skin of ICR mice for 7 days, and then *P. acnes* ($10^7$ CFU) was injected into the implanted tissue chamber. The level of MIP-2 cytokine in tissue chamber fluid was measured by ELISA three days after *P. acnes* injection. In the PBS-inoculated mice, a significant increase in MIP-2 level was observed 3 days after *P. acnes* injection. The increase of MIP-2 cytokine was reduced by more than 50% when mice were immunized with killed-*P. acnes*.

The methods next examined if the antibodies against sialidase and CAMP factor can be produced in killed *P. acnes*-immunized mice. 50 µg of purified recombinant sialidase, CAMP factor as well as lysates of *P. acnes* were subjected to a 12.5% SDS-PAGE gel and transferred to a PDVF membrane. The membrane was incubated overnight with mouse serum obtained from killed *P. acnes*-immunized mice. Many proteins with molecular weights greater than 50 kDa reacted positively to serum obtained from the killed *P. acnes*-immunized mice. However, neither sialidase nor CAMP factor reacted to the serum, indicating that neither sialidase nor CAMP factor is not immunogenic if mice were immunized with whole organism *P. acnes*.

Overall, the data indicated that sialidase and CAMP factor are immunogenic when mice were immunized with *E. coli*-vector-based vaccines or recombinant proteins/(in)complete Freund adjuvants. Mice immunized with killed *P. acnes* produced antibodies against several proteins (>50 kDa), but not sialidase and CAMP factor. Mice immunized with a sialidase-based vaccine or killed *P. acnes* produced a significant protection against live *P. acne* challenge.

Bacteria Culture.

*P. acnes* (ATCC 6919) was cultured on *Brucella* broth agar, supplemented with 5% (v/v) defibrinated sheep blood, vitamin K, and hemin under anaerobic conditions using Gas-Pak (BD Biosciences, San Jose, Calif.) or aerobic conditions at 37° C. Bacteria isolated from a single colony were inoculated in Reinforced *Clostridium* Medium (RCM) (Oxford, Hampshire, England) and cultured at 37° C. until logarithmic growth phase (OD600=0.7–2.0). *S. aureus* 113 (ATCC 35556) was cultured on Tryptic soy broth (TSB) agar plates. Bacteria isolated from a single colony were inoculated in TSB at 37° C. overnight. Bacterial pellets were harvested by centrifugation at 5,000 g for 10 min.

Molecular Cloning and Expression of Recombinant Camp Factor.

A polymerase chain reaction (PCR) product encoding a putative protein (29-267 amino acid residues) of CAMP factor (accession number: gi/50842175) was generated using gene-specific primers designed based on the complete genome sequence of *P. acnes*. The forward PCR primer (5'-TAAGGCCTCTGTCGACGTCGAGCCGAC-GACGACCATCTCG-3'; SEQ ID NO:4) included 16 nucleotides containing a SalI site to match the end of the In-Fusion Ready pEcoli-Nterm 6×HN vector (Clontech Laboratories, Inc., Mountain View, Calif.), and 26 nucleotides encoding the N-terminal of CAMP factor. The reverse PCR primer (5'-CAGAATTCGCAAGCTTGGCAGCCTTCT-TGACATCGGGGGAG-3'; SEQ ID NO:5) consisted of 16 nucleotides containing a HindIII site to match the end of the vector and 23 nucleotides encoding the C-terminal of the protein. PCR was performed by using *P. acnes* genomic DNA as a template. The amplified DNA products were inserted at the restriction enzyme sites into an In-Fusion Ready pEcoli-Nterm expression plasmid and transformed into competent cells [*Escherichia coli* (*E. coli*), BL21 (DE3), Invitrogen, Carlsbad, Calif.], which were subsequently selected on Luria-Bertani (LB) plates containing ampicillin (50 µg/ml) and cultured overnight at 37° C. For green fluorescence protein (GFP) expression as a control, pEcoli-Nterm-GFP vector (Clontech Laboratories) supplied with the kit as a positive control was used for transformation. An aliquot of the overnight culture was diluted 1:20 with LB medium and incubated at 37° C. until reaching $OD_{600}$=0.7. Isopropyl-β-D-thiogalactoside (IPTG) (1 mM) was added into the culture and incubated for 4 hr to induce protein synthesis. Bacteria were harvested by centrifugation and disrupted by sonication on ice for 5 min and lysed by centrifuging at 3,000 g for 30 min. The pellet was washed with PBS and dissolved in 50 mM sodium phosphate buffer containing 6 M guanidine HCl and 300 mM NaCl. The expressed protein possessing 6×HN tag was purified in denaturing condition with a TALON Express Purification Kit (Clontech Laboratories). The purified protein was dialyzed against $H_2O$, lyophilized, dissolved in ethylene glycol (1 mg/1.2 ml), and then refolded in 10 ml of 250 mM Tris-HCl buffer, pH 8.4, containing 5 mM cysteine, 0.5 mM cystine, and 1.5 M urea at 4° C. overnight. The refolded protein was dialyzed against PBS and concentrated. A 10% SDS-polyacrylamide gel electrophoresis (PAGE) and coomassie blue staining were utilized to detect the protein expression.

Protein Identification via NanoLC— LTQ MS/MS Analysis.

In-gel digestion with trypsin and protein identification via a NanoLC-LTQ mass spectrometry (MS) analysis were performed. The automated NanoLC-LTQ MS/MS setup consisted of an Eksigent Nano 2D LC system, a switch valve, a C18 trap column (Agilent, Santa Clara, Calif.), and a capillary reversed phased column (10 cm in length, 75 µm i.d.) packed with 5 µm, C18 AQUASIL resin with an integral spray tip (Picofrit, 15 µm tip, New Objective, Woburn, Mass.). A reversed-phase LC directly coupled to a LTQ ion trap mass spectrometer (Thermo Electron, Waltham, Mass.) was run using a linear gradient elution from buffer A (H2O plus 0.1% formic acid) to 50% buffer A plus 50% buffer B (acetonitrile plus 0.1% formic acid) in 100 min. The instruments were operated in the data dependent mode. Data on the four strongest ions above an intensity of $2 \times 10^5$ were collected with dynamic exclusion enabled and the collision energy set at 35%. Large-scale MS/MS spectra were extracted using default value by Bioworks® 3.2 (Thermo Scientific, San Jose, Calif.). Charge state deconvolution and deisotoping were not performed. All MS/MS spectra were analyzed using in-house Sorcerer™ 2 system with SEQUEST (v.27, rev. 11) as the search program for protein identification. SEQUEST was set up to search the target-decoy ipi.MOUSE.v3.14 database containing protein sequences in both forward and reverse orientations (68627 entries in each orientation) using trypsin as the digestion enzyme with the allowance of up to five missed cleavages. The false positive rates were roughly determined by doubling the ratio between the number of decoy hits and the total number of hits. SEQUEST was searched with a fragment ion mass tolerance of 0.5 Da and a parent ion tolerance of 1.0 Da.

Co-Hemolytic Activity of CAMP Factor.

Co-hemolytic reaction of recombinant CAMP factor was detected on a sheep blood agar. *S. aureus* 113 (ATCC 35556) (10 µl, $2 \times 10^7$ CFU/ml in PBS), used as a source of SMase, was streaked on an agar plate. Ten µl of recombinant CAMP factor (250 µg/ml) or GFP as a control protein (250 µg/ml) was spotted beside the *S. aureus* streak grown at 37° C. for 18 hr under an aerobic condition.

Vaccination and Titration of Antibodies to CAMP Factor.

Female 8-week-old ICR mice were used in all experiments. ICR mice were housed according to institutional guidelines. The mice were intranasally vaccinated with *E. coli* [BL21 (DE3)] over-expressing CAMP factor or GFP that were inactivated by UV (3500 J/m$^2$) irradiation. Irradiated *E. coli* was unable to grow on a LB agar plate (data not shown). Twenty five µl of *E. coli* suspension ($1 \times 10^9$ CFU) was inoculated into the nasal cavity. Sera were individually collected for detection and titration of antibody to CAMP factor 2 and 3 weeks after vaccination.

To determine antibody titers to CAMP factor by enzyme-linked immunosorbent assay (ELISA), purified CAMP factor (5 ug/ml) was diluted with a coating buffer (0.015 M $Na_2CO_2$, 0.35 M $NaHCO_2$ and 0.05% $NaN_2$), and coated onto a 96-well ELISA plate (Corning, Lowell, Mass.) at 4° C. overnight. The plates were washed with PBS containing 0.1% (w/v) Tween-20, and blocked with PBS containing 1% (w/v) bovine-serum albumin (BSA) and 0.1% (w/v) Tween-20 for 2 hr at room temperature. Antisera (1:10,000 dilution) obtained from mice vaccinated with *E. coli* over-expressing CAMP factor or GFP were added to the wells and incubated for 2 hr. Goat anti-mouse IgG (H+L) IgG-horseradish peroxidase (HRP) conjugate (Promega, Madison, Wis.) (1:5,000 dilution) was added, incubated for 2 hr, and then washed. HRP activity was determined with a OptEIA™ Reagent Set (BD Biosciences, San Diego, Calif.). The optical density (OD) of each well was measured at 450 nm.

Cell Culture, Determination of Cytotoxicity and Neutralization Assay.

A human keratinocyte cell line, HaCaT, or a murine macrophage cell line, RAW264.7, was cultured in Dulbecco's Modified Eagle's Medium (DMEM) or Roswell Park Memorial Institute (RPMI) 1640 medium, respectively, supplemented with 10% heat-inactivated fetal bovine serum (FBS) at 37° C. with 5% (v/v) $CO_2$. For determination of cytotoxicity of CAMP factor, cells ($1 \times 10^5$/well) were incubated in a 96-well micro titer plate with recombinant CAMP factor or GFP in a 1% FBS-medium for 18 hr. After incubation, cell viability was determined with an acid phosphatase (ACP) assay. Cells were washed with PBS three times and incubated with 100 µl of 10 mM p-nitrophenyl phosphate (pNPP) in an ACP assay buffer [1 M sodium acetate buffer, pH5.5, containing 0.1% (w/v) triton-X] for 1 hr at 37° C. Ten µl of 1N NaOH was then added to stop the reaction and OD at 405 nm was measured. Cytotoxicity was calculated as the percentage of cell death caused by triton-X (0.1%, v/v).

To detect secretion and/or release of CAMP factor and acid SMase (ASMase), HaCaT or RAW264.7 cells ($5 \times 10^5$) were co-cultured with [$5 \times 10^6$ CFU/well; multiplicity of infection (MOI)=1:10] or without *P. acnes* in a serum-free medium in a 24-well plate at 37° C. for 14 hr. The supernatant was centrifuged and filtrated with a 0.22 um pore-size filter to remove cell debris and bacteria, and then concentrated 10 folds using a 10 kDa cut-off ultrafiltration membrane (Amicon Inc., Beverly, Mass.). The concentrated supernatant (10 µg) was subjected to a 10% SDS-PAGE for Western blot analysis using mouse anti-CAMP factor antiserum and goat anti-ASMase IgG (Santa Cruz Biotechnology, Inc., Santa Cruz, Calif.).

For neutralization assay, cells ($1 \times 10^5$/well) were co-cultured with *P. acnes* ($1 \times 10^6$ CFU/well; MOI=1:10) in the presence of anti-CAMP factor or anti-GFP antiserum (2.50, v/v), in which complements had been deactivated by heating at 56° C. for 30 min, for 14 hr. To examine involvement of host ASMase in *P. acnes* pathogenicity, cells were co-cultured with *P. acnes* in the presence or absence of a cell-permeable selective ASMase inhibitor, desipramine (10 µM) (Sigma, St. Louis, Mo.) for 14 hr. After incubation, cell viability was determined and cytotoxicity was calculated as described above.

Intradermal injection of mouse ear with recombinant CAMP factor. To examine involvement of CAMP factor to *P. acnes*-inflammation in vivo, the ear of Imprinting Control Region (ICR) mice (Harlan, Indianapolis, Ind.) was intradermally injected with recombinant CAMP factor (10 µg/20 µl) or GFP (10 µg/20 µl) in PBS. The contralateral ear received an equal amount of PBS (20 µl). The ear thickness was measured using a micro caliper (Mitutoyo, Kanagawa, Japan) 24 hr after injection and a CAMP factor-induced increase in ear thickness reported as % of ear thickness in PBS-injected ears.

Detection of ASMase in ICR mouse ear. Ears of ICR mice were intradermally injected with of live *P. acnes* ($1 \times 10^7$ CFU/20 µl) in PBS. The contralateral ear received an equal amount of PBS (20 µl). Twenty four hr after bacterial challenge, the ear was excised, punched with an 8 mm biopsy and homogenized in 200 µl of PBS with a tissue grinder. The supernatant (1 ug of total protein) was subjected to Western blotting using goat anti-ASMase IgG (0.2 µg/ml) (Santa Cruz Biotechnology, Inc.) followed by monoclonal anti-glyceraldehyde 3-phosphate dehydrogenase (GAPDH) IgG (2 µg/ml) (Fitzerald Inc., Concord, Mass.). Normal goat or mouse IgG was used as a negative control for the detection.

Transmission Electron Microscopy and Fluorescence Immunohistochemistry.

ICR mouse ears were intradermally injected with live *P. acnes* or PBS as described above. Twenty four hr after bacterial challenge, the ear was excised and fixed in Karnovsky's fixative (4% paraformaldehyde, 2.5% glutaraldehyde, 5 mM $CaCl_2$ in 0.1M Na Cacodylate buffer, pH 7.4) overnight at 4°

C. followed by 1% OsO$_4$ in 0.1M Na Cacodylate buffer, pH 7.4, en bloc staining with 4% uranyl acetate in 50% ethanol, and subsequently dehydrated using a graded series of ethanol solutions followed by propylene oxide and infiltration with epoxy resin (Scipoxy 812, Energy Beam Sciences, Agawam, Mass.). After polymerization at 65° C. overnight, thin sections were cut and stained with uranyl acetate (4% uranyl acetate in 50% ethanol) followed by bismuth subnitrate. Sections were examined at an accelerating voltage of 60 kV using a Zeiss EM10C electron microscope (Oberkochen, Germany).

ICR mouse ears were intradermally injected with live *P. acnes* or PBS as described above. Twenty four hr after bacterial challenge, the ear was excised, fixed in an optimum cutting temperature (OCT) compound (Sakura Finetek, Torrance, Calif.) and frozen at −80° C. Sections (7 μm) were fixed in 10% formamide in PBS. After blocking with PBS containing 5% BSA and anti-mouse cluster of differentiation (CD) 16/CD32 IgG (5 ug/ml) (BD Biosciences Pharmingen, Sparks, Md.) for 30 min, sections were then incubated with biotinylated anti-mouse CD11b IgG (5 μg/ml) (BD Biosciences Pharmingen), a macrophage marker, followed by goat anti-ASMase IgG (5 μg/ml). Tetramethylrhodamine isothiocyanate (TRITC)-streptavidin conjugate (5 ug/ml) (ZYMED, Carlsbad, Calif.) and fluorescein isothiocyanate (FITC)-labeled anti-goat IgG (5 μg/ml) (Santa Cruz Biotechnology, Inc.) were applied to the sections, incubated for 30 min at room temperature, and followed by 4'-6-Diamidino-2-phenylindole (DAPI) staining (Sigma). Images were obtained using an Olympus BX41 fluorescent microscope (Olympus, Center Valley, Pa.).

Effect of Desipramine on *P. Acnes*-Induced Inflammation In Vivo.

To examine involvement of host ASMase in *P. acnes* pathogenicity, the ICR mice were intraperitoneally injected with a selective inhibitor of ASMase (20 mg/kg mouse) in PBS or an equal amount of PBS as a control. The ears of ICR mice were intradermally injected with live *P. acnes* or PBS as described above 30 min after desipramine treatment. Ear thickness was measured 24 hr after injection and a *P. acnes*-induced increase in mouse ear reported as % of ear thickness in PBS-injected ears.

Combination Effect of CAMP Factor Vaccine and Local Injection with Anti-ASMase IgG on *P. acnes*-Induced Inflammation.

ICR mice were vaccinated with inactivated *E. coli* over-expressing CAMP factor or GFP as described above in 3-week interval. Two weeks after the second boost, live *P. acnes* was intradermally injected into the ear of vaccinated mice in the same manner as described above. Within 30 min, the left ear (received *P. acnes*) was injected with goat anti-ASMase IgG (4 μg/20 μl) or normal goat IgG (control) in PBS, and the right ear (received PBS) was injected with an equal volume of PBS. Ear thickness was measured 24 hr after injection and a *P. acnes*-induced increase in mouse ear reported as % of ear thickness in PBS-injected ears.

CAMP Factor Expression, Mass Spectrometric Identity, and Biological Activity.

To assess the expression of CAMP factor, *E. coli* transformed with an expression plasmid containing an insert encoding CAMP factor were incubated with or without IPTG. A prominent band of the expected size (the deduced molecular mass of CAMP factor-6×NH fusion protein is 32.4 kDa) was detected in the insoluble fraction from IPTG-induced cells. The CAMP factor was purified using a TALON resin column. CAMP factor expression was confirmed by NanoLC-LTQ MS/MS mass spectrometric sequencing after in-gel trypsin digestion. Nine internal peptides derived from CAMP factor were fully sequenced by NanoLC-LTQ MS/MS mass spectrometry, matching well with those from *P. acnes* CAMP factor (accession number: gi/50842175). An internal peptide (AVLLTANPASTAK (SEQ ID NO:3); 147-158 amino acid residues) of CAMP factor was identified, validating the expression of recombinant CAMP factor.

A conventional CAMP test was utilized to examine biological activity of the recombinant CAMP factor, which demonstrated a co-hemolytic CAMP reaction when spotted adjacent to SMase-expressing *S. aureus* on a sheep blood agar plate. The data indicates that the recombinant CAMP factor is biologically active.

Immunogenicity of recombinant CAMP factor. To examine a potential of CAMP factor as a target of vaccine, ICR mice were immunized with CAMP factor, or a GFP control protein, using an *E. coli*-based delivery system. IgG against CAMP factor was detected 14 days after immunization by Western blot. No immunoreactivity against CAMP factor was detectable in GFP-immunized mice. ELISA analysis showed a significant increase in antibody titer 14 days after immunization, increasing at 21 days after immunization. Anti-CAMP factor IgG titers in the antiserum from CAMP factor-immunized mice was >100,000 21 days after immunization, respectively, while the titer from GFP-immunized mice was <100 (antiserum dilution curves not shown). These data indicate that CAMP factor is highly immunogenic.

Identification of CAMP Factor in the Supernatant of *P. acnes* Cultures.

To identify secreted CAMP factor, the supernatant of *P. acnes* cultures from logarithmic growth phase was concentrated and subjected to Western blotting with a mouse anti-CAMP factor antiserum. A single band was detected in the *P. acnes* culture supernatant (FIG. 11F, left panel, lane 2) at the position corresponding to recombinant CAMP factor that had been treated with enterokinase to remove 6×NH tag (FIG. 11F, left panel, lane 1), but was not detected in concentrated RCM used for *P. acnes* culture (FIG. 11F, left panel, lane 3). No bands were detected with anti-GFP control antiserum (FIG. 11F, right panel). These data suggest that CAMP factor is a secreted protein.

Involvement of CAMP factor in Pathogenicity of *P. acnes*.

To explore the CAMP factor cytotoxicity in vitro, the human keratinocyte cell line, HaCaT, or the murine macrophage cell line, RAW264.7, was treated with recombinant CAMP factor or GFP control protein. Treatment with CAMP factor resulted in dose-dependent cytotoxicity in both HaCaT and RAW264.7 cells (FIG. 11G). To examine involvement of CAMP factor in *P. acnes*-induced inflammation, mouse ear was intradermally injected with recombinant CAMP factor or GFP. A significant increase in ear thickness was observed in CAMP factor-injected ear 24 hr after the injection, but no increase induced by GFP injection (FIG. 11H). These data suggest the involvement of CAMP factor in *P. acnes*-induced inflammatory reaction.

The Involvement of Bacterial CAMP Factor and Host ASMase in *P. Acnes* Pathogenicity In Vitro.

Figure 12:
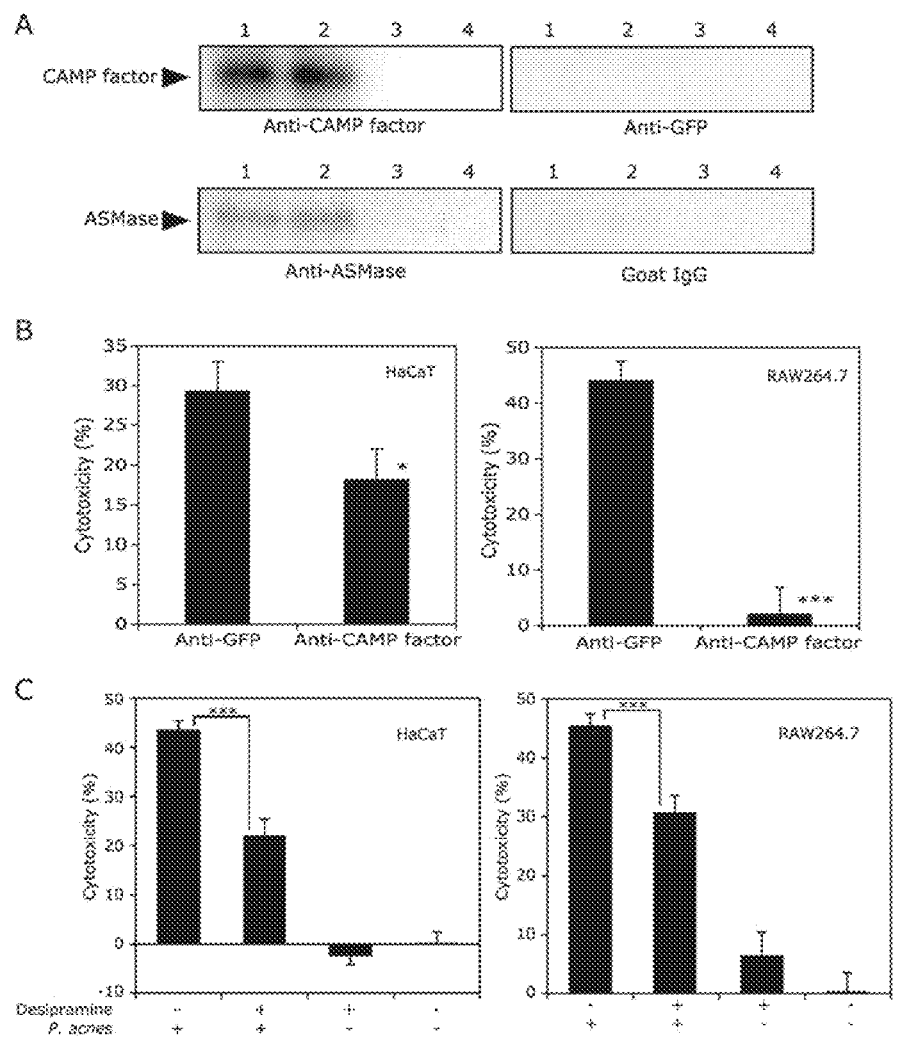
FIG. 12A-C shows the involvements of bacterial CAMP factor and host ASMase in *P. acnes* pathogenicity in vitro. (A) CAMP factor and ASMase were detected in the supernatant of cell culture by Western blot following co-cultured with *P. acnes*. The HaCaT (lanes 1 and 3) or RAW264.7 (lanes 2 and 4) ($5 \times 10^5$/well) were co-cultured with *P. acnes* ($5 \times 10^6$ CFU/well; MOI=1:10) (lanes 1 and 2) or without *P. acnes* (lanes 3 and 4) in serum-free medium at 37° C. for 14 hr. The concentrates of cell culture supernatant (10 μg total protein) were subjected to Western blotting. CAMP factor and ASMase were detected with mouse anti-CAMP factor antiserum and goat anti-ASMase IgG, respectively. (B) *P. acnes*-mediated cell death was neutralized by anti-CAMP factor antiserum in vitro. HaCaT or RAW264.7 cells ($1 \times 10^5$/well) were co-cultured with *P. acnes* ($1 \times 10^6$ CFU/well; MOI=1:10) for 14 hr in the presence of mouse anti-CAMP factor or anti-GFP antiserum (2.5% v/v). (C) Including ASMase inhibitor decreased *P. acnes*-mediated cell death in vitro. HaCaT or RAW264.7 cells ($1 \times 10^5$/well) were cultured without or with *P. acnes* ($1 \times 10^6$ CFU/well, MOI=1:10) in medium containing desipramine (10 μM), a selective ASMase inhibitor, or the equal amount of PBS (vehicle) at 37° C. for 14 hr. After incubation, the cell viability was determined and the cytotoxicity was calculated as described in Materials and Methods. The data represent as mean±SE (n=10, $p<0.05$* and $p<0.0005$*** by Student's t-test).

To examine whether ASMase is released from host cells when co-cultured with *P. acnes*, HaCaT or RAW264.7 cells were cultured with and without *P. acnes* for 14 hr. After incubation, the cell culture supernatant was subjected to Western blotting, probing with a mouse anti-CAMP factor antiserum and goat anti-ASMase IgG. CAMP factor and ASMase were detected in the cell culture supernatant only when the cells were co-cultured with *P. acnes* (FIG. 12A, lanes 1 and 2). The homology between human and mouse ASMases (mature protein) is greater than 90% and their molecular weights are almost identical. Neither of these ASMases were detected in the cell cultures without *P. acnes* (FIG. 12A, lanes 3 and 4), and ASMase was not detected in the supernatant of *P. acnes* culture. These data suggest that ASMase is released and/or secreted from the host cells co-cultured with *P. acnes*.

To examine the effect of neutralization of CAMP factor on *P. acnes*-induced cytotoxicity, HaCaT and RAW264.7 cells were co-cultured with *P. acnes* in the presence of anti-CAMP factor or anti-GFP antiserum (FIG. 12B). *P. acnes* induced 29.3% and 44.0% cell death on HaCaT cells, respectively, in the presence of anti-GFP control antiserum. The addition of anti-CAMP factor antiserum reduced *P. acnes*-induced cell death by 18.2% and 2.1%, respectively. To examine the involvement of host ASMase in the pathogenicity of *P. acnes*, cells were co-cultured with *P. acnes* in the presence of desipramine, a selective ASMase inhibitor, or an equal amount of PBS (vehicle) (FIG. 12C). *P. acnes* induced 43.4% and 45.4% cell death on HaCaT and RAW264.7 cells, respectively. The addition of desipramine significantly reduced *P. acnes*-induced cell death on the both cells by 21.9% and 30.6%, respectively. These data suggest the involvements of CAMP factor and ASMase in *P. acnes*-induced cytotoxicity.

Possible Involvement of Host ASMase in *P. acnes* Pathogenicity In Vivo.

Figure 13:
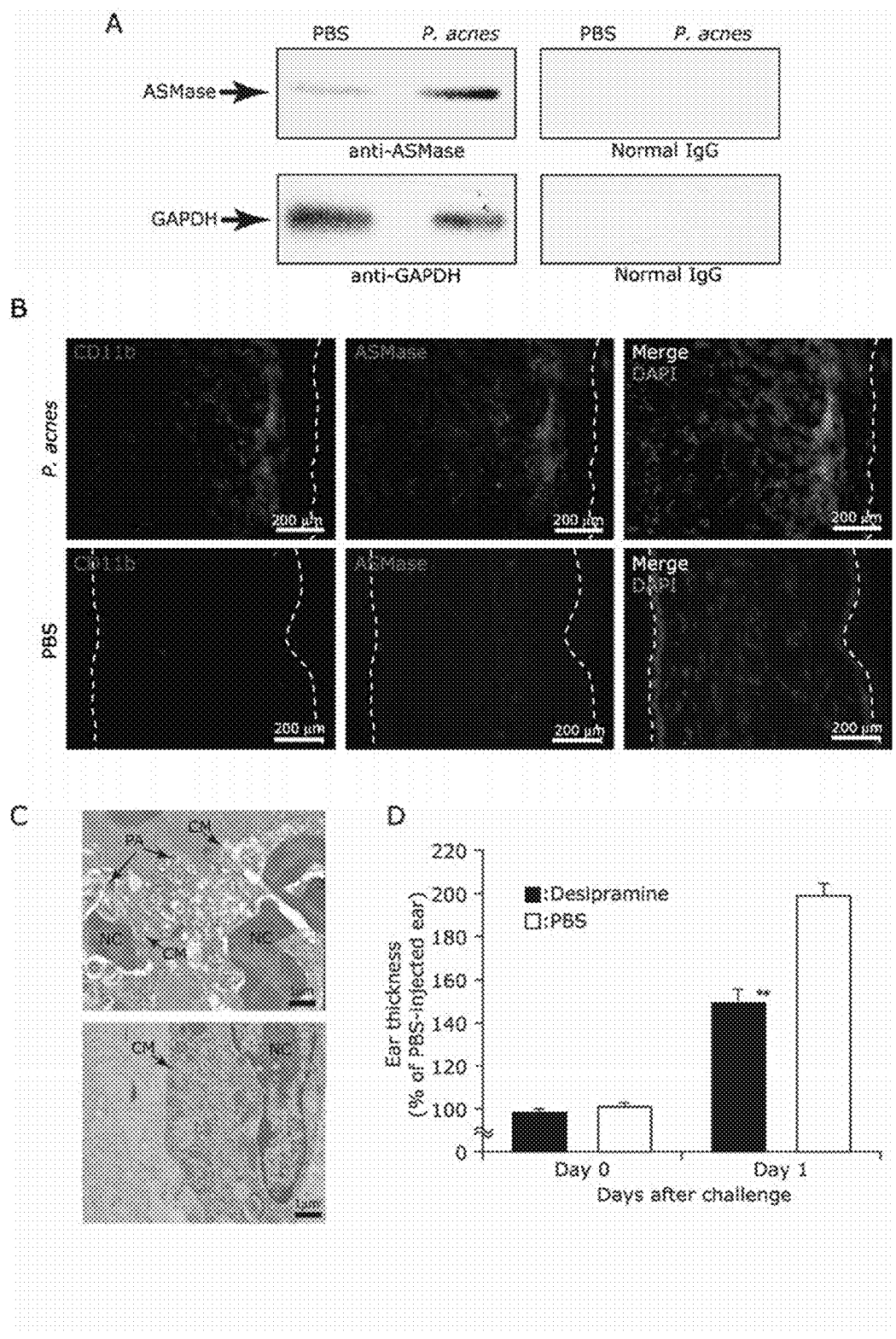
FIG. 13A-D shows the possible involvement of host ASMase in pathogenicity of *P. acnes* in vivo. (A) Amount of soluble ASMase in mouse ear increased 24 hr after bacteria challenge. Ears of ICR mice were intradermally injected with of *P. acnes* in PBS ($1 \times 10^7$ CFU/20 μl; left ear) or PBS (20 μl; right ear), and excised after 24 hr. Ear tissue was obtained with a 8 mm biopsy and homogenized in PBS. The supernatant (1 ug of total protein) was subjected to Western blotting. ASMase (upper panels) and GAPDH (lower panels) were detected with goat anti-ASMase IgG followed by anti-GAPDH IgG (left panels). Normal goat or mouse IgG was used as a negative control for the detection (right panels). (B) *P. acnes* challenge into mouse ear attracted CD11b+ macrophages which highly expressed ASMase. Frozen sections of mouse ear obtained 24 after bacteria challenge were stained with biotinylated anti-mouse CD11b IgG, a conventional macrophage marker, and TRITC-streptavidin conjugate, followed by Goat anti-ASMase IgG and anti-goat IgG-TRITC conjugate. The nuclei were stained with DAPI (blue). Bar=200 μm. (C) Transmission electron microscopy (10,000× magnification) was used to visualize colonized *P. acnes* and ruptured cell membrane in mouse ears injected with *P. acnes* or PBS. PA, *P. acnes*; CM, cell membrane; NC, nucleus. Bar=1 μm. (D) Systemic pre-treatment of ICR mice with selective ASMase inhibitor relieved *P. acnes*-induced inflammation. ICR mice were intraperitoneally injected with desipramine (20 mg/kg mouse) or an equal amount of PBS (vehicle) 30 min prior to the bacterial challenge. After pre-treatment, live *P. acnes* ($1 \times 10^7$ CFU/20 μl) in PBS or an equal amount of PBS (control) was intradermally injected into left ear or right ear, respectively. The ear thickness was measured using a micro caliper before and 24 hr after the bacterial challenge and changes reported as % of ear thickness in PBS-injected ears. The data represent as mean±SE (n=3, $p<0.005$** by Student's t-test).

To examine involvement of host ASMase in *P. acnes* pathogenicity in vivo, the ears of ICR mice were injected intradermally with *P. acnes* or PBS, excised 24 hr after bacterial challenge, and used for the following experiments. First, the mouse ears were homogenized and the homogenate supernatant was subjected to Western blot using anti-ASMase IgG (FIG. 13A). A single band was detected at the expected molecular weight for ASMase (~60 kDa). *P. acnes* injection increased the amount of ASMase in the ear relative to PBS injection. To examine the localization of ASMase in the mouse ear, frozen sections were co-stained with anti-mouse CD11b IgG, a conventional macrophage marker, followed by goat anti-ASMase IgG (FIG. 13B). This double immunofluorescent staining revealed infiltration of macrophages into the site of *P. acnes* administration 24 hr after bacterial challenge; no CD11b+ macrophages were observed in PBS-injected control ears. ASMase was highly expressed in the infiltrating CD11b+ macrophages. Transmission electron microscopy showed colonizing and/or phagocytosed *P. acnes* in macrophage-like cells and in the extracellular space 24 hr after bacterial challenge (FIG. 13C); no bacteria was observed in PBS injected ears. In addition, ruptured cell membranes were observed in the *P. acnes*-injected ear, whereas the cell membranes of the PBS-injected ear appeared intact. These data suggest that intradermal *P. acnes* challenge induces the infiltration of macrophages, which highly express ASMase. In addition, *P. acnes*-induced ear swelling was significantly relieved when mice were systemically pretreated with desipramine 30 min before the bacterial challenge (FIG. 13D), suggesting the involvement of host ASMase in *P. acnes*-induced inflammation and the development of skin lesions.

Figure 14:
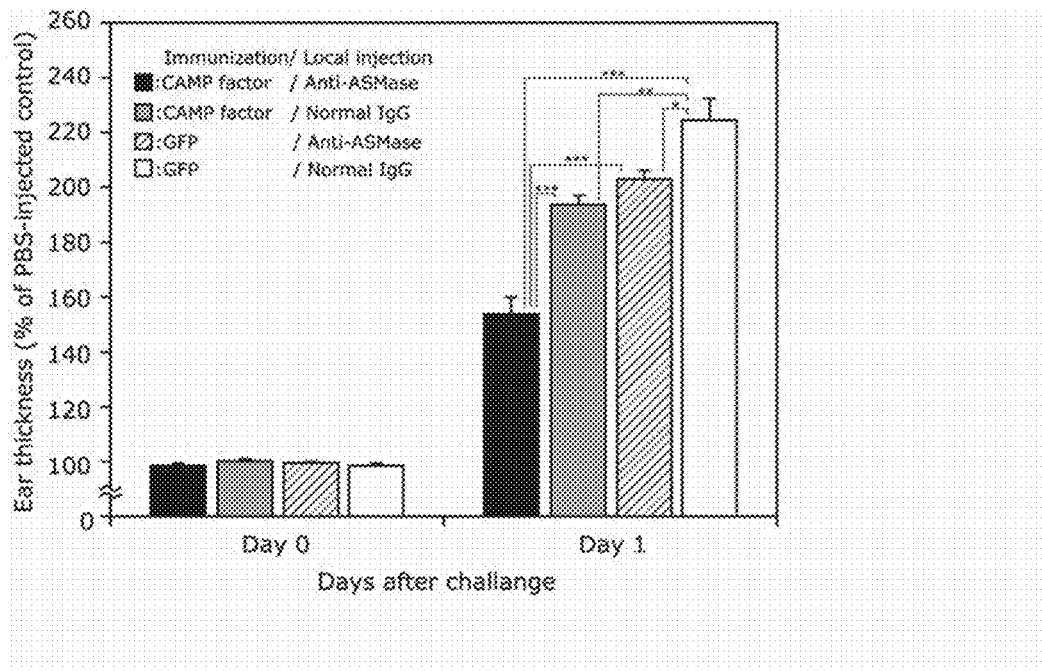
FIG. 14 shows a combination of CAMP factor vaccine and local injection with anti-ASMase IgG synergistically suppressed *P. acnes*-induced inflammation. ICR mice were vaccinated with UV-killed *E. coli* over-expressing CAMP factor or GFP in a 3-week interval. Two weeks after the second boost, *P. acnes* was intradermally injected into the ear of vaccinated mice in the same manner as described above. Within 30 min, the left ear (received *P. acnes*) was injected with goat anti-ASMase IgG (4 μg/20 μl) or normal goat IgG (control) in PBS, and the right ear was injected with an equal volume of PBS (n=8). Ear thickness was measured 24 hr after the bacteria challenge and changes reported as % of ear thickness in PBS-injected ears. The data represent as mean±SE ($p<0.05$*, $p<0.005$, $p<0.0005$* by Student's t-test).
Figure 15:
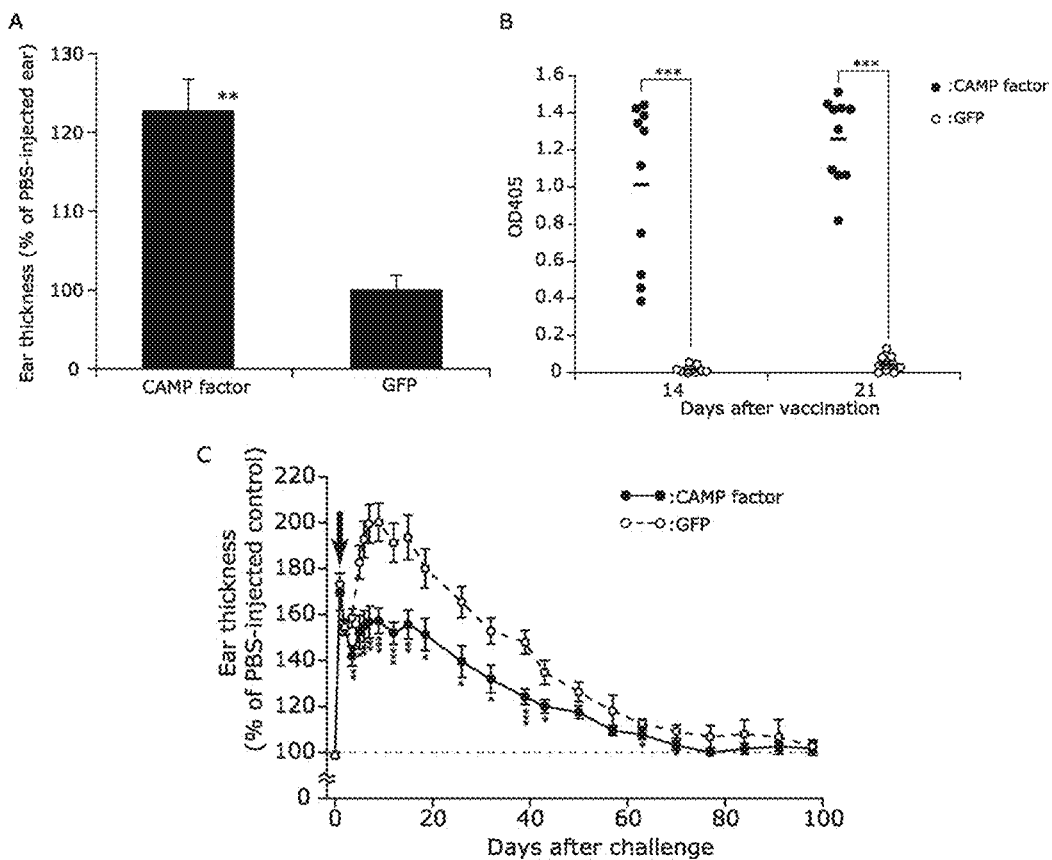
FIG. 15A-C shows the effects of CAMP factor-based vaccine on *P. acnes*-induced inflammation on mice. (A) Intradermal injection with CAMP factor induced inflammatory reaction in ICR mouse ear. The left ear was intradermally injected with recombinant CAMP factor (10 μg/20 μl) or GFP (10 μg/20 μl) in PBS. Right ear received an equal amount of PBS (20 μl). The ear thickness was measured using a micro caliper 24 hr after the injection and changes reported as % of ear thickness in PBS-injected ears. The data represented as mean±SE (n=4, $P<0.005$** by Student's t-test). (B) The titer of CAMP factor antibodies was determined by ELISA. The mice were bled 14, and 21 days after the vaccination with CAMP factor (n=10). The antisera (1:10,000 dilution) were reacted with CAMP factor immobilized on a microtiter ELISA plate. The captured antibodies were detected with goat-anti-mouse IgG (H+L)-HRP conjugate and OptEIA™ Reagent Set. The optical density of each well was measured at 450 nm. Bar represents average of 10 individual assays. (C) Sole immunization of ICR mice with CAMP factor provided therapeutic immunity against *P. acnes*-induced inflammation. Live *P. acnes* ($1 \times 10^7$ CFU/20 μl) in PBS or an equal amount of PBS (control) was intradermally injected into left ear or right ear, respectively, of naïve mice. After 24 hr, the mice were intranasally immunized with UV-killed *E. coli* over-expressing CAMP factor or GFP (arrow). Ear thickness was measured at the indicated times after bacterial challenge and changes reported as % of ear thickness in PBS-injected ears. Data represent mean±SE (n=10, $P<0.05$*, $P<0.005$, $P<0.0005$* by Student's t-test).
Figure 16:
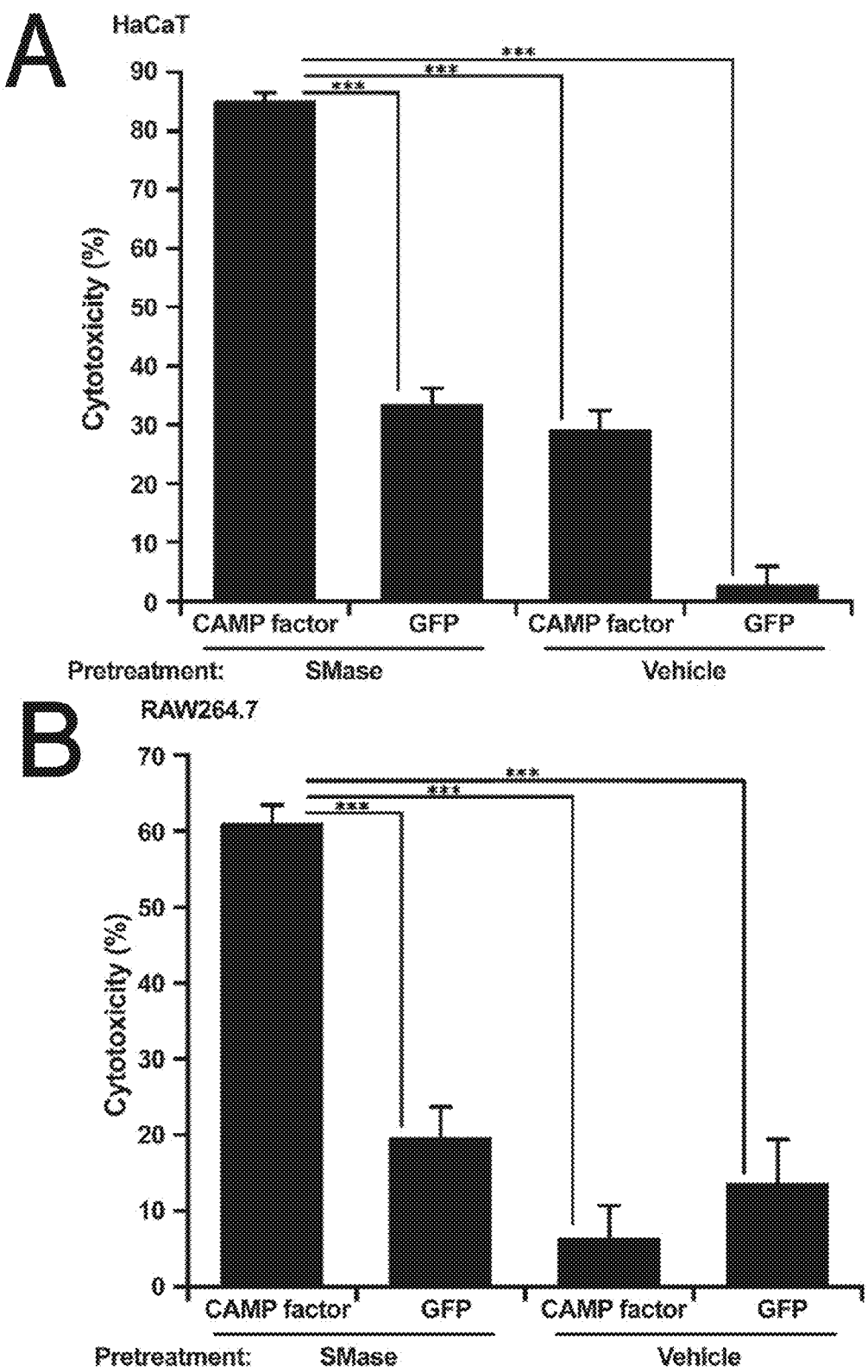
FIG. 16A-B shows co-cytotoxic properties of CAMP factor and bacterial SMase in vitro. The HaCaT (A) or RAW264.7 cells (B) were pretreated with SMase from *S. aureus* (350 mU/ml) or an equal amount of vehicle for 15 min, washed three times to remove the enzyme, and then incubated with recombinant CAMP factor (25 ug/ml) or GFP at 37° C. for 18 hr. After the incubation, cell viability was determined and cytotoxicity was calculated. The data are presented as mean±SE (n=6, $p<0.0005$*** by Student's t-test).

The effect of combining CAMP factor vaccination with local injection of anti-ASMase IgG on *P. acnes*-induced inflammation ICR mice were vaccinated with CAMP factor or GFP control. *P. acnes* or PBS was injected intradermally into the ears of vaccinated mice. Thirty min after challenge, the left ear (received *P. acnes*) was locally injected with goat anti-ASMase IgG or normal goat control IgG, while the right ear was injected with an equal volume of PBS. Both the combination of GFP vaccination with local injection of anti-ASMase IgG and CAMP factor vaccination with local injection of normal IgG reduced *P. acnes*-induced ear swelling to 202.8% and 193.5% 24 hr after bacterial challenge, respectively, in comparison with GFP vaccination combined with normal IgG injection (224.5%). By contrast, the combination of CAMP factor vaccination with local injection with anti-ASMase IgG synergistically decreased *P. acnes*-induced ear swelling to 153.7% (FIG. 14). These data indicate that suppression of both of bacterial CAMP factor and host ASMase synergistically reduced *P. acnes*-induced inflammation and skin lesions.

To determine antibody titers to CAMP factor by enzyme-linked immunosorbent assay (ELISA), purified CAMP factor (5 μg/ml) was diluted with a coating buffer (0.015 M Na2CO2, 0.35 M NaHCO$_2$ and 0.05% NaN$_3$), and coated onto a 96-well ELISA plate (Corning, Lowell, Mass.) at 4° C. overnight. The plates were washed with PBS containing 0.1% (w/v) Tween-20, and blocked with PBS containing 1% (w/v) BSA and 0.1% (w/v) Tween-20 for 2 hr at room temperature. Antisera (10,000 dilutions) obtained from mice vaccinated with *E. coli* over-expressing CAMP factor or GFP were added to the wells and incubated for 2 hr. Goat anti-mouse IgG (H+L) IgG-horseradish peroxidase (HRP) conjugate (Promega, Madison, Wis.) (1:5,000 dilution) was added, incubated for 2 hr, and then washed. HRP activity was determined with a OptEIA™ Reagent Set (BD Biosciences, San Diego, Calif.). The OD of each well was measured at 450 nm.

Therapeutic Effects of Vaccination with CAMP Factor on *P. Acnes*-Induced Inflammation.

Live *P. acnes* ($1 \times 10^7$ CFU/20 ul) in PBS were intradermally injected in the central portion of the left ear. Twenty μl of PBS was injected into the right ear of the same mouse as a control. To examine in vivo therapeutic effects of vaccination, ICR mice were vaccinated with *E. coli* over-expressing CAMP factor or GFP 24 hr after bacterial challenge as described above. The ear thickness was measured using a micro caliper for 98 days and a *P. acnes*-induced increase in ear thickness reported as % of ear thickness in PBS-injected ears.

Co-cytotoxic activity of CAMP factor and bacterial SMase. The human keratinocyte cell line, HaCaT, or murine macrophage cell line, RAW264.7, was cultured in DMEM or RPMI1640 medium, respectively, supplemented with 10% heat-inactivated FBS, at 37° C. under atmosphere of 5% (v/v) CO2 in air. For determination of co-cytotoxic activity of SMase and CAMP factor, cells ($1 \times 10^5$/well) were preincubated in a 96-well plate at with SMase from *S. aureus* (350 mU/ml, Sigma) or an equal amount of PBS (vehicle control) in serum-free medium containing 10 mM $MgCl_2$ for 15 min. After the pretreatment, the cells were washed with PBS and then incubated with CAMP factor (25 μg/ml) or GFP as a control in 1% serum-medium for 18 hr. As a positive control for 100% cytotoxicity, triton-X was added to get a final concentration of 0.1% (v/v) for cell lysis. After the incubation, cell viability was determined as described in Experimental procedures and cytotoxicity was calculated as the percentage of cell death caused by triton-X.

The hemolytic power is thought to be a virulence factor for numerous microbial pathogens to degrade tissue, invade host cells, disseminate themselves, and escape from the host immune attack. Microbial hemolysins generally possess the capacity to lyse erythrocytes in vitro, but many are toxic to other cell types as well. *P. acnes* secretes CAMP factor as an exotoxin (FIG. 11). Although the hemolytic action of CAMP factor has been demonstrated on erythrocytes and artificial plasma membranes, little attention has been paid to the cytotoxicity of CAMP factor on other cell types. Therefore, the cytotoxic activity of CAMP factor on host cells was examined, and its physiologic significance to the pathogenicity of *P. acnes*, which is relevant to inflammatory acne vulgaris.

The human keratinocyte is one of the major targets of *P. acnes*. In addition, intradermal injection of mouse ears with live *P. acnes* induces infiltration of numerous CD11b+ macrophages (FIGS. 13B and C). The tissue chamber model data integrated with a dermis-based cell-trapped system was used to mimic the in vivo microenvironment of acne lesions, injection of live *P. acnes* into the intradermally-implanted tissue chamber attracts Gr-1+ neutrophils and CD11b+ macrophages into the chamber. Thus, the interaction between murine macrophage and *P. acnes* is investigated in our model of *P. acnes*-induced inflammation in mice. Therefore, the human keratinocyte cell line, HaCaT, and the murine macrophage cell line, RAW264.7, were employed to determine cytotoxic activity of CAMP factor from *P. acnes* in vitro. The data indicate that CAMP factor is an important virulence factor for *P. acnes* to degrade host cells (FIG. 17G).

Figure 17:
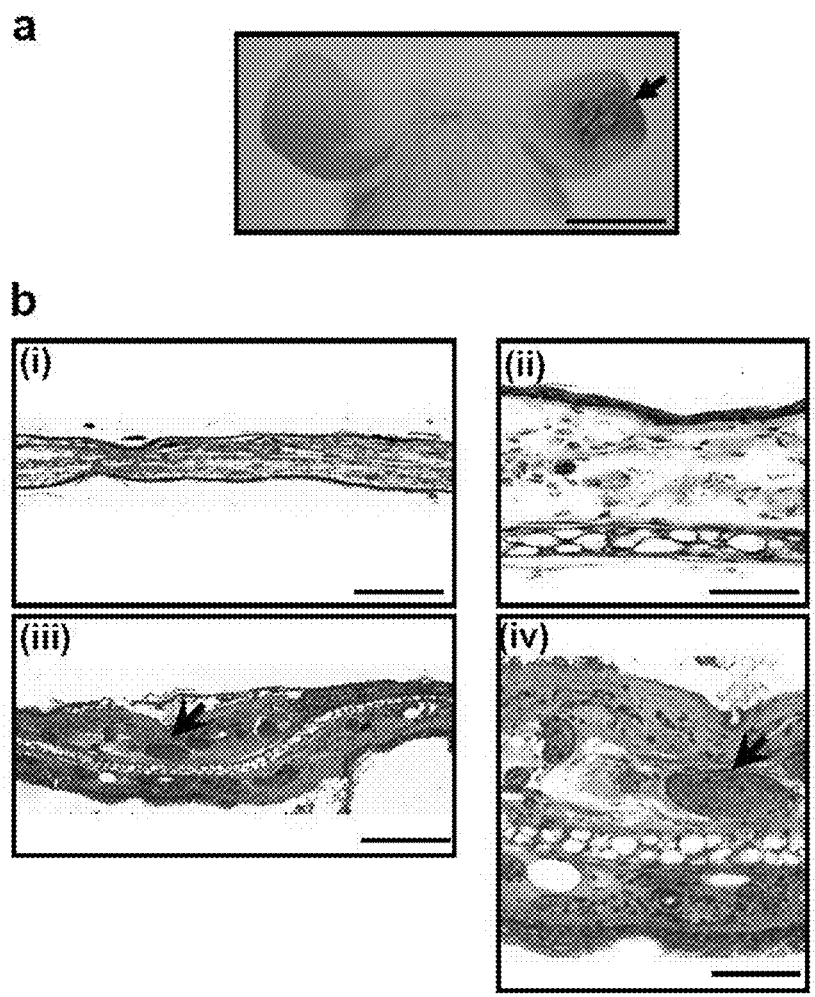
FIG. 17A-B shows *P. acnes* CAMP factor exerted virulence activity. Ears of ICR mice were injected intradermally with recombinant GFP (left ear) and CAMP factors (right ear). (A) Inflammation-induced ear redness (arrow) was visualized 24 h after injection. (B) Ear swelling was observed in an H&E-stained frozen tissue section of GFP- (I, iii) or CAMP factor (ii, iv)-injected ear. The magnified images [4× (i, iii) and 20× (ii, iv)] indicated the deposits of ruptured erythrocytes (arrowheads). Bars (a)=1 cm. Bars [b(I, iii)]=2 mm. Bars [b(ii, iv)]=0.5 mm.

Evidences obtained from a number of in vitro experiments suggest only weak hemolytic activities of CAMP factor co-hemolysin itself without SMases. CAMP factor does not have significant homology to any other pore-forming toxins. Only the full-length recombinant CAMP factor has been found to exert co-hemolytic activity on a sheep blood agar plate, but the structure-function relationship remains unclear. Lang and co-authors indicate that GBS CAMP factor binds to glycosylphosphatidylinositol (GPI)-anchored proteins on the cell membrane of erythrocytes, which act as cell surface receptors for this toxin, and that the interaction supports its ability to form oligomeric pores in sheep erythrocyte membranes. Amount of GPI-anchored proteins is augmented by the reduction of sphingolipid levels on the cell membrane. Since GPI-anchored proteins are found ubiquitously in mammalian cells, the same mechanism may be involved in the cytotoxic reaction of CAMP factor on keratinocytes and macrophages. Indeed, the removal of sphingomyelin on the cell membrane by pretreating with bacterial SMase increased the cell susceptibility to CAMP factor (FIG. 17).

Figure 18:
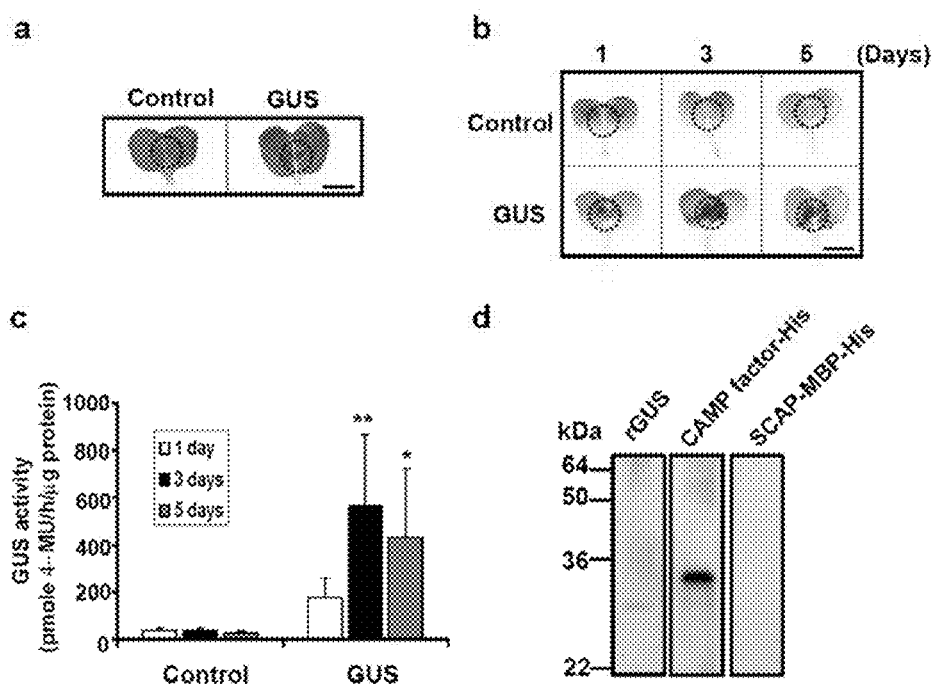
FIG. 18A-D shows transiently express CAMP factors and GUS in radish leaves. (a) Leaves of radish (*Raphanw sativus* L.) were infiltrated with *A. tumefaciens* (LBA4404 strains) transforming a 35S::GUS construct (right). Leaves infiltrated with non-transformed LBA4404 cells (left) served as negative controls. Dotted circles indicate locations of syringe infiltration with *A. tumefaciens*. Blue stained areas indicate the GUS expression. The dynamic pattern of GUS expression in radish leaves from 1 to 5 days after infiltration was analyzed by (b) histochemical and (c) GUS activity assays. (*$P<0.05$ and **$P<0.005$, by Student's t-test). (d) Detection of CAMP factor expression by Western blot analysis. Ground radish leaves (20 µg) infiltrated with *A. tumefaciens* carrying a 35S:: CAMP factor-His (CAMP factor-His), a $^{35}$S::SCAP-MBP-His (SCAP-MBP-His) or recombinant GUS (rGUS) were run on a 10% (w/v) SDS-PAGE and blotted onto a nitrocellulose membrane. The membranes were then probed with anti-CAMP factor serum produced by mice immunized with UV-irradiated *E. coli*, BL21 (DE3) over-expressing CAMP factor. An arrow indicates CAMP factor appearing at a molecular weight of 29 kDa. Bar=6 mm.

Several different forms of mammalian SMases have been identified, including endosomal/lysosomal ASMase (a soluble enzyme), which is ubiquitous in mammalian tissues, and plasma membrane-associated, or cytosolic, neutral SMase, which is located mostly in the central nervous system. These enzymes catalyze the hydrolytic cleavage of sphingomyelin on the cell membrane to ceramide in the same catalytic mechanism as bacterial SMases. The released ceramide, in turn, can act as a cellular signal for various activities, including apoptosis, differentiation, and proliferation. The activity of the SMases are regulated by a wide range of extracellular signaling; growth factors, cytokines, neurotransmitters, hormones, and stresses, such as ultraviolet and reactive oxygen species. Ubiquitously-expressed ASMase exerts important functions during the innate immune response to infectious pathogens. Therefore, focus was put on the interaction of host ASMase and bacterial CAMP factor as related to pathogenicity of *P. acnes*. ASMase was released and/or secreted from the host cells when the cells were co-cultured with *P. acnes* (FIG. 18A). The cytotoxicity of *P. acnes* was neutralized in the presence of mouse anti-CAMP factor antiserum in vitro (FIG. 18B). In addition, adding the specific ASMase inhibitor, desipramine, to co-cultured cells and *P. acnes* significantly reduced the cytotoxicity. The data from the in vitro experiments suggest that CAMP factor is a potential virulence factor for *P. acnes* and involvement of host ASMase in the virulence of *P. acnes*.

There have been only a few studies showing that CAMP factor is a potential virulence of pathogen in vivo. A high dose of partially purified CAMP factor from GBS was lethal to rabbits and mice when injected intravenously. Mice that had been infected with sublethal doses of GBS developed fetal septicemia after receiving repeated injections with purified CAMP factor. The disclosure demonstrates that intradermal injection of the mouse ears with recombinant CAMP factor induced ear swelling, indicating that CAMP factor is involved in *P. acnes*-induced inflammation and skin lesion in vivo.

Figure 19:
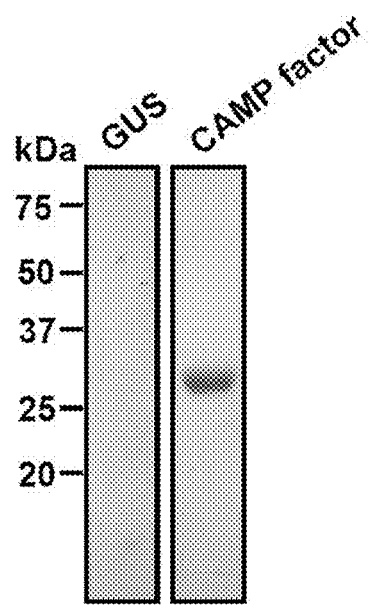
FIG. 19 shows mice immunized with CAMP factor-encapsulated leaves produced CAMP factor specific antibodies. Purified CAMP factor (65 µg) run on a 100 (w/v) SDS-PAGE was blotted onto a nitrocellulose membrane and immunoreacted to sera obtained from mice immunized with leaves encapsulating GUS (left) or CAMP factors (right). A single band with 29 kDa indicates the purified CAMP factor reactive to serum from CAMP factor-immunized mice, verifying the immunogenicity of CAMP factor.
Figure 20:
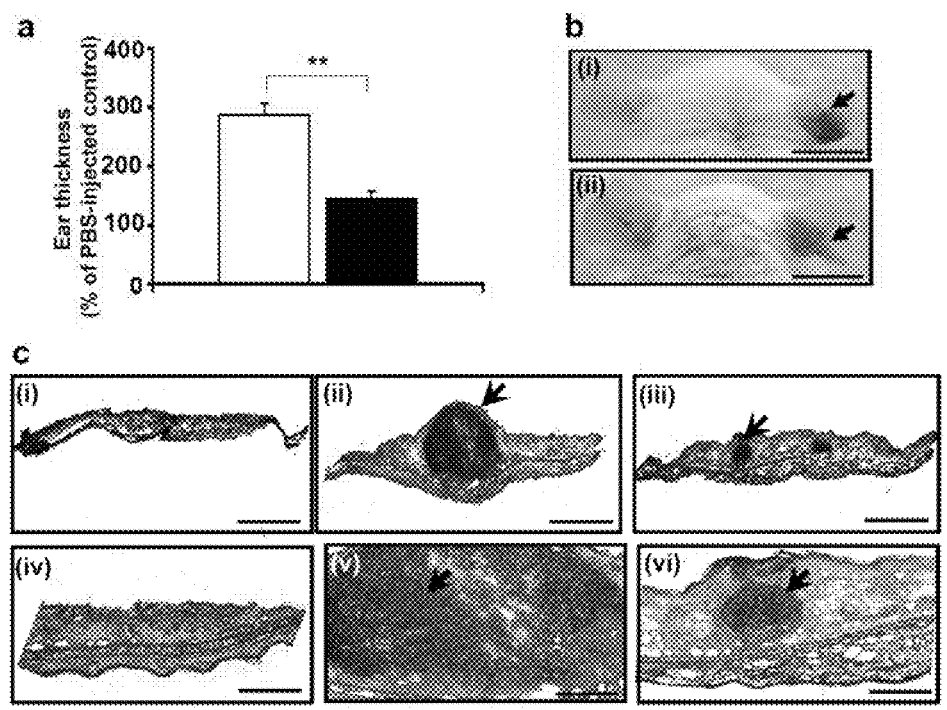
FIG. 20A-C shows that passive immunization of mice with neutralizing antibody to CAMP factor diminished *P. acnes*-induced inflammation. (A) 5% (v/v) anti-GUS (open circles) or anti-CAMP factor (solid circles) serum-treated *P. acnes* ($1 \times 10^7$ CFUs) was inoculated into the right ears of ICR mice to induce an increase in ear thickness as described in the "Materials and Methods". As a control, an equal volume of PBS was injected into the left ears of the same mice. Ear thickness was measured with a micro-caliper at the indicated times after bacterial injection. The ear thickness of *P. acnes*-injected ear was calculated as % of a PBS-injected control. Error bars represented mean±SE of four mice (**$P<0.005$, by Student's t-test). (B) Ear redness (arrows) was visualized 3 days after injection with anti-GUS serum (i) or anti-CAMP factor (ii) serum treated-*P. acnes* ($10^7$ CFUs). Bar=1 cm. (C) Ear inflammation was observed in an H&E-stained frozen tissue section of ear injected with PBS alone (i, iv) or *P. acnes* treated with anti-GUS (ii, v) or anti-CAMP factor (iii, vi) serum. The granulamatous reactions (arrowheads) were visualized under magnification 4× (i, ii, iii; bars=2 mm) and 20× (iv, v, vi; bars=0.5 mm).
Figure 21:
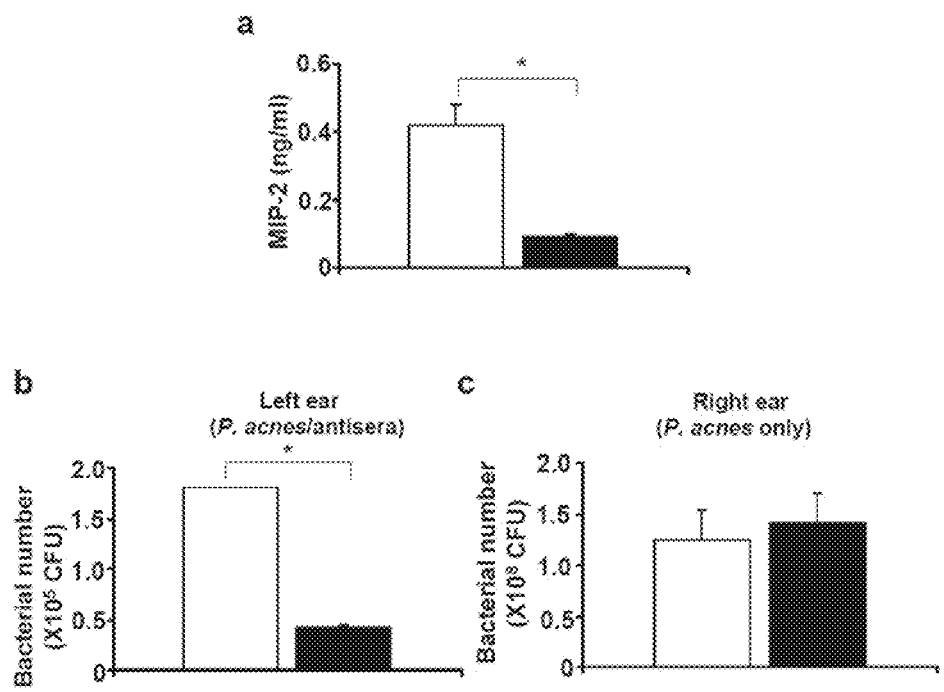
FIG. 21A-C shows passive neutralization of *P. acnes* CAMP factor reduced the production of pro-inflammatory MIP-2 cytokine and bacterial colonization without altering *P. acnes* survival at other body sites. (A) Measurement of pro-inflammatory MIP-2 cytokine was carried out by a sandwich ELISA using a Quantikine M mouse MIP-2 set. Compared to the neutralization with anti-GUS serum (open bar), passive neutralization with anti-CAMP factor serum (solid bar) markedly suppressed the *P. acnes*-induced increase in MIP-2. (B) The left ears of mice were injected with *P. acnes* ($1 \times 10^7$ CFUs) in the presence of anti-GUS serum (open bar) or anti-CAMP factor serum (solid bar). (C) The right ears were injected with live *P. acnes* ($1 \times 10^7$ CFUs) alone. Bacterial colonization (CFUs) was quantified in agar plates as described in "Materials and Methods. Error bars represent mean±SE of four mice (*$P<0.05$, by Student's t-test).
Figure 22:
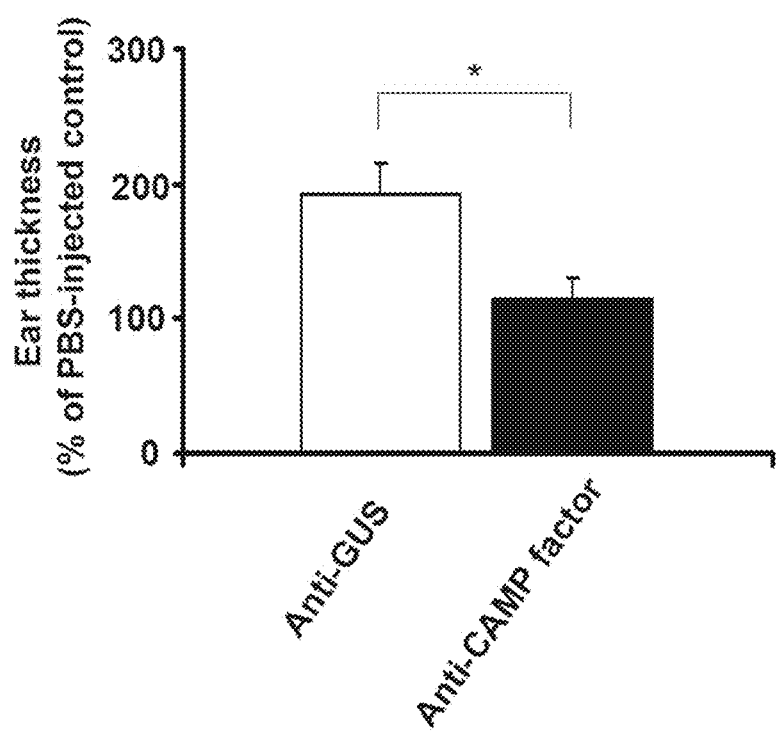
FIG. 22 shows that vaccination with CAMP factor conferred protective effect on *P. acnes*-induced ear swelling. Seven weeks after vaccinated with GUS- (open bar) and CAMP factor (solid bar), mice were challenged intradermally with an amount of 25 µl aliquots of live *P. acnes* ($1 \times 10^7$ CFUs) suspended in PBS overnight to right ears. As a control, 25 µl of PBS was injected into the left ear of the same mice. The increase in ear thickness was measured using a micro caliper after the bacterial challenge. The increase in ear thickness of *P. acnes* challenged ear was calculated as % of a PBS-injected control.

To examine whether host ASMase is involved in *P. acnes* pathogenicity and *P. acnes*-induced inflammation, the ears of ICR mice were injected intradermally with *P. acnes* according to a rat ear model previously described. The amount of soluble ASMase increased in the ear after injection with *P. acnes* (FIG. 13A). The profile of the granulomatous inflammation in the mouse ear model (FIGS. 13B and C) is similar to that of inflammatory acne in the human hair follicle; numerous *P. acnes* were observed inside phagosomes of an infiltrating macrophage in an inflammatory acne lesion in the hair follicle. *P. acnes* resists killing by phagocytes and is able to survive in macrophages. GBS beta-hemolysin/cytolysin, a pore-forming exotoxin, was demonstrated to contribute to the subversion of phagocytic host immune defenses. During the intracellular life cycle of *Listeria monocytogenes*, a pore-forming toxin named listeriolysin O is largely responsible for mediating rupture of the phagosomal membrane to allow its escape from the phagosome into the host cytosol, its replicative niche. Lysosomal ASMase is known to contribute to macrophage killing of bacteria in the early stage of phagocytosis, and is required for the proper fusion of late phagosomes with lysosomes, which is crucial for efficient transfer of lysosomal antibacterial hydrolases into phagosomes. Taken together, phagocytosed *P. acnes* in the macrophage may take advantage of the host lysosomal ASMase to enhance the toxicity of CAMP factor to escape from phagosomes, an interaction which may be involved in the *P. acnes* resistance against phagocytosis. Indeed, we observed a number of macrophages in the *P. acnes*-challenged ear, many of which had cell membrane that were ruptured by colonizing *P. acnes* (FIG. 19D). Infection by *Salmonella* or *E. coli* triggered an early surge in the extracellular secretion and/or release of ASMase activity from macrophages. *P. acnes* may shrewdly utilize released and/or secreted ASMase from macrophages to invade or to escape cells to spread cell-to-cell.

An effective vaccines for *P. acnes*-associated inflammation as an alternative treatment for acne consist of killed-whole organism *P. acnes* and a *P. acnes* cell wall-anchored sialidase. Thus, the potential of CAMP factor as a target of acne vaccine development was examined. *P. acnes* CAMP factor was highly immunogenic when vaccination was performed by an *E. coli*-based vaccine delivery system (FIGS. 11D and E). The vaccination with *P. acnes* CAMP factor elicited protective immunities to *P. acnes*-induced inflammation. In addition, a local injection mouse ear with anti-ASMase IgG reduced *P. acnes*-induced inflammation. The combination of CAMP factor vaccination with a local injection of anti-ASMase IgG synergistically reduced *P. acnes*-induced ear swelling (FIG. 14). The data suggests the synergistic interaction of CAMP factor and host ASMase in vivo.

*P. acnes* Utilized Host ASMase to Amplify its CAMP Factor-Mediated Pathogenicity.

Lysosomal ASMase in macrophages play important roles during the innate immune response to infectious pathogens; the enzyme contributes to macrophage mediated killing of pathogens and lysosomal fusion with phagosomes. However, *P. acnes* may hijack ASMase released and/or secreted from host cells to enhance its CAMP factor-delivered pathogenicity. The synergism may contribute to its evasion of host immune defenses, degrade host tissues and spread the pathogen cell-to-cell. Recent studies have afforded abundant evidences showing that *P. acnes* is involved not only in acne vulgaris, but also in many diseases, including endocarditis, endophthalmitis, osteomyelitis, joint, nervous system, cranial neurosurgery infections, and implanted biomaterial contamination. Treatment targeting *P. acnes* CAMP factors and host ASMase may have a potential to be widely applied for these *P. acnes*-associated diseases to suppress the pathogen expansion.

Plant Materials.

Japanese radish sprouts (Kaiware-daikon) (*Raphanus sativus* L.) was obtained from a commercial supplier (ICREST International, JCP, Carson, Calif.). Japanese radish sprouts that were 9 cm in length with two leaflets were used and grown at room temperature under a 23 Watt fluorescent bulb (Philips, Portland, Oreg.), and were sprayed with water daily.

Vector construction. The binary vector pBI121 harboring the reporter GUS driven by the cauliflower mosaic virus 35S promoter was used for gene construction (Jefferson, 1987). The open reading frames of CAMP factor cDNA cloned in a pEcoli-Nterm 6xHN vector was amplified by PCR using a forward primer (5'-CCTTCTAGAGGAGATATAC-CATGGGTCATAATCAT-3'; SEQ ID NO:18) and a reverse primer (5'-TCCCCCGGGTTAATTAATTAAGCGGC-CGCC-3' (SEQ ID NO:19). The SCAP cDNA cloned in a pIVEX-MBP vector (Liu et al., 2008) was amplified using a forward primer (5'-AGATCTAGAATGTCTGGTTCTCAT-CATCATCATC-3'; SEQ ID NO:20) and a reverse primer (5'-GCCCCCGGGTTAGCCTTCGATCCCGAGGTT-3' (SEQ ID NO:21). The primers were designed to add restriction sites to the ends of PCR products. Specifically, the restriction sites XbaI and SmaI were encoded into the forward and reverse primers, respectively. PCR products were treated with XbaI and SmaI then cloned into polylinker sites of pBI121 vectors to generate 35S::CAMP factor-His and 35S::SCAP-MBP-His constructs.

*Agrobacterium tumefaciens* Transformation.

All constructs were transformed into an *Agrobacterium tumefaciens* strain LBA4404 using a liquid nitrogen freeze-thaw method (An et al., 1988). A single colony of LBA4404 cells was inoculated in 5 ml of YEP medium [10 mg/ml bacto-trypton (DIFCO, Detroit, Mich.), 10 mg/ml yeast extract (DIFCO, Detroit, Mich.), and 5 mg/ml NaCl (Sigma, St. Louis, Mo.; pH 7.5)] with 250 rpm shaking at 28° C. overnight. Subsequently, 50 ml of fresh YEP was inoculated with 2 ml of liquid culture and incubated with 250 rpm shaking at 28° C. until the $OD_{600}$ reached 0.8. The bacteria were centrifuged at 3,000×g for 5 min at 4° C. and the pellet was resuspended in 1 ml of 20 mM calcium chloride. The bacteria (0.2 ml) were transferred to a 1.5 ml microfuge tube and 1 µg of gene constructs was added. The mixture was frozen in liquid nitrogen for 5 min then thawed at 37° C. water bath for 5 min. One ml of YEP medium was added to the mixture and incubated with 150 rpm shaking at 28° C. for 2 to 4 h. The bacteria were centrifuged at 3,000×g for 5 min then resuspended in 0.1 ml of YEP. Transformants were selected by plating bacteria on YEP-agar medium (YEP medium containing 1.5% agar) containing antibiotics (50 µg/ml kanamycin and 50 µg/ml streptomycin) and incubating at 28° C. for 2 to 3 days.

Agroinfiltration of Gene Constructs into Leaves and Protein Extraction.

A single colony of *A. tumefaciens* transformants was cultured in 2 ml of YEP medium containing 50 g/ml kanamycin and 50 g/ml streptomycin with 250 rpm shaking at 28° C. until $OD_{600}$ reached approximately 0.5. Afterward, the bacteria were collected by centrifugation at 1,300×g for 5 min, and resuspended in 2 ml sterile $ddH_2O$. All bacterial suspensions were maintained at room temperature for 30 min until agroinfiltration. Non-transformed *Agrobacterium* served as a negative control and was cultured under the same conditions as the transformants without adding kanamycin in the medium. For syringe infiltration, the central lower epidermises (i.e., the centermost 25 $mm^2$ area) of potted seedlings leaves were wounded with a sterile scalpel (number 15, Feather Safety Razor Co., Osaka, Japan) and 0.1 ml of *Agrobacterium* bacterial suspension ($5 \times 10^7$ CFUs) was injected into the wound site, which was positioned between a finger and a 1 ml syringe (BD, Bioscience, San Diego, Calif.). Infiltration was confirmed by visually monitoring the diffusion of bacterial suspension toward the leaf margin (Schob et al., 1997). Agroinfiltrated leaves were grown for five days before GUS assays and immunization was performed. Agroinfiltrated leaves were stained using a histochemical GUS assay solution consisting of 0.1 M $NaPO_4$ (pH 7.0), 0.5 mM $K_3Fe(CN)_6$, 0.5 mM $K_4Fe(CN)_6$, 0.1% (v/v) Triton X-100, and 0.05% (w/v) 5-bromo-4-chloro-3-indolyl-beta-D-glucuronic acid, cyclohexylammonium salt (Sigma, St. Louis, Mo.). Leaves were submerged in the staining solution and incubated at 37° C. in the dark overnight. After incubation, leaves were removed from the staining solution and immersed in a stop solution containing 42.5% (v/v) ethanol, 10% (v/v) formaldehyde, and 5% (v/v) acetic acid (Jefferson, 1987). Quantitative determination of GUS activity was accomplished by the fluorometric assay. Whole leaves were grounded with 200 µl of 1×CCLR [100 mM K-phosphate (pH 7.8), 1 mM EDTA, 10% (v/v) glycerol, 10 (v/v) Triton X-100 and 7 mM β-mercaptoethanol]. The mixture was centrifuged at 10,000×g for 5 min at 4° C. and 200 µl supernatant was removed to a new microtube on ice following by mixing with 1 mM 4-Methylumbelliferyl-D-glucuronide buffer at 37° C. for 1 h (Jefferson, 1987). The enzymatic reaction was measured spectrofluorometrically with excitation at $OD_{365}$ and emission at $OD_{455}$ by SpectraMAX GeminiEM spectrofluorometer (Molecular Devices, Sunnyvale, Calif.). To investigate the dynamic expression of antigen in radish leaves, leaves were removed at 0, 1, 3, and 5 days to quantify the level of GUS.

Purification of CAMP factor and SCAP from leaf tissues were carried out by affinity chromatography on a Ni-NTA agarose column (Qiagen, Valencia, Calif.) with certain modifications. The column was washed with water and equilibrated with buffer A (8 M guanidine, 100 mM $NaH_2PO_4$, 10 mM Tris-HCl, pH 8.0). Leaf material (1 g) was ground under liquid nitrogen using mortar and pestle in 15 ml ice-cold extraction buffer A. Guanidine-solubilized proteins were centrifuged at 12,000×g for 20 min to remove the debris and insoluble material and the supernatant was gently stirred with 1.6 ml Ni-NTA agarose resin for 1 h at room temperature. The mixture was loaded onto a column previously equilibrated with buffer A. Briefly, the column was washed with buffer B (8 M urea, 100 mM $NaH_2PO_4$, 10 mM Tris-HCl, pH 6.8). Finally, proteins were eluted with buffer C (8 M urea, 100 mM $NaH_2PO_4$, 10 mM Tris-HCl, pH 6.3), D (8 M urea, 100 mM $NaH_2PO_4$, 10 mM Tris-HCl, pH 5.9), and buffer E (8 M urea, 100 mM $NaH_2PO_4$, 10 mM Tris-HCl, pH 4.5).

Intranasal Immunization with Whole Leaves Containing Recombinant CAMP Factors.

Female ICR mice (3 to 6 weeks old; Harlan, Indianapolis, Ind.) were utilized for intranasal immunization that holds the potential to induce a mucosal immune response (Mantis, 2005). Mice were maintained in accordance to institutional guidelines. The central areas (25 $mm^2$) of five radish leaves expressing GUS or CAMP factors alone were excised using a sterile scalpel. To avoid *Agrobacterium* transgene introgression, leaf sections were pooled and ground in 700 µl ddH$_2$O and then sterilized by an UV crosslinker (Spectronics, Westbury, N.Y.) at 7,000 J/m$^2$ for 30 min. Inactivation of sterilized *Agrobacterium* was confirmed by their inability to form colonies on YEP agar plates (data not shown). Whole leaves containing either CAMP factor or GUS alone (as a negative control) without adjuvants were then intranasally inoculated into the nasal cavities of ICR mice (25 µl/mouse). Three boosts at the same dose were performed at 1, 2, and 4 weeks after the first immunization.

To detect antigen expression, 15 µg recombinant GUS and 15 µg of whole leaves expressing CAMP factors or SCAP alone were separated using 10% SDS-PAGE. Bands were electrophoretically transferred to nitrocellulose membranes (Gil et al., 2006). Membranes were probed with anti-CAMP factor serum obtained from mice immunized with UV-irradiated *E. coli*, BL21 (DE3) (Liu et al., 2008) over-expressing *P. acnes* CAMP factors. To confirm antibody production in the immunized mice, purified CAMP factor (65 µg) was loaded into a 10% SDS-PAGE and transferred to a nitrocellulose membrane. The blot was immuno-reacted to serum (1:500 dilution) obtained from mice immunized for four weeks with whole leaves containing CAMP factor. Antibodies [Immunoglobulin G (IgG)] were detected with anti-mouse horseradish peroxidase-conjugated IgG (1:5,000 dilution, Promega, Madison, Wis.). Peroxidase activity was visualized with a western lighting chemiluminescence kit (PerkinElmer, Boston, Mass.).

Passive Immunization of Anti-CAMP Factor Serum Against *P. Acnes*-Induced Inflammation.

Complements in the serum were inactivated by heating at 56° C. for 30 min. *P. acnes* was pre-treated with 5% (v/v) inactivated anti-GUS serum or anti-CAMP factor serum in the medium at 37° C. for 2 h. The 2 h incubation of anti-GUS serum (3.63±1.47×10$^8$ CFUs) and anti-CAMP factor serum (3.3±1.2×10$^8$ CFUs), respectively, did not significantly influence the growth of *P. acnes*. ICR mice were injected intradermally with an amount of 25 l aliquots of anti-GUS or anti-CAMP neutralized *P. acnes* (1×10$^7$ CFUs) suspended in PBS overnight. As a control, 25 l of PBS was injected into the right ear of the same mice. The increase in ear thickness was measured using a micro caliper (Mitutoyo, Japan) after the bacterial injection, the increase in ear thickness of *P. acnes* injected ear was calculated as % of a PBS-injected control. For histological observation, the ear on the day 3 after injection was excised, cross-sectioned, stained with H&E, and viewed on a Zeiss Axioskop2 plus microscope. To count the bacterial colonization, the bacteria-injected ears were homogenized in 1 ml of sterile PBS for 1 min on a vibrating homogenizer (mini-beadbeater, Biospec Products, Bartlesville, Okla.) in the presence of 0.5 ml of 2.0 mm zirconia beads (Biospec Products, Bartlesville, Okla.). The bacterial number in homogenates was quantified by serially diluting the bacteria and plating them on a RCM plate. After centrifugation at 1,300×g, MIP-2 in supernatants was measured by an ELISA kit as directed by the manufacturer (BD Biosciences, San Diego, Calif.).

To investigate whether passive administration of neutralizing antiserum influences the survival of *P. acnes* at other sites, the left ears of ICR mice were injected intradermally with an amount of 25 l aliquots of anti-GUS serum or anti-CAMP factor serum neutralized *P. acnes* (1×10$^7$ CFUs). The same amount of live *P. acnes* (1×10$^7$ CFUs) alone was injected into the right ears of the same mice overnight. The bacteria number was calculated by counting colonies on RCM plates.

Compared to active immunization of a CAMP factor-targeted vaccine, passive neutralization of CAMP factor displays roughly equal potency with respect to suppression of *P. acnes*-induced ear inflammation. The therapeutic antibodies to CAMP factors described herein can be extended for treatment of various *P. acnes*-associates human diseases including implant infections, pulmonary sarcoidosis, osteomyelitis, and endocarditis (Nakatsuji et al., 2008c; Nishiwaki et al., 2004; Zouboulis, 2004). With an eye toward human use, future studies will include generating the therapeutic monoclonal antibodies to *P. acnes* CAMP factor. Epicutaneous application of a human monoclonal antibody to CAMP factor onto the skins of patients with severe acne may locally eradicate *P. acnes* without interrupting the residence of *P. acnes* and other commensals in other locations of our body.

The following sequences are referenced herein. GenBank accession no. NC_006085 (the full genome of *P. acnes*, the sequence of which is incorporated herein by reference. The polypeptide sequence of *P. acnes* CAMP Factor identified as SEQ ID NO:7 and the corresponding coding polynucleotide identified as SEQ ID NO:6; and the polypeptide for lipase identified herein as SEQ ID NO:9 and the corresponding coding polynucleotide sequence identified as SEQ ID NO:8. Human ASMase is identified as SEQ ID NO:11; and the corresponding coding polynucleotide sequence as SEQ ID NO:10. Homologs and variants of ASMase's are known. For example, sphingomyelin phosphodiesterase 1, acid lysosomal isoform 2 precursor [*Homo sapiens*] gi|56117842|ref|NP_001007594.1|[56117842]; sphingomyelin phosphodiesterase 1, acid lysosomal isoform 1 precursor [*Homo sapiens*] gi|56117840|ref|NP_000534.3|[56117840]; sphingomyelin phosphodiesterase 1, acid lysosomal [*Mus musculus*]gi|6755582|ref|NP_035551.1|[6755582]; Sphingomyelin phosphodiesterase 1, acid lysosomal [*Mus musculus*] gi|21961231|gb|AAH34515.1|[21961231]; Sphingomyelin phosphodiesterase 1, acid lysosomal [*Mus musculus*] gi|15030106|gb|AAH11304.1|[15030106], the sequences associated with the accession number are incorporated herein by reference. *P. acnes* sialidase sequence is provided in SEQ ID NO:13 and the corresponding polynucleotide in SEQ ID NO:12. *P. acnes* sialidiase B is provided in SEQ ID NO:15 and the corresponding polynucleotide in SEQ ID NO:14. A sialidase-like polypeptide and coding sequence are provided in SEQ ID NOs: 17 and 16, respectively.

What is claimed is:

1. An immunogenic composition comprising an attenuated bacterial vector that expresses a polypeptide comprising SEQ ID NO: 9 or 11 and/or an attenuated bacterial vector that expresses a peptide consisting of SEQ ID NO:2 or 3; wherein the composition is useful for inducing an immunoprotective response against Propionibacterium acnes (P. acnes).

2. The immunogenic composition of claim 1, wherein the polypeptide consists of the sequence of SEQ ID NO: 9 or 11.

3. The immunogenic composition of claim 1, wherein the attenuated bacterial vector comprises an E. coli.

4. The immunogenic composition of claim 1, wherein the composition comprises at least one attenuated bacterial vector expressing the polypeptide of SEQ ID NO: 9 or 11 or the peptide consisting of the sequence of SEQ ID NO:2 or 3.

5. A method of inducing protective immunity in a subject comprising administering the composition of claim 1 to the subject.

6. An immunoprotective composition comprising at least one attenuated bacterial vector expressing an antigen useful for inducing an immunoprotective response against Propionibacterium acnes (P. acnes), said antigen comprising the polypeptide of SEQ ID NO: 9 or 11, and/or the peptide consisting of SEQ ID NO:2 or 3 linked to transcriptional promoter and termination signals.

7. The immunoprotective composition of claim 6, wherein the at least one attenuated bacterial vector is selected from the group consisting of Campylobacter jejuni, Campylobacter coli, Listeria monocytogenes, Yersinia enterocolitica, Yersinia pestis, Yersinia pseudotuberculosis, Escherichia coli, Shigella flexneri, Propionibacterium acnes, Shigella dysenteriae, Shigella boydii, Helicobacter pylori, Helicobacter felis, Gastrospirillum hominus, Vibrio cholerae, Vibrio parahaemolyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Streptococcus gordonii, Lactobacillis sp., Klebsiella pneumoniae, Enterobacter cloacae, and Enterococcus faecalis.

8. The immunoprotective composition of claim 6, wherein the composition further provides protective immunity against an infection by K. pneumoniae, S. aureus and/or S. pyogenes.

9. A method of protecting a susceptible host against an infection of Propionibacterium acnes (P. acnes) comprising administering to said host an amount of the immunoprotective composition of claim 6 sufficient to invoke an immunoprotective response in the host.

10. A recombinant attenuated bacterial vector comprising a polynucleotide encoding an antigenic polypeptide comprising SEQ ID NO: 9 or 11, or an antigenic peptide consisting of SEQ ID NO:2 or 3.

11. A method of providing protective immunity to a subject, comprising administering the recombinant attenuated bacterial vector of claim 10 to a subject.

12. The immunoprotective composition of claim 6, wherein the polypeptide consists of SEQ ID NO: 9 or 11.

13. The recombinant bacterial vector of claim 10, wherein the polynucleotide encodes an antigenic polypeptide consisting of SEQ ID NO: 9 or 11.

14. An immunogenic composition comprising an attenuated bacterial vector that expresses a polypeptide comprising SEQ ID NO: 7, 9 or 11 and/or expresses a peptide consisting of SEQ ID NO:2 or 3; wherein the composition is useful for inducing an immunoprotective response against Propionibacterium acnes (P. acnes) and wherein the attenuated bacterial vector is selected from the group consisting of Campylobacter jejuni, Campylobacter coli, Listeria monocytogenes, Yersinia enterocolitica, Yersinia pestis, Yersinia pseudotuberculosis, Escherichia coli, Shigella flexneri, Shigella dysenteriae, Shigella boydii, Helicobacter pylori, Helicobacter felis, Gastrospirillum hominus, Vibrio cholerae, Vibrio parahaemolyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Streptococcus gordonii, Lactobacillis sp., Klebsiella pneumoniae, Enterobacter cloacae, and Enterococcus faecalis.

15. An immunoprotective composition comprising at least one attenuated bacterial vector expressing an antigen useful for inducing an immunoprotective response against Propionibacterium acnes (P. acnes), said antigen comprising the polypeptide of SEQ ID NO:7, 9 or 11, and/or the peptide consisting of SEQ ID NO:2 or 3 linked to transcriptional promoter and termination signals and wherein the at least one attenuated bacterial vector is selected from the group consisting of Campylobacter jejuni, Campylobacter coli, Listeria monocytogenes, Yersinia enterocolitica, Yersinia pestis, Yersinia pseudotuberculosis, Escherichia coli, Shigella flexneri, Shigella dysenteriae, Shigella boydii, Helicobacter pylori, Helicobacter felis, Gastrospirillum hominus, Vibrio cholerae, Vibrio parahaemolyticus, Vibrio vulnificus, Bacteroides fragilis, Clostridium difficile, Salmonella typhimurium, Salmonella typhi, Salmonella gallinarum, Salmonella pullorum, Salmonella choleraesuis, Salmonella enteritidis, Streptococcus gordonii, Lactobacillis sp., Klebsiella pneumoniae, Enterobacter cloacae, and Enterococcus faecalis.

* * * * *